(12) United States Patent
Mevorach et al.

(10) Patent No.: US 11,883,429 B2
(45) Date of Patent: *Jan. 30, 2024

(54) THERAPEUTIC POOLED BLOOD APOPTOTIC CELL PREPARATIONS AND USES THEREOF

(71) Applicant: Enlivex Therapeutics RDO Ltd, Nes-Ziona (IL)

(72) Inventors: Dror Mevorach, Jerusalem (IL); Shai Novik, Ramat Hasharon (IL)

(73) Assignee: Enlivex Therapeutics RDO Ltd, Nes-Ziona (IL)

( * ) Notice: Subject to any disclaimer, the term of this patent is extended or adjusted under 35 U.S.C. 154(b) by 571 days.

This patent is subject to a terminal disclaimer.

(21) Appl. No.: 17/075,721

(22) Filed: Oct. 21, 2020

(65) Prior Publication Data

US 2021/0038644 A1     Feb. 11, 2021

Related U.S. Application Data

(63) Continuation of application No. 15/567,376, filed as application No. PCT/IL2016/050430 on Apr. 21, 2016, now Pat. No. 10,857,181.

(60) Provisional application No. 62/150,305, filed on Apr. 21, 2015.

(51) Int. Cl.
| | | |
|---|---|---|
| A61K 35/15 | (2015.01) |
| A61K 39/00 | (2006.01) |
| C12N 5/078 | (2010.01) |
| A61K 35/17 | (2015.01) |
| A61P 37/00 | (2006.01) |
| A61K 9/00 | (2006.01) |
| A61K 35/12 | (2015.01) |

(52) U.S. Cl.
CPC ............ A61K 35/15 (2013.01); A61K 9/0019 (2013.01); A61K 35/17 (2013.01); A61K 39/0008 (2013.01); A61P 37/00 (2018.01); C12N 5/0634 (2013.01); A61K 2035/122 (2013.01); A61K 2039/515 (2013.01); A61K 2039/58 (2013.01); C12N 2501/39 (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 4,956,778 A | 9/1990 | Naito |
| 5,091,513 A | 2/1992 | Huston et al. |
| 5,132,405 A | 7/1992 | Huston et al. |
| 5,906,936 A | 5/1999 | Eshhar et al. |
| 5,912,172 A | 6/1999 | Eshhar et al. |
| 7,056,660 B1 | 6/2006 | Giesing et al. |
| 7,521,197 B2 | 4/2009 | Savage et al. |
| 7,652,065 B2 | 1/2010 | Albeck et al. |
| 7,771,715 B2 | 8/2010 | Schlom et al. |
| 7,772,373 B2 | 8/2010 | Hansen et al. |
| 7,931,903 B2 | 4/2011 | Hansen et al. |
| 8,119,101 B2 | 2/2012 | Byrd et al. |
| 8,147,800 B2 | 4/2012 | McBride et al. |
| 8,211,422 B2 | 7/2012 | Eshhar et al. |
| 8,268,317 B2 | 9/2012 | Govindan et al. |
| 8,481,003 B2 | 7/2013 | Griffiths et al. |
| 8,506,954 B2 | 8/2013 | Strober et al. |
| 8,834,886 B2 | 9/2014 | Govindan et al. |
| 8,846,026 B2 | 9/2014 | Plebanski et al. |
| 8,889,616 B2 | 11/2014 | Peterson et al. |
| 10,857,181 B2 | 12/2020 | Mevorach et al. |
| 10,927,343 B2 | 2/2021 | Mevorach et al. |
| 11,000,548 B2 | 5/2021 | Novik et al. |
| 11,304,976 B2 | 4/2022 | Novik et al. |
| 11,318,163 B2 | 5/2022 | Novik et al. |
| 11,512,289 B2 | 11/2022 | Novik et al. |
| 2001/0033839 A1 | 10/2001 | Barbera-Guillem |
| 2002/0137697 A1 | 9/2002 | Eshhar et al. |
| 2002/0193569 A1 | 12/2002 | Hanna |
| 2003/0036505 A1 | 2/2003 | Barash et al. |
| 2003/0207287 A1 | 11/2003 | Short |
| 2004/0009939 A1 | 1/2004 | Chada et al. |

(Continued)

FOREIGN PATENT DOCUMENTS

| | | |
|---|---|---|
| WO | WO 1993/019163 A1 | 9/1993 |
| WO | WO 1997/015669 A1 | 5/1997 |

(Continued)

OTHER PUBLICATIONS

Amarilyo, Gil, et al. "iCSb-opsonized apoptotic cells mediate a distinct anti-inflammatory response and transcriptional NF-κB-dependent blockade." European Journal of Immunology 40(3):699-709, 2010.

(Continued)

*Primary Examiner* — Daniel C Gamett
(74) *Attorney, Agent, or Firm* — Mark S Cohen; PEARL COHEN ZEDEK LATZER BARATZ LLP

(57) ABSTRACT

Cell preparations comprising a pooled and enriched, mononuclear apoptotic cell population, and a method of preparing this cell preparation are described. The pooled mononuclear apoptotic cell preparation may be obtained from pooled, allogeneic white blood cell fractions that are pooled prior to or following induction of apoptosis. Further, described herein are methods of use of these pooled apoptotic cell preparations for treating an immune disease, an inflammatory disease, an autoimmune disease, or infertility in a subject. For example, a pooled apoptotic cell preparation may be used to treat graft versus host disease (GVHD) in an allogeneic subject.

26 Claims, 5 Drawing Sheets

(56) References Cited

U.S. PATENT DOCUMENTS

| | | |
|---|---|---|
| 2004/0018557 A1 | 1/2004 | Qu et al. |
| 2004/0019195 A1 | 1/2004 | Scholm et al. |
| 2004/0053348 A1 | 3/2004 | Faris et al. |
| 2004/0072288 A1 | 4/2004 | Collas et al. |
| 2004/0083497 A1 | 4/2004 | Raitano et al. |
| 2004/0115193 A1 | 6/2004 | Hansen et al. |
| 2004/0192597 A1 | 9/2004 | Raitano et al. |
| 2004/0202666 A1 | 10/2004 | Griffiths |
| 2004/0213778 A1 | 10/2004 | Challita-Eid et al. |
| 2004/0214212 A1 | 10/2004 | Raitano et al. |
| 2004/0214783 A1 | 10/2004 | Terman et al. |
| 2004/0219156 A1 | 11/2004 | Goldenberg et al. |
| 2004/0253245 A1 | 12/2004 | Briend et al. |
| 2005/0079184 A1 | 4/2005 | Hsing-Chang et al. |
| 2005/0084913 A1 | 4/2005 | Punnonen et al. |
| 2005/0113297 A1 | 5/2005 | Francois et al. |
| 2005/0136435 A1 | 6/2005 | Kanner et al. |
| 2005/0191311 A1 | 9/2005 | Raitano et al. |
| 2005/0191312 A1 | 9/2005 | Raitano et al. |
| 2005/0191313 A1 | 9/2005 | Barbera-Guillem |
| 2005/0196754 A1 | 9/2005 | Drmanac et al. |
| 2005/0202098 A1 | 9/2005 | Mevorach |
| 2005/0276822 A1 | 12/2005 | Wiseman et al. |
| 2006/0029940 A1 | 2/2006 | Ge et al. |
| 2006/0052295 A1 | 3/2006 | Terman |
| 2006/0140936 A1 | 6/2006 | Goldenberg et al. |
| 2006/0193865 A1 | 8/2006 | Govindan et al. |
| 2006/0228357 A1 | 10/2006 | Chang et al. |
| 2007/0059729 A1 | 3/2007 | Faris et al. |
| 2007/0086942 A1 | 4/2007 | Chang et al. |
| 2007/0298051 A1 | 12/2007 | Barouch et al. |
| 2008/0004287 A1 | 1/2008 | Ma et al. |
| 2008/0081791 A1 | 4/2008 | Huang et al. |
| 2008/0108794 A1 | 5/2008 | Goldenberg |
| 2008/0138333 A1 | 6/2008 | Hansen et al. |
| 2008/0159993 A1 | 7/2008 | Stauss |
| 2008/0166342 A1 | 7/2008 | Hansen |
| 2008/0166363 A1 | 7/2008 | Govindan et al. |
| 2008/0181885 A1 | 7/2008 | Raitano et al. |
| 2008/0241141 A1 | 10/2008 | Goldenberg |
| 2008/0241145 A1 | 10/2008 | Goldenberg |
| 2009/0041804 A1 | 2/2009 | Schlom et al. |
| 2009/0123467 A1 | 5/2009 | Bedi et al. |
| 2009/0155166 A1 | 6/2009 | McBride et al. |
| 2009/0162315 A1 | 6/2009 | Terman et al. |
| 2009/0192114 A1 | 7/2009 | Ovcharenko et al. |
| 2009/0214550 A1 | 8/2009 | Sahin et al. |
| 2009/0215895 A1 | 8/2009 | Ferrante et al. |
| 2009/0298195 A1 | 12/2009 | Ruker et al. |
| 2010/0015046 A1 | 1/2010 | Govindan et al. |
| 2010/0040589 A1 | 2/2010 | Spetz-holmgren et al. |
| 2010/0104589 A1 | 4/2010 | Govindan et al. |
| 2010/0119511 A1 | 5/2010 | Wang et al. |
| 2010/0135974 A1 | 6/2010 | Eshhar et al. |
| 2010/0233251 A1 | 9/2010 | Von Andrian et al. |
| 2010/0266496 A1 | 10/2010 | Hansen et al. |
| 2010/0266497 A1 | 10/2010 | Hansen et al. |
| 2010/0272636 A1 | 10/2010 | Byrd et al. |
| 2011/0008393 A1 | 1/2011 | Kanner et al. |
| 2011/0027295 A1 | 2/2011 | Powell et al. |
| 2011/0038869 A1 | 2/2011 | Van Den Brink et al. |
| 2011/0183870 A1 | 7/2011 | Pan et al. |
| 2011/0280801 A1 | 11/2011 | McBride et al. |
| 2011/0293513 A1 | 12/2011 | Govindan et al. |
| 2011/0300156 A1 | 12/2011 | Verploegen et al. |
| 2011/0311450 A1 | 12/2011 | Levine et al. |
| 2012/0082725 A1 | 4/2012 | Plebanski |
| 2012/0093842 A1 | 4/2012 | Eshhar et al. |
| 2012/0196762 A1 | 8/2012 | Paradis et al. |
| 2012/0201746 A1 | 8/2012 | Liu et al. |
| 2012/0219617 A1 | 8/2012 | Peterson et al. |
| 2012/0328564 A1 | 12/2012 | Govindan et al. |
| 2013/0039911 A1 | 2/2013 | Bedi et al. |
| 2013/0045191 A1 | 2/2013 | Weinschenk et al. |
| 2013/0095034 A1 | 4/2013 | Griffiths et al. |
| 2013/0101590 A1 | 4/2013 | Arnett et al. |
| 2013/0136718 A1 | 5/2013 | Chang et al. |
| 2013/0156794 A1 | 6/2013 | Eshhar et al. |
| 2013/0171064 A1 | 7/2013 | Hansen et al. |
| 2013/0177498 A1 | 7/2013 | Goldenberg et al. |
| 2013/0259891 A1 | 10/2013 | Harn, Jr. et al. |
| 2013/0280220 A1 | 10/2013 | Ahmed et al. |
| 2013/0287857 A1 | 10/2013 | Von Andrian et al. |
| 2014/0030273 A1 | 1/2014 | Verploegen et al. |
| 2014/0050660 A1 | 2/2014 | Chang et al. |
| 2014/0050709 A1 | 2/2014 | Leen et al. |
| 2014/0099254 A1 | 4/2014 | Chang et al. |
| 2014/0099258 A1 | 4/2014 | Govindan et al. |
| 2014/0099309 A1 | 4/2014 | Powell, Jr. et al. |
| 2014/0134265 A1 | 5/2014 | Buggy et al. |
| 2014/0271582 A1 | 9/2014 | Forman et al. |
| 2014/0294765 A1 | 10/2014 | Cojocaru et al. |
| 2014/0336105 A1 | 11/2014 | Shai et al. |
| 2014/0341917 A1 | 11/2014 | Nastri et al. |
| 2015/0023937 A1 | 1/2015 | Vera Valdes et al. |
| 2015/0025812 A1 | 1/2015 | Paradis et al. |
| 2015/0275175 A1 | 10/2015 | Mevorach et al. |
| 2017/0360836 A1 | 12/2017 | Novik et al. |
| 2018/0094244 A1 | 4/2018 | Novik et al. |
| 2018/0104277 A1 | 4/2018 | Mevorach et al. |
| 2019/0083535 A1 | 3/2019 | Novik et al. |
| 2019/0175649 A1 | 6/2019 | Novik et al. |
| 2020/0009191 A1 | 1/2020 | Novik et al. |
| 2020/0009192 A1 | 1/2020 | Novik et al. |
| 2020/0061116 A1 | 2/2020 | Novik et al. |
| 2020/0121718 A1 | 4/2020 | Novik et al. |
| 2020/0289557 A1 | 9/2020 | Novik et al. |
| 2021/0106617 A9 | 4/2021 | Novik et al. |
| 2021/0228633 A1 | 7/2021 | Novik et al. |
| 2022/0133799 A1 | 5/2022 | Novik et al. |

FOREIGN PATENT DOCUMENTS

| | | |
|---|---|---|
| WO | WO 2000/031239 A1 | 6/2000 |
| WO | WO 2001/089536 A2 | 11/2001 |
| WO | WO 2001/089537 A2 | 11/2001 |
| WO | WO 2001/097844 A1 | 12/2001 |
| WO | WO 2002/082041 A2 | 10/2002 |
| WO | WO 2003/029293 A2 | 4/2003 |
| WO | WO 2003/033654 A2 | 4/2003 |
| WO | WO 2003/074567 A2 | 9/2003 |
| WO | WO 2003/074569 A2 | 9/2003 |
| WO | WO 2004/016734 A2 | 2/2004 |
| WO | WO 2004/016736 A2 | 2/2004 |
| WO | WO 2004/016762 A2 | 2/2004 |
| WO | WO 2004/016799 A2 | 2/2004 |
| WO | WO 2004/039412 A2 | 5/2004 |
| WO | WO 2004/058298 A1 | 7/2004 |
| WO | WO 2004/061113 A2 | 7/2004 |
| WO | WO 2004/067038 A1 | 8/2004 |
| WO | WO 2004/067716 A2 | 8/2004 |
| WO | WO 2004/076644 A2 | 9/2004 |
| WO | WO 2004/093808 A2 | 11/2004 |
| WO | WO 2004/098515 A2 | 11/2004 |
| WO | WO 2004/108753 A1 | 12/2004 |
| WO | WO 2005/014618 A2 | 2/2005 |
| WO | WO 2005/014780 A2 | 2/2005 |
| WO | WO 2005/019429 A2 | 3/2005 |
| WO | WO 2005/049852 A2 | 6/2005 |
| WO | WO 2005/052119 A2 | 6/2005 |
| WO | WO 2005/073164 A1 | 8/2005 |
| WO | WO 2005/117846 | 12/2005 |
| WO | WO 2005/123908 A2 | 12/2005 |
| WO | WO 2006/000787 A2 | 1/2006 |
| WO | WO 2006/004620 A2 | 1/2006 |
| WO | WO 2006/022722 A1 | 3/2006 |
| WO | WO 2006/055004 A1 | 5/2006 |
| WO | WO 2006/063150 A2 | 6/2006 |
| WO | WO 2006/072620 A1 | 7/2006 |
| WO | WO 2006/117786 A1 | 11/2006 |
| WO | WO 2006/120439 | 11/2006 |
| WO | WO 2006/107617 A2 | 12/2006 |
| WO | WO 2006/135454 A1 | 12/2006 |
| WO | WO 2007/046893 A2 | 4/2007 |

(56) References Cited

FOREIGN PATENT DOCUMENTS

| | | |
|---|---|---|
| WO | WO 2008/005268 A1 | 1/2008 |
| WO | WO 2008/056174 A2 | 5/2008 |
| WO | WO 2008/095141 A2 | 8/2008 |
| WO | WO 2008/137901 A2 | 11/2008 |
| WO | WO 2010/070105 A1 | 6/2010 |
| WO | WO 2011/088226 A2 | 7/2011 |
| WO | WO 2011/109440 A1 | 9/2011 |
| WO | WO 2011/109789 A2 | 9/2011 |
| WO | WO 2011/110642 A2 | 9/2011 |
| WO | WO 2011/139629 A2 | 11/2011 |
| WO | WO 2011/140170 A1 | 11/2011 |
| WO | WO 2011/144358 A1 | 11/2011 |
| WO | WO 2011/147986 A1 | 12/2011 |
| WO | WO 2012/024543 A1 | 2/2012 |
| WO | WO 2012/088302 A2 | 6/2012 |
| WO | WO 2012/104344 A1 | 8/2012 |
| WO | WO 2012/115885 A1 | 8/2012 |
| WO | WO 2012/116225 A2 | 8/2012 |
| WO | WO 2012/138858 A1 | 10/2012 |
| WO | WO 2012/174282 A2 | 12/2012 |
| WO | WO 2013/022995 A2 | 2/2013 |
| WO | WO 2013/025972 A1 | 2/2013 |
| WO | WO 2013/079174 A1 | 6/2013 |
| WO | WO 2013/105089 A2 | 7/2013 |
| WO | WO 2013/112801 A1 | 8/2013 |
| WO | WO 2013/130683 A2 | 9/2013 |
| WO | WO 2013/136334 A2 | 9/2013 |
| WO | WO 2013/155375 A1 | 10/2013 |
| WO | WO 2014/011984 A1 | 1/2014 |
| WO | WO 2014/028560 A2 | 2/2014 |
| WO | WO 2014/055657 A1 | 4/2014 |
| WO | WO 2014/071231 A1 | 5/2014 |
| WO | WO 2014/071379 A1 | 5/2014 |
| WO | WO 2014/080251 A1 | 5/2014 |
| WO | WO 2014/082083 A1 | 5/2014 |
| WO | WO 2014/087408 A1 | 6/2014 |
| WO | WO 2014/106666 | 7/2014 |
| WO | WO 2014/068408 A2 | 8/2014 |
| WO | WO 2014/122467 A1 | 8/2014 |
| WO | WO 2014/138704 A1 | 9/2014 |
| WO | WO 2014/144622 A2 | 9/2014 |
| WO | WO 2014/145578 A1 | 9/2014 |
| WO | WO 2014/151085 A1 | 9/2014 |
| WO | WO 2014/153114 A1 | 9/2014 |
| WO | WO 2014/163684 A1 | 10/2014 |
| WO | WO 2014/164554 A1 | 10/2014 |
| WO | WO 2014/172584 A1 | 10/2014 |
| WO | WO 2014/186773 A1 | 11/2014 |
| WO | WO 2014/193999 A2 | 12/2014 |
| WO | WO 2014/197638 | 12/2014 |
| WO | WO 2014/197638 A2 | 12/2014 |
| WO | WO 2014/201021 A2 | 12/2014 |
| WO | WO 2015/010096 A1 | 1/2015 |
| WO | WO 2015/089495 A2 | 6/2015 |
| WO | WO 2016/132366 A1 | 8/2016 |
| WO | WO 2016/170541 A1 | 10/2016 |
| WO | WO 2017/141243 | 8/2017 |
| WO | WO 2019/038758 A1 | 2/2019 |

OTHER PUBLICATIONS

Barrett, David M., et al. "Treatment of advanced leukemia in mice with mRNA engineered T cells." Human Gene Therapy 22(12) 1575-1586, 2011. Abstract only.

Barrett, David M., et al. "Chimeric antigen receptor therapy for cancer." Annual Review of Medicine 65: 333-347, 2014. Abstract only.

Brentjens, Renier J., et al. "Eradication of systemic B-cell tumors by genetically targeted human T lymphocytes co-stimulated by CD80 and interleukin-15." Nature Medicine 9(3): 279, 2003.

Brentjens, Renier J., et al. "Genetically targeted T cells eradicate systemic acute lymphoblastic leukemia xenografts." Clinical Cancer Research 13(18): 5426-5435, 2007.

Brentjens, Renier J., et al. "Safety and persistence of adoptively transferred autologous CD19-targeted T cells in patients with relapsed or chemotherapy refractory B-cell leukemias." Blood 118.18: 4817-4828, 2011.

Brentjens, Renier J., et al. "CD19-targeted T cells rapidly induce molecular remissions in adults with chemotherapy-refractory acute lymphoblastic leukemia." Science Translational Medicine 5(177): 138-177, 2013. Abstract only.

Brigham, Kenneth L., et al. "Rapid communication: In vivo transfection of murine lungs with a functioning prokaryotic gene using a liposome vehicle." The American Journal of The Medical Sciences 298(4): 278-281, 1989.

Brocks, Bodo, et al. "A TNF receptor antagonistic scFv, which is not secreted in mammalian cells, is expressed as a soluble mono-and bivalent scFv derivative in insect cells." Immunotechnology 3(3):173-184, 1997.

Canna, Scott W., and Edward M. Behrens. "Making sense of the cytokine storm: a conceptual framework for understanding, diagnosing, and treating hemophagocytic syndromes." Pediatric Clinics 59(2): 329-344, 2012.

Cartellieri, M, "Chimeric antigen receptor-engineered T cells for immunotherapy of cancer". Journal of Biomedicine and Biotechnology, Article ID 956304, doi:10.1155/2010/956304, 2010.

Champlin, Richard, et al. "Selective depletion of CD8+ T lymphocytes for prevention of graft-versus-host disease after allogeneic bone marrow transplantation." Blood 76(2): 418-423, 1990.

Cheadle, Eleanor J., et al. "Differential role of Th1 and Th2 cytokines in autotoxicity driven by CD19-specific second-generation chimeric antigen receptor T cells in a mouse model." The Journal of Immunology 192(8): 3654-3665, 2014.

Chekmasova, Alena A., et al. "Successful eradication of established peritoneal ovarian tumors in SCID-Beige mice following adoptive transfer of T cells genetically targeted to the MUC16 antigen." Clinical Cancer Research 16(14): 3594-3606, 2010.

Cheng, Min, et al. "NK cell-based immunotherapy for malignant diseases." Cellular & Molecular Immunology 10(3): 230, 2013.

Clair, E. William St. "The calm after the cytokine storm: lessons from the TGN1412 trial." The Journal of clinical investigation 118(4): 1344-1347, 2008.

Cooke, Kenneth R., et al. "An experimental model of idiopathic pneumonia syndrome after bone marrow transplantation: I. The roles of minor H antigens and endotoxin." Blood 88(8): 3230-3239, 1996.

Curran, Kevin J., Hollie J. Pegram, and Renier J. Brentjens. "Chimeric antigen receptors for T cell immunotherapy: current understanding and future directions." The Journal of Gene Medicine 14(6): 405-415, 2012.

Davila, Marco L. et al. "How do CARs work? Early insights from recent clinical studies targeting CD19." Oncoimmunology 1(9): 1577-1583, 2012.

Davila, Marco L., et al. "CD19 CAR-targeted T cells induce long-term remission and B Cell Aplasia in an immunocompetent mouse model of B cell acute lymphoblastic leukemia." PLOS one 8(4): e61338, 2013.

Davila, Marco L., et al. "Efficacy and toxicity management of 19-282 CAR T cell therapy in B cell acute lymphoblastic leukemia." Science Translational Medicine 6(224): 224-225, 2014.

Essand, Magnus, and Angelica SI Loskog. "Genetically engineered T cells for the treatment of cancer." Journal of Internal Medicine 273(2): 166-181, 2013.

Felgner, Philip L., et al. "Lipofection: a highly efficient, lipid-mediated DNA-transfection procedure." Proceedings of the National Academy of Sciences 84(21): 7413-7417, 1987.

Fife, Brian T., et al. "Inhibition of T cell activation and autoimmune diabetes using a B cell surface-linked CTLA-4 agonist." The Journal of Clinical Investigation 116(8): 2252-2261, 2006.

Gallardo, D., et al. "Low-dose donor CD8+ cells in the CD4-depleted graft prevent allogeneic marrow graft rejection and severe graft-versus-host disease for chronic myeloid leukemia patients in first chronic phase." Bone Marrow Transplantation 20(11): 945, 1997.

(56) References Cited

OTHER PUBLICATIONS

Ganss, Ruth, et al. "Combination of T-cell therapy and trigger of inflammation induces remodeling of the vasculature and tumor eradication." Cancer Research 62: 1462-1470, (March 2002).

Giomarelli, Barbara, et al. "Inhibition of thrombin-induced platelet aggregation using human single-chain Fv antibodies specific for TREM-like transcript-1." Thrombosis and Haemostasis 97(06): 955-963, 2007.

Goding, James W. Monoclonal antibodies: principles and practice. Elsevier, pp. 59-103, 1996.

Gong, Michael C., et al. "Cancer patient T cells genetically targeted to prostate-specific membrane antigen specifically lyse prostate cancer cells and release cytokines in response to prostate-specific membrane antigen." Neoplasia 1(2): 123-127, 1999.

Grau, Amir, et al. "Apoptotic cells induce NF-κB and inflammasome negative signaling." PloS one 10(3): e0122440, 2015.

Haji-Fatahaliha, Mostafa, et al. "CAR-modified T-cell therapy for cancer: an updated review." Artificial Cells, Nanomedicine, and Biotechnology 44(6): 1339-1349,2016.

Han, Ethan Q., et al. "Chimeric antigen receptor-engineered T cells for cancer immunotherapy: progress and challenges." Journal of Hematology & Oncology 69(47), 2013.

Ho, Mitchell, and Mariangela Segre. "Inhibition of cocaine binding to the human dopamine transporter by a single chain anti-idiotypic antibody: its cloning, expression, and functional properties." Biochimica et Biophysica Acta (BBA)-Molecular Basis of Disease 1638(3): 257-266, 2003.

Hoffman, Hal M., et al. "Mutation of a new gene encoding a putative pyrin-like protein causes familial cold autoinflammatory syndrome and Muckle-Wells syndrome." Nature genetics 29.3: 301, 2001.

Huston, James S., et al. "Protein engineering of antibody binding sites: recovery of specific activity in an anti-digoxin single-chain Fv analogue produced in *Escherichia coli*." Proceedings of the National Academy of Sciences 85(16): 5879-5883, 1988.

Jagasia, Madan H., et al. "National Institutes of Health consensus development project on criteria for clinical trials in chronic graft-versus-host disease: I. The 2014 Diagnosis and Staging Working Group report." Biology of Blood and Marrow Transplantation 21(3): 389-401, 2015.

Jensen, Michael C., and Stanley R. Riddell. "Design and implementation of adoptive therapy with chimeric antigen receptor-modified T cells." Immunological Reviews 257(1): 127-144, 2014. Abstract only.

Kalinski, Pawel. "Regulation of immune responses by prostaglandin E2." The Journal of Immunology 188(1): 21-28, 2012.

Karlsson, S. C. H., et al. "Combining CAR T cells and the Bcl-2 family apoptosis inhibitor ABT-737 for treating B-cell malignancy." Cancer Gene Therapy 20(7): 386, 2013.

Kobayashi, Eiji, et al. "A chimeric antigen receptor for TRAIL-receptor 1 induces apoptosis in various types of tumor cells." Biochemical and Biophysical Research Communications 453(4): 798-803, 2014.

Kochenderfer, James N., et al. "B-cell depletion and remissions of malignancy along with cytokine-associated toxicity in a clinical trial of anti-CD19 chimeric-antigen-receptor-transduced T cells." Blood 119(12): 2709-2720, 2012.

Köhler, Georges, and Cesar Milstein. "Continuous cultures of fused cells secreting antibody of predefined specificity." Nature 256 (5517): 495, 1975.

Krispin, Alon, et al. "Apoptotic cell thrombospondin-1 and heparin-binding domain lead to dendritic-cell phagocytic and tolerizing states" Blood 108: 3580-3589, 2006.

Ledbetter, Jeffrey A., et al. "Agonistic activity of a CD40-specific single-chain Fv constructed from the variable regions of mAb G28-5." Critical Reviews in Immunology 17.5-6: 427-435, 1997. Abstract only.

Lee, Daniel W., et al. "Current concepts in the diagnosis and management of cytokine release syndrome." Blood 124, pp. 188-195, 2014.

Magenau, J., and P. Reddy. "Next generation treatment of acute graft-versus-host disease." Leukemia 28 (12): 2283, 2014.

Maldarelli, Frank, et al. "Specific HIV integration sites are linked to clonal expansion and persistence of infected cells." Science vol. 345 Issue 6193: 179-183, 2014.

Marcondes, A. Mario, et al. "α-1-Antitrypsin (AAT)-modified donor cells suppress GVHD but enhance the GVL effect: a role for mitochondrial bioenergetics." Blood 124 (18): 2881-2891, 2014.

Martínez, Carmen, and Alvaro Urbano-Ispízua. "Graft-versus-host disease therapy: something else beyond glucocorticoids?" Haematologica, Journal of The Ferrata Stori Foundation, vol. 96, Issue 9:1249-1251, 2011.

Maude, Shannon L., et al. "Managing cytokine release syndrome associated with novel T cell-engaging therapies." Cancer Journal (Sudbury, Mass.) 20 (2): 119, 2014.

McClain, Kenneth L., and Olive Eckstein. "Clinical features and diagnosis of hemophagocytic lymphohistiocytosis." UpToDate p. 1-22, 2016. https://www.uptodate.com/contents/clinical-features-and-diagnosis-of-hemophagocytic-lymphohistiocytosis.

Mevorach, Dror, et al. "Single infusion of donor mononuclear early apoptotic cells as prophylaxis for graft-versus-host disease in myeloablative HLA-matched allogeneic bone marrow transplantation: a phase I/IIa clinical trial." Biology of Blood and Marrow Transplantation 20 (1): 58-65, 2014.

Mevorach, Dror, et al. "Early Apoptotic Cells (ApoCell) As Prophylaxis of Graft-Versus-Host Disease Is Safe and Effective: 1 Year Follow-up and Mechanism of Action." Biology of Blood and Marrow Transplantation 21 (2): S339-S340, 2015.

Mevorach Dror et al., Apoptotic Cells for the Prevention of Cytokine Release Syndrome (CRS) in CAR T-Cell Therapy, Blood 128:1626, 2016.

Moosmayer, D., et al. "A single-chain TNF receptor antagonist is an effective inhibitor of TNF mediated cytotoxicity." Therapeutic Immunology 2 (1): 31-40, 1995.

Neven, Bénédicte, Anne-Marie Prieur, and Pierre Quartier dit Maire. "Cryopyrinopathies: update on pathogenesis and treatment." Nature Reviews Rheumatology 4 (9): 481, 2008.

Ono, Tomoko, et al. "Plasmid DNAs directly injected into mouse brain with lipofectin can be incorporated and expressed by brain cells." Neuroscience Letters 117 (3): 259-263, 1990.

Peter, Jean-Christophe, et al. "scFv single chain antibody variable fragment as inverse agonist of the β2-adrenergic receptor." Journal of Biological Chemistry 278 (38): 36740-36747, 2003.

Peter, Jean-Christophe, et al. "Protective effects of an anti-melanocortin-4 receptor scFv derivative in lipopo lysaccharide-induced cachexia in rats." Journal of Cachexia, Sarcopenia and Muscle 4(1): 79-88, 2013.

Poon, Ivan KH, et al. "Apoptotic cell clearance: basic biology and therapeutic potential." Nature Reviews Immunology 14(3): 166, 2014.

Pupjalis, Danute, et al. "Annexin A1 released from apoptotic cells acts through formyl peptide receptors to dampen inflammatory monocyte activation via JAK/STAT/SOCS signaling." EMBO Molecular Medicine 3(2): 102-114, 2011.

Sharpe, Michaela, and Natalie Mount. "Genetically modified T cells in cancer therapy: opportunities and challenges." Disease Models & Mechanisms 8 (4): 337-350, 2015.

Stebbings, R., et al. "After TGN1412: recent developments in cytokine release assays." Journal of Immunotoxicology 10 (1): 75-82, 2013.

Sadelain, Michel, Renier Brentjens, and Isabelle Riviere. "The basic principles of chimeric antigen receptor design" Cancer Discovery 3(4): pp. 388-398, 2013.

Shieh, Shing-Jia, et al. "Transgenic expression of single-chain anti-CTLA-4 Fv on β cells protects nonobese diabetic mice from autoimmune diabetes." The Journal of Immunology 183 (4): 2277-2285, 2009.

Tarrant, Jacqueline M. "Blood cytokines as biomarkers of in vivo toxicity in preclinical safety assessment: considerations for their use." Toxicological Sciences 117 (2): 4-16, 2010.

Tawara, Isao, et al. "Alpha-1-antitrypsin monotherapy reduces graft-versus-host disease after experimental allogeneic bone mar-

(56) References Cited

OTHER PUBLICATIONS row transplantation." Proceedings of the National Academy of Sciences 109 (2): 564-569, 2012.
Teachey, David T., et al. "Cytokine release syndrome after blinatumomab treatment related to abnormal macrophage activation and ameliorated with cytokine-directed therapy." Blood 121(26): 5154-5157, 2013.
Themeli, Maria, Isabelle Rivière, and Michel Sadelain. "New cell sources for T cell engineering and adoptive immunotherapy." Cell stem cell 16(4): 357-366, 2015.
Tschopp, Jürg, Fabio Martinon, and Kimberly Burns. "NALPs: a novel protein family involved in inflammation." Nature reviews Molecular cell biology 4 (2): 95,2003. Abstract only.
Verbovetski, Inna, et al. "Opsonization of apoptotic cells by autologous iC3b facilitates clearance by immature dendritic cells, down-regulates DR and CD86, and up-regulates CC chemokine receptor 7." Journal of Experimental Medicine 196 (12): 1553-1561, 2002.
Van der Stegen, Sjoukje JC, et al. "Preclinical in vivo modeling of cytokine release syndrome induced by ErbB-retargeted human T cells: identifying a window of therapeutic opportunity?" The Journal of Immunology 191(9): 4589-4598, 2013.
Van Der Stegen, Sjoukje JC, Mohamad Hamieh, and Michel Sadelain. "The pharmacology of second-generation chimeric antigen receptors." Nature reviews Drug discovery 14 (7): 499, 2015. Abstract only.
Wagner, Thor A., et al. "Proliferation of cells with HIV integrated into cancer genes contributes to persistent infection." Science 345.6196: 570-573, 2014.
Wilkie, Scott, et al. "Retargeting of human T cells to tumor-associated MUC1: the evolution of a chimeric antigen receptor." The Journal of Immunology 180(7): 4901-4909, 2008.
Xu, Xiao-Jun, and Yong-Min Tang. "Cytokine release syndrome in cancer immunotherapy with chimeric antigen receptor engineered T cells." Cancer letters 343 (2): 172-178, 2014. Abstract only.
International Search Report and Written opinion issued for International Application No. PCT/IL2016/050194 dated May 18, 2016.
Supplementary European Search Report issued for EP 16752041 dated Jun. 14, 2018.
International Search Report and Written opinion issued for International Application No. PCT/IL2017/050196 dated Jun. 11, 2017.
Supplementary European Search Report issued for EP 16782737 dated Oct. 15, 2018.
International Search Report and Written opinion issued for International Application No. PCT/IL2016/050430 dated Jul. 13, 2016.
Ren Y. et al., "Apoptotic Cells Protect Mice against Lipopolysaccharide-Induced Shock", The Journal of Immunology, J Immunol Apr. 1, 180 (7) 4978-4985, 2008.
Munson and Rodbard, "LIGAND: A versatile computerized approach for characterization of ligand-binding systems", Analytical Biochemistry, vol. 107, Issue1 pp: 220-239, Sep. 1980.
Nelson J. Lee., "The Otherness of Self: Microchimerism in Heath and Disease", Trends in Immunology, vol. 33, Issue 8, pp. 421-427, Aug. 2012.
Wahl RL et al. "Improved radioimaging and tumor localization with monoclonal F(ab')2", Journal of Nuclear Medicine: Official Publication, Society of Nuclear Medicine, 24(4): 316-325, Apr. 1983.
Wilkie et al., "Selective Expansion of Chimeric Antigen Receptor-targeted T-cells with Potent Effector Function using Interleukin-4", The Journal of Biological Chemistry, 285, 25538-25544, 2010.
Wolff JA et al., "Direct gene transfer into mouse muscle in vivo", Science Mar. 1990: vol. 247, Issue 4949, pp. 1465-1468.
Wahl et al. "Molecular Hybridization of Immobilized Nucleic Acids: Theoretical Concepts and Practical Considerations", Methods in Enzymology, vol. 152, pp. 399-407, 1987.
Wu C H et al. "Targeting genes: delivery and persistent expression of a foreign gene driven by mammalian regulatory elements in vivo" Journal of Biological Chemistry, vol. 264, 16985-16987, 1989.
Wu and Wu et al., "Receptor-mediated gene delivery and expression in vivo" Journal of Biological Chemistry, vol. 263: 14621-14624, 1988.
Zhao et al., "Characteristics of an scFv Antibody Fragment That Binds to Immunoglobulin G of Graves' Disease Patients and Inhibits Autoantibody-Mediated Thyroid-Stimulating Activity" Hybridoma vol. 27 Issue 6: Dec. 2008.
Shrum, B., Anantha, R. V., Xu, S. X., Donnelly, M., Haeryfar, S. M., McCormick, J. K., & Mele, T. A robust scoring system to evaluate sepsis severity in an animal model. BMC research notes, 7(1), 233, 2014.
De Carvalho Bittencourt et al. Intravenous injection of apoptotic leukocytes enhances bone marrow engraftment across major histocompatibility barriers. Blood, 98(1), 224-230, 2001.
Saas, P., Kaminski, S., & Perruche, S. Prospects of apoptotic cell-based therapies for transplantation and inflammatory diseases. Immunotherapy, 5(10), 1055-1073, 2013.
Bonini et al. "Adoptive T-cell therapy for cancer: The era of engineered T cells" European iournal of immunology. Sep. 2015:45(9):2457-69.
Brink et al. "Pharmacokinetics of once-daily dosing of ertapenem in critically ill patients with severe sepsis" International journal of antimicrobial agents. May 1, 2009;33(5):432-6.
Burkovskiy et al. "Cytokine release in sepsis. Advances in bioscience and biotechnology" Aug. 26, 2013:4(09):860.
Butterfield LH. (2015) "Cancer vaccines" BMJ .(Clinical research ed.), 350, h988.
Byers T. "What can randomized controlled trials tell us about nutrition and cancer prevention?" CA: A Cancer Journal for Clinicians. Nov. 1999;49(6):353-61.
European Search Report for European Application No. 22194786.4 dated Jan. 5, 2023.
Griffith et al. "Cell death in the maintenance and abrogation of tolerance: the five Ws of dying cells" Immuity. Oct. 28, 2011;35(4):456-66.
Henson et al. (2013). "Anti inflammatory effects of apoptotic cells" The Journal of clinical investigation, 123(7); 2773-2774.
Higuchi et al. "CTLA-4 blockade synergizes therapeutically with PARP inhibition in BRCA1-deficient ovarian cancer" Cancer immunology research. Nov. 1, 2015;3(11):1257-68.
Iagăru et al. "Macrophage Activation Syndrome in Two Girls with Systemic Lupus Erythematosus" Therapeutics, Pharmacology & Clinical Toxicology. Sep. 1, 2010;14(3).
Inoue et al. "Dose dependent effect of anti-CTLA-4 on survival in sepsis" Shock (Augusta, Ga.). Jul. 2011;36(1):38.
Kobayashi Y. "The regulatory role of nitric oxide in proinflammatory cytokine expression during the induction and resolution of inflammation" Journal of leukocyte biology. Dec. 2010;88(6):1157-62.
Lorusso et al. "Accelerating cancer therapy development: the importance of combination strategies and collaboration. Summary of an Institute of Medicine workshop" Clinical Cancer Research. Nov. 15, 2012;18(22):6101-9.
Mevorach D. "Effect of Allocetra-OTS (off-the-shelf apoptotic cells) Therapy in Sepsis" Cytotherapy. May 1, 2020;22(5):S19.
Mohebtash et al. "Therapeutic prostate cancer vaccines: a review of the latest developments" Current opinion in investigational drugs (London, England: 2000). Dec. 2008;9(12):1296.
Morelli et al. "Apoptotic cell-based therapies against transplant rejection: role of recipient's dendritic cells" Apoptosis. Sep. 2010;15(9):1083-97.
Oda et al. "The Japanese guidelines for the management of sepsis" Journal of Intensive Care . . . 2014, 2:55.
Qi et al. "Research Progress in Apoptosis and Tumor Microenvironment" Medical Recapitulate 2017 22 4433-4442. Abstract.
Saas et al. "Intravenous apoptotic cell infusion as a cell-based therapy toward improving nematopoietic cell transplantation outcome" Annals of the New York Academy of Sciences. Oct. 2010;1209(1):118-26.
Tagliamonte et al. "Antigen-specific vaccines for cancer treatment" Human vaccines & immunotherapeutics. Nov. 2, 2014;10(11):3332-46.
Tisoncik et al. "Into the eye of the cytokine storm" Mircobiology and Molecular Biology Reviews. Mar. 2012;76(1):16-32.
Voll et al. "Immunosuppressive effects of apoptotic cells" Nature. Nov. 1997;390(6658):350-1.

(56) References Cited

OTHER PUBLICATIONS

Wang et al. "Use of the inhibitory effect of apoptotic cells on dendritic cells for graft survival via T-cell deletion and regulatory T cells" American Journal of Transplantation. Jun. 2006;6(6):1297-311.
Wolchok et al. "Nivolumab plus ipilimumab in advanced melanoma" N Engl J Med. Jul. 11, 2013;369:122-33.
Wood et al. "Understanding stem cell immunogenicity in therapeutic applications" Trends in immunology. Jan. 1, 2016;37(1):5-16.
Yang et al. "Challenges and opportunities of allogeneic donor-derived CAR T cells" Current opinion in hematology. Nov. 2015;22(6):509.

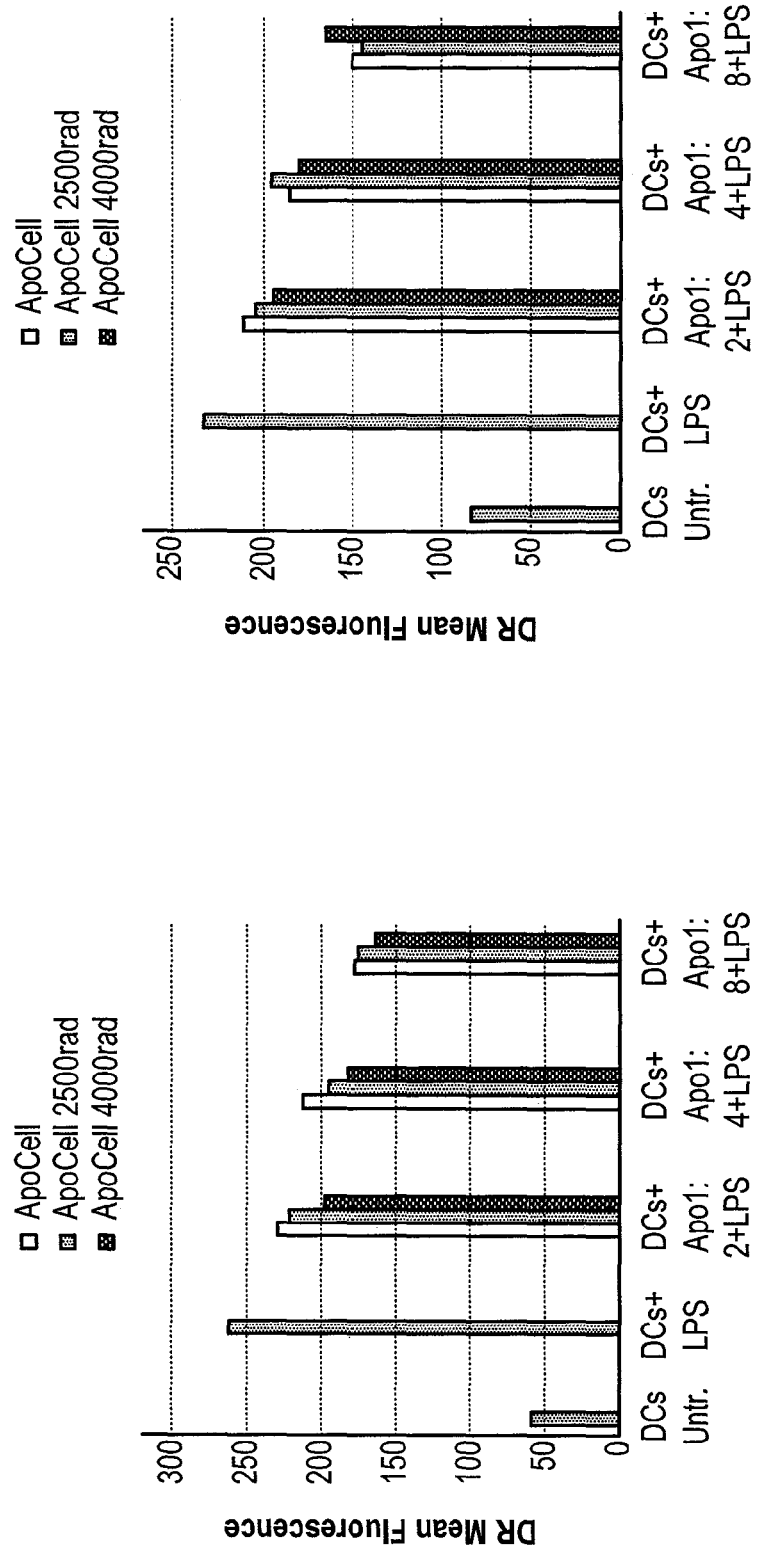

THERAPEUTIC POOLED BLOOD APOPTOTIC CELL PREPARATIONS AND USES THEREOF

CROSS-REFERENCE TO RELATED APPLICATIONS

This application is a Continuation Application of U.S. application Ser. No. 15/567,376, which filed on Oct. 18, 2017 as a National Phase Application of PCT International Application Number PCT/IL2016/050430, International filing date Apr. 21, 2016, which claims the benefit of U.S. Provisional Application Ser. No. 62/150,305 filed Apr. 21, 2015, which are hereby incorporated by reference in their entirety herein.

FIELD OF INTEREST

The present application is directed to cell preparations comprising a pooled and enriched, mononuclear apoptotic cell population and methods of preparing said cell preparation. Further, described herein the use of these pooled cell preparation for treating an immune disease, an inflammatory disease, a cytokine release syndrome (CRS), a cytokine storm, or an autoimmune disease in a subject.

BACKGROUND

Diseases characterized by pathological immune responses include many diseases associated with significant mortality and morbidity, particularly autoimmune diseases, such as systemic lupus erythematosus (SLE), and transplantation-related diseases such as graft-versus-host disease (GVHD). Autoimmune diseases may generally be divided into two general types, namely systemic autoimmune diseases (e.g. SLE and scleroderma), and organ specific autoimmune diseases, such as multiple sclerosis, and diabetes.

Immunosuppressive drugs have been used for treatment or prevention of the rejection of transplanted organs and tissues (e.g., bone marrow, heart, kidney, liver); for treatment of autoimmune diseases or diseases that are most likely of autoimmune origin (e.g., rheumatoid arthritis, multiple sclerosis, myasthenia gravis, systemic lupus erythematosus, sarcoidosis, Crohn's disease, Behcet's Disease, pemphigus, uveitis and ulcerative colitis); treatment of some other non-autoimmune inflammatory diseases (e.g., long term allergic asthma control) as well as transplantation-related diseases (e.g. GVHD). However, immunosuppressive drug treatments can lead to many complications, and improved methods for dealing with pathological immune reactions are needed.

In allogeneic bone marrow transplantation (alloBMT), the infusion of donor marrow into the patient's body entails the interaction of cells from two immune systems. Conditioning regimens for patients receiving allogeneic transplants allow the donor stem cells to engraft in the patient by suppressing the immune system. Once the donor's immune cells are established in the patient's body, they may recognize the patient's own tissue and cells, including any residual cancer cells, as being different or foreign. The immune system may then cause damage to certain organs such the liver, gastrointestinal tract or skin; this effect is known as graft-versus-host disease (GVHD).

As of today, GVHD prophylaxis comprises the combination of immunosuppressive drugs including a calcineurin inhibitor (CNI), cyclosporine or tacrolimus, and either methotrexate, mycophenolate mofetil (MMF), or sirolimus. However, acute GVHD still occurs in 35% to 70% of BMT patients who receive transplants from human leukocyte antigen (HLA)—matched siblings, and even more frequently in unrelated donor transplant recipients.

Although calcineurin inhibitors (CNIs) partially inhibit acute GVHD, they may impair immune reconstitution by inhibiting T-cell development and increasing the risk of disease relapse. Thus, patients with hematologic malignancies undergoing allogeneic BMT are in need of GVHD prophylaxis that would minimize the use of CNIs, prevent GVHD, and retain a functional immune system including a beneficial graft-versus-tumor effect.

Apoptotic cells are immunomodulatory cells capable of directly and indirectly inducing immune tolerance to dendritic cells and macrophages. Many animal experiments demonstrated an immunomodulatory effect independent of genetic matching. Suggestively, apoptotic cells from a non-genetically matched mouse were as effective as from a genetically matched mouse (syngeneic). The ability to combine non-genetically matched apoptotic blood samples, wherein the process for creating stable apoptotic cells with high tolerogenic potential (having immunotolerance) from peripheral cells (leukapheresis) collected from patients or donors is highly reproducible may provide a unique and cost effective source for inducing immune tolerance in a subject.

Yet, the use of non-matched white blood cells (WBC) raises two potential problems. First is a possible immune response against the apoptotic cells (in the process of cell death). Second, would be a response from the fraction of living cells that remains in any pool of apoptotic cells, since not all of the WBCs induced to create an apoptotic population necessarily become apoptotic. Thus, a fraction of administered apoptotic WBCs would contain some living cells. Living cells may elicit GVHD in the recipient.

Currently, about 1,000 units of blood are processed per day in Israel from donors, mostly through Magen David Adom (MDA). The WBC fraction is either unprocessed or is processed as buffy coat for research use. It is possible to receive this WBC fraction in a bag in which there are nearly $2 \times 10^7$ white blood cells, of which about $0.7 \times 10^7$ are mononuclear cells, which are preferred for apoptotic cell production. According to the current estimate, production efficiency is approximately 50%.

There remains an unmet need for compositions and methods for treating or preventing immune disorders including autoimmune and inflammatory diseases and transplantation related diseases. For instance, GVHD, with an estimated incidence of 30%-70%, remains the main barrier for successful allogeneic blood or marrow transplantation, and the optimal approach for GVHD prophylaxis has not yet been established. In particular, it is essential to obtain compositions and methods that prevent or ameliorate GVHD in a safe, reliable, reproducible and effective manner.

The cell preparation and compositions thereof, described herein below, address this need by providing a universal product comprising pooled apoptotic cells obtained from multiple individual blood donors or individual blood donations. Further, the pooled apoptotic cell preparation may be used to treat immune disorders including autoimmune and inflammatory diseases, transplantation related diseases and conditions, a cytokine release syndrome (CRS), a cytokine storm, and infertility.

SUMMARY

In one aspect, disclosed herein is a pooled mononuclear apoptotic cell preparation comprising mononuclear cells in an early-apoptotic state, wherein said pooled mononuclear apoptotic cell preparation comprises pooled individual mononuclear cell populations, and wherein said pooled mononuclear apoptotic cell preparation comprises a decreased percent of non-quiescent non-apoptotic cells;
 a suppressed cellular activation of any living non-apoptotic cells; or
 a reduced proliferation of any living non-apoptotic cells;
 or any combination thereof.

In a related aspect, said pooled individual mononuclear cell populations comprise individual mononuclear cell populations pooled prior to induction of apoptosis or post induction of apoptosis of said individual mononuclear cell populations. In another aspect, the pooled individual mononuclear cell populations comprise populations pooled independent of HLA matching of said individual mononuclear cell populations' HLA markers. In another aspect, the pooled mononuclear apoptotic cell preparation obtained comprises mononuclear cell populations obtained from cells present in between about 2 and 25 units of blood. In another aspect, the blood comprises white blood cell (WBC) fractions from blood donations. In another aspect, the individual mononuclear cell populations comprise at least one cell type selected from the group consisting of: lymphocytes, monocytes, dendritic cells, and natural killer cells. In a further aspect, the individual mononuclear cell populations comprise allogeneic cells from HLA matched or HLA unmatched sources, with respect to a recipient subject.

In a related aspect, the pooled individual mononuclear cell populations comprise cells comprising inactive T cell receptors or reduce immune activity. In another aspect, the pooled individual mononuclear cell populations comprise irradiated cell populations. In another aspect, the irradiation comprises gamma irradiation or UV irradiation. In another aspect, the pooled individual mononuclear cell populations comprise populations pooled prior to said irradiation or post said irradiation. In another aspect, the irradiated cell populations comprise a decreased percent of non-quiescent non-apoptotic cells per population compared with a non-irradiated cell populations.

In one aspect, described herein is a pharmaceutical composition, comprising the cell preparations as disclosed herein.

In one aspect, disclosed herein is a method for producing a pharmaceutical composition comprising a pooled mononuclear apoptotic cell preparation comprising pooled individual mononuclear cell populations in an early apoptotic state, said method comprising the following steps, (a) obtaining individual mononuclear-enriched cell populations of peripheral blood;
 (b) freezing said mononuclear-enriched cell populations in a freezing medium comprising an anticoagulant;
 (c) thawing said mononuclear-enriched cell populations;
 (d) incubating said mononuclear-enriched cell populations in an apoptosis inducing incubation medium comprising methylprednisolone at a final concentration of about 10-100 µg/mL and an anticoagulant;
 (e) resuspending said apoptotic cell populations in an administration medium; and
 (f) inactivating said mononuclear-enriched populations, wherein said inactivation occurs following any step (a) through (e); and
 (g) pooling said mononuclear enriched populations, wherein said pooling occurs following any step (a) through (f);

wherein said method produces a pharmaceutical composition comprising a pooled mononuclear apoptotic cell preparation comprising pooled individual mononuclear cell populations in an early apoptotic state.

In a related aspect, the inactivating step comprises decreasing the percent of non-quiescent non-apoptotic cells, suppressing cellular activation of any living non-apoptotic cells, or reducing the proliferation of any living non-apoptotic cells, or any combination thereof within said pooled mononuclear apoptotic cell preparation. In another aspect, obtaining said individual mononuclear-enriched cell populations comprises obtaining white blood cell (WBC) fractions from multiple individual donors by leukapheresis. In another aspect, the white blood cell (WBC) fractions comprise WBC fractions obtained from a blood bank. In another aspect, the white blood cell (WBC) fractions comprises at least one cell type selected from the group consisting of lymphocytes, monocytes, dendritic cells, and natural killer cells. In another aspect, the white blood cell (WBC) fractions were collected from about 2 to 25 units of blood. In another aspect, the obtaining of said mononuclear-enriched cell populations is not restricted by HLA matching said individual mononuclear-enriched cell populations. In another aspect, the incubating is for about 2-12 hours. In another aspect, the individual mononuclear-enriched cell populations comprise allogeneic cells from HLA-matched or HLA-unmatched sources with respect to a recipient subject.

In a related aspect, the step (I) inactivating said mononuclear-enriched populations comprises suppressing or eliminating an immune response in said individual populations, suppressing or eliminating cross-reactivity between said individual populations, or reducing or eliminating T-cell receptor activity in said individual populations, and wherein said produced pharmaceutical composition comprising said pooled mononuclear apoptotic cell preparation comprises a decreased the percent of living non-apoptotic cells, a suppress cellular activation of any living non-apoptotic cells, or a reduced proliferation of any living non-apoptotic cells, or any combination thereof within said cell preparation. In another aspect, the inactivating said mononuclear-enriched populations comprise irradiating said mononuclear-enriched populations. In another aspect, the irradiation comprises gamma irradiation or UV irradiation. In another aspect, the irradiation comprises about 25-30 Grey units (Gy).

In one aspect, disclosed herein is a method of treating, preventing, ameliorating, inhibiting, or reducing the incidence of an immune disease, an autoimmune disease, a cytokine release syndrome (CRS), a cytokine storm, or an inflammatory disease in a subject in need thereof, comprising administering to the subject a pharmaceutical composition comprising a pooled mononuclear apoptotic cell preparation as described herein, or the composition described herein, or a composition prepared by the method described herein. In one aspect, the immune disease is selected from the group comprising GVHD, arthritis, gout, or inflammatory bowel disease. In another aspect, the subject is suffering from a hematopoietic malignancy, retains a graft-versus-tumor or graft-versus-leukemia (GVL) effect, is undergoing hematopoietic stem-cell transplantation (HSCT), or is undergoing solid organ transplantation. In another aspect, the HSCT is allogeneic HSCT and said pharmaceutical composition comprises cells obtained from multiple allogeneic donors not HLA matched to said subject or to said donor. In another aspect, the administering of the pharmaceutical composition is carried out up to 24 hours prior to said transplantation, at the same time as the transplantation, or is administered until 15 days following said transplantation. In a further aspect, the pharmaceutical composition is administered by intravenous injection.

BRIEF DESCRIPTION OF THE DRAWINGS

The subject matter regarded as disclosed herein is particularly pointed out and distinctly claimed in the concluding portion of the specification. However, the organization and methods of operation, together with objects, features, and advantages thereof, may best be understood by reference to the following detailed description when read with the accompanying drawings in which:

FIGS. 4A-B present the results of a potency test that shows the inhibition of maturation of dendritic cells (DCs) following interaction with apoptotic cells, measured by expression of HLA-DR. FIG. 4A. HLA DR mean fluorescence of fresh final product A (t0). FIG. 4B. HLA DR mean fluorescence of final product A, following 24 h at 2-8° C.

FIG. 5A. CD86 Mean fluorescence of fresh final product A (t0). FIG. 5B. CD86 Mean fluorescence of final product A, following 24 h at 2-8° C.

Figure 1:
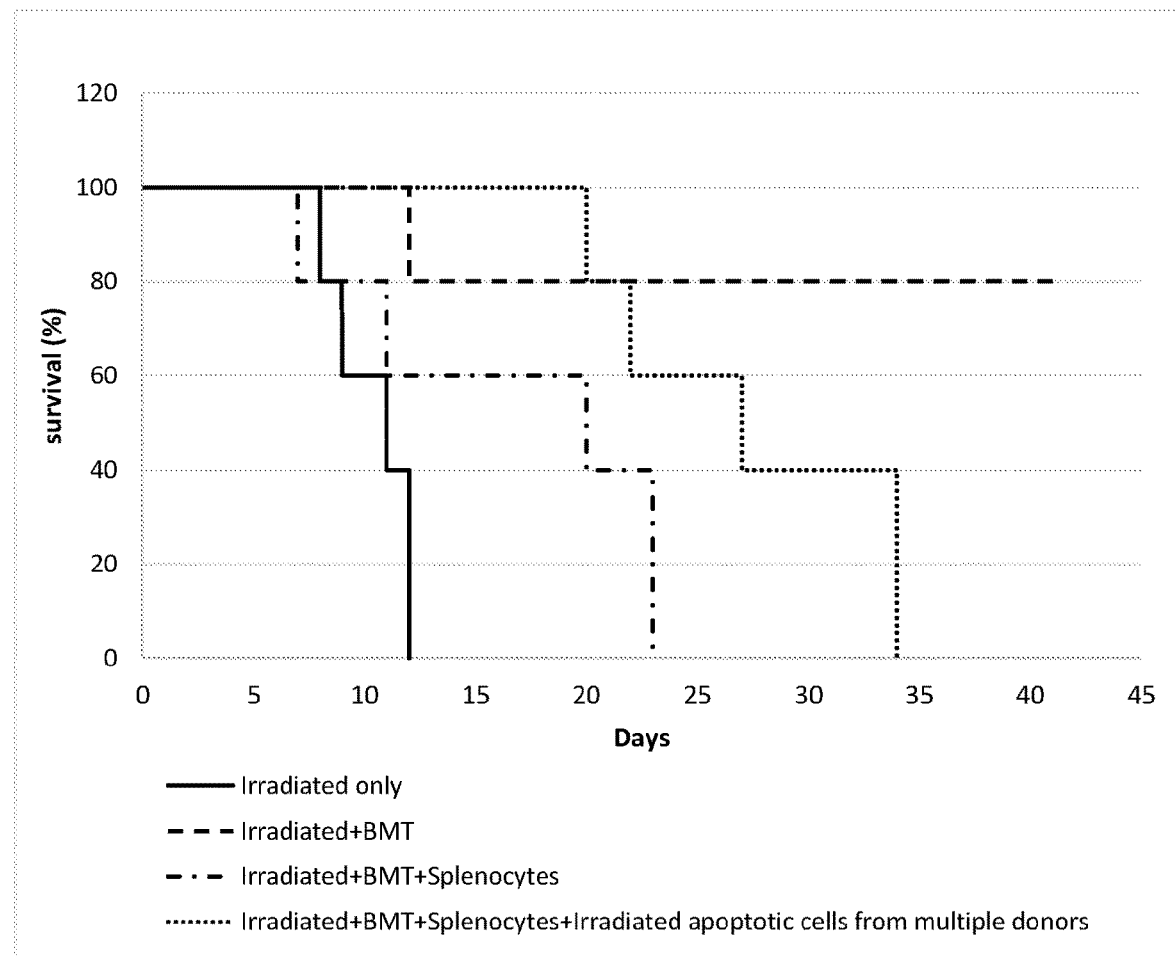
FIG. 1 presents a graph showing the clear effect ($p<0.01$) of a single apoptotic cell preparation injection from multiple individual donors (blue) on survival. The graph presented is a Kaplan-Meier survival curve in a GvHD mouse model that was treated with a single dose irradiated pooled apoptotic cell preparation from multiple individual donors.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

This application claims the benefit of U.S. Patent Provisional Application No. 62/150,305, filed Apr. 21, 2015.

In the following detailed description, numerous specific details are set forth in order to provide a thorough understanding of the disclosure herein. However, it will be understood by those skilled in the art that the cell preparations, methods of making the cell preparations and methods of using these cell preparations may be practiced without these specific details. In other instances, well-known methods, procedures, and components have not been described in detail so as not to obscure the disclosure presented herein.

This disclosure provides in one embodiment, a pooled mononuclear apoptotic cell preparation comprising mononuclear cells in an early apoptotic state, wherein said pooled mononuclear apoptotic cells preparation comprises pooled individual mononuclear cell populations, and wherein said pooled mononuclear apoptotic cell preparation comprises a decreased percent of living non-apoptotic cells, a suppressed cellular activation of any living non-apoptotic cells, or a reduced proliferation of any living non-apoptotic cells, or any combination thereof. In another embodiment, the pooled mononuclear apoptotic cells have been irradiated. In another embodiment, this disclosure provides a pooled mononuclear apoptotic cell preparation that in some embodiments, uses the white blood cell fraction (WBC) obtained from donated blood. Often this WBC fraction is discarded at blood banks or is targeted for use in research.

In one embodiment, the cell preparation is inactivated. In another embodiment, inactivation comprises irradiation. In another embodiment, inactivation comprises T-cell receptor inactivation. In another embodiment, inactivation comprises T-cell receptor editing. In another embodiment, inactivation comprises suppressing or eliminating an immune response in said preparation. In another embodiment, inactivation comprises suppressing or eliminating cross-reactivity between multiple individual populations comprised in the preparation. In other embodiment, inactivation comprises reducing or eliminating T-cell receptor activity between multiple individual populations comprised in the preparation. In another embodiment, an inactivated cell preparation comprises a decreased percent of living non-apoptotic cells, suppressed cellular activation of any living non-apoptotic cells, or a reduce proliferation of any living non-apoptotic cells, or any combination thereof. In another embodiment, an inactivated cell preparation comprises a reduced number of non-quiescent non-apoptotic cells compared with a non-radiated cell preparation.

In another embodiment, the irradiation comprises gamma irradiation or UV irradiation. In yet another embodiment, the irradiated preparation has a reduced number of non-quiescent non-apoptotic cells compared with a non-irradiated cell preparation.

In another embodiment, the pooled mononuclear apoptotic cells have undergone T-cell receptor inactivation. In another embodiment, the pooled mononuclear apoptotic cells have undergone T-cell receptor editing.

In one embodiment, pooled blood comprises $3^{rd}$ party blood from HLA matched or HLA unmatched sources, with respect to a recipient.

In one embodiment, this disclosure provides methods of production of a pharmaceutical composition comprising a pooled mononuclear apoptotic cell preparation comprising pooled individual mononuclear cell populations in an early apoptotic state, wherein said composition comprises a decreased percent of living non-apoptotic cells, a preparation having a suppressed cellular activation of any living non-apoptotic cells, or a preparation having reduced proliferation of any living non-apoptotic cells, or any combination thereof. In another embodiment, the methods provide a pharmaceutical composition comprising a pooled mononuclear apoptotic cell preparation comprising pooled individual mononuclear cell populations in an early apoptotic state, wherein said composition comprises a decreased percent of non-quiescent non-apoptotic cells.

In another embodiment, this disclosure provides methods of use of a pooled mononuclear apoptotic cell preparation comprising mononuclear cells in an early apoptotic state, as described herein, for treating, preventing, ameliorating, inhibiting, or reducing the incidence of an immune disease, an autoimmune disease, an inflammatory disease, a cytokine release syndrome (CRS), a cytokine storm, or infertility in a subject in need thereof. In another embodiment, disclosed herein is a pooled mononuclear apoptotic cell preparation, wherein use of such a cell preparation in certain embodiments does not require matching donors and recipients, for example by HLA typing.

Pooled Mononuclear Apoptotic Cell Preparation

In one embodiment, this disclosure provides a pooled mononuclear apoptotic cell preparation comprising mononuclear cells in an early-apoptotic state, wherein said pooled mononuclear apoptotic cell preparation comprises pooled individual mononuclear cell populations, and wherein said pooled mononuclear apoptotic cell preparation comprises
 a decreased percent of non-quiescent non-apoptotic cells;
 a suppressed cellular activation of any living non-apoptotic cells; or
 a reduced proliferation of any living non-apoptotic cells;
or any combination thereof.

In another embodiment, a pooled mononuclear apoptotic cell preparation comprising mononuclear cells in an early-apoptotic state, wherein said pooled mononuclear apoptotic cell preparation comprises pooled individual mononuclear cell populations, and wherein said pooled mononuclear apoptotic cell preparation comprises a reduced number of non-quiescent non-apoptotic cells.

A skilled artisan would appreciate that the term "pooled" encompasses, in one embodiment, blood collected from multiple individual donors, prepared and possibly stored for later use, wherein mononuclear-enriched cell populations obtained from the blood of the multiple individual donors are combined, for example, following or concurrent with any step of preparation after obtaining individual mononuclear-enriched cells populations of peripheral blood. Alternatively, in another embodiment, pooling occurs following or concurrent with freezing said mononuclear-enriched cell populations. In another embodiment, pooling occurs following or concurrent with thawing said mononuclear-enriched cell population. In another embodiment, pooling occurs following or concurrent with incubation to induce apoptosis. In yet another embodiment, pooling occurs following or concurrent with resuspending the apoptotic population of cells. In another embodiment, pooling occurs following or concurrent with a step inactivation the mononuclear cell population.

Processing of the combined pool of mononuclear-enriched cell populations may then be continued to produce a pooled mononuclear apoptotic cell preparation as described herein.

In an another embodiment, the skill artisan would recognize that the term "pooled" encompasses blood collected from individual donors, prepared individually as apoptotic cell preparations and possibly stored, wherein said preparations are "pooled" at the time of resuspension of the apoptotic preparations. In another embodiment, preparation of blood collected from individual donors is simultaneous and in parallel. In another embodiment, preparation of blood collected from individual donors is not simultaneous.

In another embodiment, cells are pooled just prior to the incubation step described in the methods of preparation below, wherein apoptosis is induced. In another embodiment, cells are pooled following the incubation step at the step of resuspension, as described in the methods of preparation below. In another embodiment, cells are pooled just prior to an irradiation step. In another embodiment, cells are pooled following an inactivation step. In another embodiment, cells are pooled following an irradiation step. In another embodiment, cells are pooled at any step described in the methods of preparation below. In yet another embodiment, a pooled mononuclear apoptotic cell preparation as described herein comprises individual mononuclear cell populations pooled prior to induction of apoptosis or post induction of apoptosis of said individual mononuclear cell populations.

In another embodiment, a pooled mononuclear apoptotic cell preparation ensures that a readily available supply of mononuclear apoptotic cells may be available for use treating, preventing, ameliorating, inhibiting, or reducing the incidence of an immune disease, an autoimmune disease, an inflammatory disease, a cytokine release syndrome (CRS), or a cytokine storm in a subject In one embodiment, a pooled apoptotic cell preparation is obtained from cells present in between about 2 and 25 units of blood. In another embodiment, said pooled apoptotic cell preparation is comprised of cells present in between about 2-5, 2-10, 2-15, 2-20, 5-10, 5-15, 5-20, 5-25, 10-15, 10-20, 10-25, 6-13, or 6-25 units of blood. In another embodiment, said pooled apoptotic cell preparation is comprised of cells present in about 2, 3, 4, 5, 6, 7, 8, 9, 10, 11, 12, 13, 14, 15, 16, 17, 18, 19, 20, 21, 22, 23, 24 or 25 units of blood. The number of units of blood needed is also dependent upon the efficiency of WBC recovery from blood. For example, low efficiency WBC recovery would lead to additional units needed verses high efficiency WBC recovery would lead to fewer units needed. In some embodiments, each unit is a bag of blood. In another embodiment, a pooled apoptotic cell preparation is comprised of cells present in at least 25 units of blood, at least 50 units of blood, or at least 100 units of blood.

In one embodiment, the units of blood comprise white blood cell (WBC) fractions from blood donations. In another embodiment, the donations may be from a blood center or blood bank. In another embodiment, the donations may be from donors in a hospital gathered at the time of preparation of the pooled apoptotic cell preparation. In another embodiment, units of blood comprising WBC from multiple individual donors are saved and maintained in an independent blood bank created for the purpose as disclosed herein. In another embodiment, a blood bank developed for the purpose as disclosed herein to be able to supply units of blood comprising WBC from multiple individual donors comprises a leukapheresis unit.

In one embodiment, the units of WBC pooled are not restricted by HLA matching. Therefore, the resultant pooled apoptotic cell preparation comprises cell populations not restricted by HLA matching. Accordingly, in certain embodiments a pooled mononuclear apoptotic cell preparation comprises allogeneic cells.

While haplotype-matching of human subjects is routinely practiced in the art in the context of therapeutic transplantation, and usually involves matching of HLA-A, HLA-B, and HLA-DR alleles, an advantage of a pooled mononuclear apoptotic cell preparation as disclosed herein, which is obtained from pooled WBC not restricted by HLA matching, is a readily available source of WBC and reduced costs of obtaining WBC.

In one embodiment, pooled blood comprises blood from multiple individual donors independent of HLA matching. In another embodiment, pooled blood comprises blood from multiple individual donors wherein HLA matching with the recipient has been taken into consideration. For example, wherein 1 HLA allele, 2 HLA alleles, 3 HLA alleles, 4 HLA alleles, 5 HLA alleles, 6 HLA alleles, or 7 HLA alleles have been matched between donors and recipient. In another embodiment, multiple individual donors are partially matched, for example some of the donors have been HLA matched wherein 1 HLA allele, 2 HLA alleles, 3 HLA alleles, 4 HLA alleles, 5 HLA alleles, 6 HLA alleles, or 7 HLA alleles have been matched between some of the donors and recipient. as disclosed herein In one embodiment, a cell preparation described herein, comprising pooled individual mononuclear cell populations comprises populations pooled independent of any HLA matching of the individual mononuclear cell populations' HLA markers. In another embodiment, a cell preparation as disclosed herein comprising pooled individual mononuclear cell populations comprises allogenic cells from HLA matched or HLA unmatched sources, with respect to a recipient subject.

One question addressed in the Examples below is the response of laboratory animals (for example a murine model of GvHD) to a pooled mononuclear apoptotic cell preparation as disclosed herein. In certain embodiments, some viable non-apoptotic cells (possibly apoptosis resistant cells) may remain following the induction of apoptosis step described below.

In one embodiment viable non-apoptotic cells comprise live cells, which are Annexin V negative and Propidium Iodide negative. One skilled in the art would appreciate that the term "viable non-apoptotic cells" may be used interchangeably with "non-quiescent non-apoptotic cells". Thus, the skilled artisan would appreciate that non-quiescent non-apoptotic cells are Annexin V negative and Propidium Iodide negative.

These viable non-apoptotic cells may be able to proliferate or being activated. In the case of transplantation, the cells of a pooled mononuclear apoptotic cell preparation may be administered along with the new transplant. In some embodiment, the pooled mononuclear apoptotic cell preparation obtained from multiple individual donors may be activated against the host and in addition may be activation against one another. In certain embodiments, around 10-20% of viable non-apoptotic cells administered may become engrafted and functional.

In one embodiment, a pooled mononuclear apoptotic cell preparation as disclosed herein, comprises an inactivated cell preparation. In another embodiment, an inactivated cell preparation comprises cells comprising inactive T-cell receptors. In another embodiment, an inactivated cell preparation comprises cells comprising a reduced immune response. In another embodiment, an inactivated cell preparation comprises cells comprising inactive T-cell receptors or reduced immune response. In another embodiment, an inactivated cell preparation comprises multiple individual mononuclear populations with suppressed or eliminated cross-reactivity between said populations. In another embodiment, an inactivated cell preparation comprises multiple individual mononuclear populations with reduced or eliminated T-cell receptor activity. In another embodiment, an inactivated cell preparation comprises a reduced number of quiescent non-apoptotic cells. In another embodiment, an inactivated cell preparation comprises a reduced or eliminated immune response. In another embodiment, an inactivated cell preparation comprises pooled individual mononuclear populations with reduced or eliminated cross-reactivity one for another. In another embodiment, an inactivated cell preparation comprising pooled individual mononuclear cell populations comprises irradiated cell populations.

In one embodiment, an irradiated cell preparation or population of cells, as disclosed herein, has suppressed cellular activation and reduced proliferation compared with a non-irradiated cell preparation or population. In another embodiment, the irradiation comprises gamma irradiation or UV irradiation. In another embodiment, an irradiated cell preparation or population has a decreased percent of non-quiescent non-apoptotic cells compared with a non-irradiated cell preparation. In another embodiment, an irradiated cell preparation or population has a reduced number of non-quiescent non-apoptotic cells compared with a non-irradiated cell preparation. In another embodiment, an irradiated cell preparation comprises pooled individual mononuclear populations with reduced or eliminated cross-reactivity one for another.

In another embodiment, the irradiation comprises about 15 Grey units (Gy). In another aspect, the irradiation comprises about 20 Grey units (Gy). In another aspect, the irradiation comprises about 25 Grey units (Gy). In another aspect, the irradiation comprises about 30 Grey units (Gy). In another aspect, the irradiation comprises about 35 Grey units (Gy). In another aspect, the irradiation comprises about 40 Grey units (Gy). In another aspect, the irradiation comprises about 45 Grey units (Gy). In another aspect, the irradiation comprises about 50 Grey units (Gy). In another aspect, the irradiation comprises about 55 Grey units (Gy). In another aspect, the irradiation comprises about 60 Grey units (Gy). In another aspect, the irradiation comprises about 65 Grey units (Gy). In another embodiment, irradiation comprises up to 2500 Gy. In another embodiment, the irradiation comprises about 15-25 Grey units (Gy). In another embodiment, the irradiation comprises about 25-30 Grey units (Gy). In another embodiment, the irradiation comprises about 30-40 Grey units (Gy). In another embodiment, the irradiation comprises about 40-50 Grey units (Gy). In another embodiment, the irradiation comprises about 50-65 Grey units (Gy).

In another embodiment, an irradiated pooled apoptotic cell preparation maintains a same or similar apoptotic profile, stability and efficacy as a non-irradiated pooled apoptotic cell preparation. In another embodiment, an irradiated pooled apoptotic cell preparation maintains a same or similar cell type distribution profile.

In still another embodiment, a pooled mononuclear apoptotic cell preparation as described herein comprises individual mononuclear cell populations pooled prior to inactivation or post inactivation of said individual mononuclear cell populations. In another embodiment, a pooled mononuclear apoptotic cell preparation as described herein comprises individual mononuclear cell populations pooled prior to irradiation or post irradiation of said individual mononuclear cell populations.

In one embodiment, a pooled mononuclear apoptotic cell preparation as disclosed herein is stable for up to 24 hours. In another embodiment, a pooled mononuclear apoptotic cell preparation is stable for at least 24 hours. In another embodiment, a pooled mononuclear apoptotic cell preparation is stable for more than 24 hours. In yet another embodiment, a pooled mononuclear apoptotic cell preparation as disclosed herein is stable for up to 36 hours. In still another embodiment, a pooled mononuclear apoptotic cell preparation is stable for at least 36 hours. In a further embodiment, a pooled mononuclear apoptotic cell preparation is stable for more than 36 hours. In another embodiment, a pooled mononuclear apoptotic cell preparation as disclosed herein is stable for up to 48 hours. In another embodiment, a pooled mononuclear apoptotic cell preparation is stable for at least 48 hours. In another embodiment, a pooled mononuclear apoptotic cell preparation is stable for more than 48 hours.

A skilled artisan would appreciate that the term "stable" encompasses a preparation wherein the percent (%) of early apoptotic cell is not reduced following inactivation, for example in one embodiment, following irradiation. In one embodiment, the percent (%) of early apoptotic cells in a cell preparation as disclosed herein is not reduced by more than about 1%. In another embodiment, the percent (%) of early apoptotic cells in a cell preparation as disclosed herein is not reduced by more than about 2%. In another embodiment, the percent (%) of early apoptotic cells in a cell preparation as disclosed herein is not reduced by more than about 3%. In another embodiment, the percent (%) of early apoptotic cells in a cell preparation as disclosed herein is not reduced by more than about 4%. In another embodiment, the percent (%) of early apoptotic cells in a cell preparation as disclosed herein is not reduced by more than about 5%. In another embodiment, the percent (%) of early apoptotic cells in a cell preparation as disclosed herein is not reduced by more than about 6%. In another embodiment, the percent (%) of early apoptotic cells in a cell preparation as disclosed herein is not reduced by more than about 7%. In another embodiment, the percent (%) of early apoptotic cells in a cell preparation as disclosed herein is not reduced by more than about 8%. In another embodiment, the percent (%) of early apoptotic cells in a cell preparation as disclosed herein is not reduced by more than about 9%. In another embodiment, the percent (%) of early apoptotic cells in a cell preparation as disclosed herein is not reduced by more than about 10%. In another embodiment, the percent (%) of early apoptotic cells in a cell preparation as disclosed herein is not reduced by more than about 20%.

In one embodiment, methods of producing the pooled cell preparation comprising an irradiation step preserves the early apoptotic, immune modulation, and stability properties observed in an apoptotic preparation obtained from a single match donor wherein the cell preparation may not include an irradiation step. In another embodiment, a pooled mononuclear apoptotic cell preparation as disclosed herein does not elicit a graft versus host disease (GVHD) response Irradiation of the cell preparation is considered safe in the art. Irradiation procedures are currently performed on a routine basis to donated blood to prevent reactions to WBC.

In another embodiment, the percent of apoptotic cells in a pooled mononuclear apoptotic cell preparation as disclosed herein is close to 100%, thereby reducing the fraction of living non-apoptotic cells in the cell preparation. In one embodiment, the percent of apoptotic cells is at least 20%. In another embodiment, the percent of apoptotic cells is at least 30%. In another embodiment, the percent of apoptotic cells is at least 40%. In another embodiment, the percent of apoptotic cells is at least 50%. In yet another embodiment, the percent of apoptotic cells is at least 60%. In still another embodiment, the percent of apoptotic cells is at least 70%. In a further embodiment, the percent of apoptotic cells is at least 80%. In another embodiment, the percent of apoptotic cells is at least 90%. In yet another embodiment, the percent of apoptotic cells is at least 99%. Accordingly, a cell preparation comprising a reduced or non-existent or quiescent or non-activatable fraction of living non-apoptotic cells may in one embodiment provide a pooled mononuclear apoptotic cell preparation that does not elicit GVHD in a recipient.

Alternatively, in another embodiment, the percentage of living non-apoptotic WBC is reduced by specifically removing the living cell population, for example by targeted precipitation In another embodiment, the percent of living non-apoptotic cells may be reduced using magnetic beads that bind to phosphatidylserine. In another embodiment, the percent of living non-apoptotic cells may be reduced using magnetic beads that bind a marker on the cell surface of non-apoptotic cells but not apoptotic cells. Or vice versa, the apoptotic cells may be selected for further preparation using magnetic beads that bind to a marker on the cell surface of apoptotic cells but not non-apoptotic cells. In yet another embodiment, the percentage of living non-apoptotic WBC is reduced by the use of ultrasound.

In one embodiment the apoptotic cells are from pooled third party donors. In another embodiment the apoptotic cells are from pooled fourth party donors. In another embodiment the apoptotic cells are from pooled fifth party donors. In another embodiment the apoptotic cells are from pooled N-party donors, wherein N represents the number of sources in a given pooled cell preparation, for example individual donors or individual units of blood. For example, if a pooled cell preparation comprises mononuclear cells from ten (10) individual source donors, N is 10.

In one embodiment, a pooled cell preparation comprises at least one cell type selected from the group consisting of: lymphocytes, monocytes, dendritic cells, and natural killer cells. In another embodiment, a pooled cell preparation comprises an enriched population of mononuclear cells. In one embodiment, a pooled mononuclear is a mononuclear enriched cell preparation comprises cell types selected from the group consisting of: lymphocytes, monocytes, dendritic cells, and natural killer cells. In another embodiment, the mononuclear enriched cell preparation comprises no more than 15%, alternatively no more than 10%, typically no more than 5% polymorphonuclear leukocytes, also known as granulocytes (i.e., neutrophils, basophils and eosinophils). In another embodiment, a pooled mononuclear cell preparation is devoid of granulocytes.

In another embodiment, the pooled mononuclear enriched cell preparation comprises no more than 15%, alternatively no more than 10%, typically no more than 5% $CD15^{high}$ expressing cells. In one embodiment, a pooled apoptotic cell preparation comprises less than 15% CD15 high expressing cells.

In one embodiment, the pooled mononuclear enriched cell preparation comprises at least 60% mononuclear cells, at least 70%, at least 80%, at least 85% mononuclear cells, alternatively at least 90% mononuclear cells, or at least 95% mononuclear cells, wherein each possibility is a separate embodiment. In one embodiment, the pooled mononuclear enriched cell preparation comprises at least 85% mononuclear cells.

In one embodiment, a pooled mononuclear apoptotic cell preparation comprises pooling cell preparations having increased polynuclear cells (PMN) with cell preparation having high mononuclear cells.

One of ordinary skill in the art would appreciate that the term "mononuclear cells" may encompass leukocytes having a one lobed nucleus. In another embodiment, a pooled apoptotic cell preparation as disclosed herein comprises less than 5% polymorphonuclear leukocytes.

Pharmaceutical Compositions and Preparation Thereof

Methods for preparing apoptotic cells from single matched donors and uses thereof have been described in detail in International Publication No. WO 2014/087408—for example see Examples 11-15, and in International Application No. PCT/IL2016/050194—for example see Examples 1-2, which are hereby incorporated herein in their entirety.

A skilled artisan would appreciate that the terms "composition" and "pharmaceutical composition", as disclosed herein are used interchangeably having all the same meanings and qualities, and encompass in one embodiment, a composition comprising the pooled mononuclear apoptotic cell preparation as described in detail above. In one embodiment, the pharmaceutical composition encompasses a composition comprising the pooled cell preparation disclosed herein, and further comprises an anticoagulant. The skilled artisan would appreciate that the term "composition" may encompass a composition comprising the pooled cell preparation as disclosed herein resuspended in a final suspension medium used for administration of the cell preparation to a recipient subject, for example a patient in need. The skilled artisan would further appreciate that the terms "final suspension medium" and "administration medium", as used herein, are used interchangeably and may encompass the medium used for administration of the pooled cell preparation disclosed herein to a recipient subject.

In one embodiment, a pharmaceutical composition as disclosed herein comprises a pooled mononuclear apoptotic cell preparation comprising mononuclear cells in an early-apoptotic state, wherein said pooled mononuclear apoptotic cell preparation comprises pooled individual mononuclear cell populations, and wherein said pooled mononuclear apoptotic cell preparation comprises a decreased percent of living non-apoptotic cells; a suppressed cellular activation of any living non-apoptotic cells; or a reduced proliferation of any living non-apoptotic cells; or any combination thereof. In another embodiment, a pharmaceutical composition comprises a pooled mononuclear apoptotic cell preparation disclosed herein.

In another embodiment, in a composition said pooled mononuclear apoptotic cell preparation comprises an inactivation preparation as disclosed herein, for example an irradiated preparation or a preparation wherein said individual cell populations have been irradiated. In another embodiment, a composition further comprises an anti-coagulant.

In one embodiment, disclosed herein is a method for producing a pharmaceutical composition comprising a pooled mononuclear apoptotic cell preparation comprising pooled individual mononuclear cell populations in an early apoptotic state, said method comprising the following steps,
(a) obtaining individual mononuclear-enriched cell populations of peripheral blood;
(b) freezing said mononuclear-enriched cell populations in a freezing medium comprising an anticoagulant;
(c) thawing said mononuclear-enriched cell populations;
(d) incubating said mononuclear-enriched cell populations in an apoptosis inducing incubation medium comprising methylprednisolone at a final concentration of about 10-100 µg/mL and an anticoagulant;
(e) resuspending said apoptotic cell populations in an administration medium; and
(f) inactivating said mononuclear-enriched populations, wherein said inactivation occurs following any step (a) through (e); and
(g) pooling said mononuclear enriched populations, wherein said pooling occurs following any step (a) through (f);
wherein said method produces a pharmaceutical composition comprising a pooled mononuclear apoptotic cell preparation comprising pooled individual mononuclear cell populations in an early apoptotic state.

In one embodiment, an inactivating step (f) comprises decreasing the percent of non-quiescent non-apoptotic cells, suppressing cellular activation of any living non-apoptotic cells, or reducing the proliferation of any living non-apoptotic cells, or any combination thereof within said pooled mononuclear apoptotic cell preparation.

In one embodiment, obtaining a mononuclear-enriched cell population comprises obtaining white blood cell (WBC) fractions from multiple individual donors by leukapheresis.

In another embodiment, obtaining a mononuclear-enriched cell population comprises obtaining white blood cell (WBC) fractions comprise WBC fractions obtained from a blood bank. In another embodiment, collected WBC may be ready to use based on the source from which they are obtained.

A skilled artisan would appreciate that the term "leukapheresis" may encompass an apheresis procedure in which leukocytes are separated from the blood of a donor. In one embodiment, the blood of a donor undergoes leukapheresis and thus a mononuclear-enriched cell composition is obtained according to the production method. It is to be noted, that the use of at least one anticoagulant during leukapheresis is required, as is known in the art, in order to prevent clotting of the collected cells.

In one embodiment, the leukapheresis procedure is configured to allow collection of mononuclear-enriched cell composition according to the production method. In one embodiment, cell collections obtained by leukapheresis comprise at least 40%, 50%, 60%, 65%, 70%, or 80% mononuclear cells. In one embodiment, blood plasma from the cell-donor is collected in parallel to obtaining of the mononuclear-enriched cell composition according to the production method. In one embodiment, about 300-600 ml of blood plasma from the cell-donor are collected in parallel to obtaining the mononuclear-enriched cell composition according to the production method. In one embodiment, blood plasma collected in parallel to obtaining the mononuclear-enriched cell composition according to the production method is used as part of the freezing and/or incubation medium.

It is to be noted that, In one embodiment, while the mononuclear-enriched cell preparation at cell collection comprises at least 40%, 50%, 60%, 65%, 70%, or at least 80% mononuclear cells, the final pharmaceutical composition, following the production method, comprises at least 70%, 80%, 85%, 90%, or at least 95% mononuclear cells. In another embodiment, the mononuclear-enriched cell preparation at cell collection comprises a lower percent of mononuclear cells than the final product produced using a method as disclosed herein. In another embodiment, the pooled mononuclear apoptotic cell preparation comprises a higher percent of mononuclear cells than the initial mononuclear-enriched cell preparations, for example those preparations collected by leukapheresis.

According to certain embodiments, the mononuclear-enriched cell preparation used for production of the composition comprises at least 50% mononuclear cells at cell collection. In another embodiment, the mononuclear-enriched cell preparation used for production of a composition disclosed herein comprises between about 40-60% mononuclear cells at cell collection. According to certain embodiments, the present disclosure provides a method for producing the pharmaceutical composition wherein the method comprises obtaining a mononuclear-enriched cell preparation from the peripheral blood of a donor, the mononuclear-enriched cell preparation comprising at least 50% mononuclear cells. In another embodiment, a method for producing the pharmaceutical composition wherein the method comprises obtaining a mononuclear-enriched cell preparation from the peripheral blood of a donor, the mononuclear-enriched cell preparation comprising about 40-60% mononuclear cells. According to certain embodiments, the present disclosure provides a method for producing the pharmaceutical composition wherein the method comprises freezing a mononuclear-enriched cell preparation comprising at least 40%, 50%, or 60% mononuclear cells.

In one embodiment, a unit of blood comprises $0.35 \times 10^7$ cells. In another embodiment, between $1 \times 10^6$ and $1 \times 10^7$ cells are obtained. In another embodiment, cells obtained are ready to use in a preparation as disclosed herein. In another embodiment, white blood cell (WBC) fractions are collected from about 2 to 25 units of blood. In another embodiment, white blood cell (WBC) fractions are collected from about 1 to 250 units of blood. In another embodiment, white blood cell (WBC) fractions are collected from about 1 to 500 units of blood. In another embodiment, white blood cell (WBC) fractions are collected from about 1 to 1000 units of blood. In another embodiment, white blood cell (WBC) fractions are collected from about 1 to 2000 units of blood.

In another embodiment, 2-25 units of blood may be collected in a single day for the preparation of a composition herein. In another embodiment, 1-250 units of blood may be collected in a single day for the preparation of a composition herein. In another embodiment, 1-500 units of blood may be collected in a single day for the preparation of a composition herein. In another embodiment, 500-1000 units of blood may be collected in a single day for the preparation of a composition herein. In yet another embodiment, 500-2000 units of blood may be collected in a single day for the preparation of a composition herein. In another embodiment, 1000 units of blood may be collected in a single day for the preparation of a composition herein.

In one embodiment, 350 billion pooled blood cells are obtained for a preparation of a composition described herein. In another embodiment, 100-500 billion pooled blood cells are obtained for a preparation of a composition described herein. In another embodiment, about 100 billion, about 200 billion, about 300 billion, about 400 billion, about 500 billion, about 600 billion, about 700 billion, about 800 billion, or about 900 billion cells are obtained for a preparation of a composition described herein.

In one embodiment, a dosage of a composition described herein comprises 35-70 million pooled mononuclear apoptotic cells per kilo of a subject. Thus, starting with a pool of 350 billion cells, 80-150 dosage units may be prepared at one time. In one embodiment, on average 10 units of pooled blood produces a single therapeutic dose. This calculation is based on current production leukapheresis without taking into consideration possible improvements in production efficiency, etc.

In one embodiment, a composition as disclosed herein may be used for repeated dosing.

In one embodiment, methods of preparation as disclosed herein comprise preparing a pooled mononuclear-enriched cell population comprising white blood cell (WBC) fractions collected from about 2 to 25 units of blood. In another embodiment, white blood cell (WBC) fractions were collected from about 13 to 25 units of blood. In yet another embodiment, white blood cell (WBC) fractions were collected from about 10 units of blood. In another embodiment, said WBC fractions were collected from between about 2-5, 2-10, 2-15, 2-20, 5-10, 5-15, 5-20, 5-25, 10-15, 10-20, 10-25, 6-13, or 6-25 units of blood. In another embodiment, said WBC fractions were collected from about 2, 3, 4, 5, 6, 7, 8, 9, 10, 11, 12, 13, 14, 15, 16, 17, 18, 19, 20, 21, 22, 23, 24 or 25 units of blood. The number of units of blood needed is also dependent upon the efficiency of WBC recovery from blood. For example, low efficiency WBC recovery would lead to additional units needed verses high efficiency WBC recovery would lead to fewer units needed. In some embodiments, each unit is a bag of blood. In another embodiment, a pooled apoptotic cell preparation is comprised of cells present in at least 25 units of blood, at least 50 units of blood, or at least 100 units of blood. In still a further embodiment, preparation of a pooled mononuclear enriched apoptotic cell population comprises as many units of WBC as determined by the skilled artisan performing the preparation.

In one embodiment, methods of producing a composition comprise WBC fraction collected independent of HLA matching. In another embodiment, said WBC fractions are obtained from multiple individual donors by leukapheresis. In another embodiment, white blood cell (WBC) fractions are obtained from a blood bank. In another embodiment, the method of producing a composition disclosed herein comprises obtaining said mononuclear-enriched cells populations not restricted by HLA matching said individual mononuclear enriched cell populations.

In one embodiment, the heparin in a pharmaceutical composition is present at a concentration between 0.001 U/ml and 3 U/ml, typically between 0.01 ml and 2.5 U/ml. In another embodiment, the heparin in the pharmaceutical compositions is present at a concentration between 0.005 U/ml and 2.5 U/ml. According to other embodiments, the heparin in the pharmaceutical composition is present at a concentration between 0.01 U/ml and 1 U/ml. In one embodiment, the ACD Formula A in the pharmaceutical composition is present at a concentration of 0.01%-6% v/v. According to other embodiments, the ACD Formula A in the pharmaceutical composition is present at a concentration of 0.05%-5% v/v. According to other embodiments, the ACD Formula A in the pharmaceutical composition is present at a concentration of 0.01%-10% v/v. Further, compositions comprising mononuclear apoptotic cells and preparation of same have been described in WO 2014/087408, which is incorporated herein in full.

In one embodiment, the pharmaceutical compositions further comprise residual methylprednisolone. In one embodiment, the pharmaceutical composition further comprises methylprednisolone at a concentration that does not exceed 30 μg/ml. In one embodiment, the pharmaceutical composition further comprises an anti-coagulant. In one embodiment, the anti-coagulant is selected from the group consisting of: heparin, ACD Formula A and a combination thereof.

It should be appreciated that, In one embodiment, the high percentage of mononuclear cells in the cell preparation disclosed herein is achieved following the multistep manufacturing protocol, as described herein (including leukapheresis and pooling of blood units, early-apoptosis induction using cryopreservation and incubation with methylprednisolone and various washing steps).

A skilled artisan would appreciate that the term "early apoptosis" refers in one embodiment to an apoptotic population of cells wherein at least 85% of the cells remain viable (Annexin V positive) and less than 15% are considered dead or dying by a propidium iodide (PI) assay (PI negative. In another embodiment, "early apoptosis" refers to a cell population wherein at least 85% of the cells remain viable and less than 15% of the cells express $CD15^{high}$.

A skilled artisan would appreciate that the term "early-apoptotic state" may encompass cells that show early signs of apoptosis without late signs of apoptosis. Examples of early signs of apoptosis in cells include exposure of phosphatidylserine (PS) and the loss of mitochondrial membrane potential. Examples of late events include propidium iodide (PI) admission into the cell and the final DNA cutting. In order to document that cells are in an "early apoptotic" state, in one embodiment, PS exposure detection by Annexin-V and PI staining are used, and cells that are stained with Annexin V but not with PI are considered to be "early apoptotic cells". In another embodiment, cells that are stained by both Annexin-V FITC and PI are considered to be "late apoptotic cells". In another embodiment, cells that do not stain for either Annexin-V or PI are considered non-apoptotic viable cells (live cells).

In one embodiment, apoptotic cells comprise cells in an early apoptotic state. In another embodiment, apoptotic cells comprise cells wherein at least 90% of said cells are in an early apoptotic state. In another embodiment, apoptotic cells comprise cells wherein at least 80% of said cells are in an early apoptotic state. In another embodiment, apoptotic cells comprise cells wherein at least 70% of said cells are in an early apoptotic state. In another embodiment, apoptotic cells comprise cells wherein at least 60% of said cells are in an early apoptotic state. In another embodiment, apoptotic cells comprise cells wherein at least 50% of said cells are in an early apoptotic state. In another embodiment, apoptotic cells comprise cells wherein at least 40% of said cells are in an early apoptotic state.

In one embodiment, methods of producing a pooled mononuclear apoptotic cell preparation, comprise a white blood cell (WBC) fraction comprising at least one cell type selected from the group consisting of lymphocytes, monocytes, dendritic cells, and natural killer cells.

In one embodiment, the mononuclear-enriched cell preparation comprises low concentrations of non-mononuclear leukocytes such as, but not limited to, polymorphonuclear leukocytes and neutrophils. In one embodiment, pooled mononuclear enriched cell preparations are devoid of granulocytes. In one embodiment, granulocytes disintegrate during various steps of the production method. In one embodiment, the composition comprises no more than 15%, alternatively no more than 10%, typically no more than 5% granulocytes.

In one embodiment, granulocytes disintegrate to a significant degree following the freezing and thawing steps of the production method. In one embodiment, granulocytes disintegrate to a significant degree following the freezing and thawing steps of the production method, and are washed from the preparation during wash steps after the freezing and/or thawing steps.

In one embodiment, disintegrated granulocytes are washed from the cell preparation during various washing steps of the production method. In one embodiment, the composition comprises no more than 15%, possibly no more than 10%, typically no more than 5% polymorphonuclear leukocytes.

In one embodiment, the composition comprises no more than 5% polymorphonuclear leukocytes. In one embodiment, the composition comprises no more than 15%, alternatively no more than 10%, typically no more than 5% $CD15^{high}$ expressing cells.

In one embodiment, the composition comprises no more than 5% $CD15^{high}$ expressing cells.

A skilled artisan would appreciate that the term "$CD15^{high}$" expressing cells may encompass granulocytes.

An early feature of apoptosis is a morphological change in the plasma membrane. This change involves the translocation of the membrane phospholipid phosphatidylserine (PS) from the internal layer to the external layer of the cell membrane. In the presence of calcium ions, Annexin V has a high specificity and affinity for PS. Thus, the binding of Annexin V to cells with exposed PS provides a very sensitive method for detecting early cellular apoptosis.

Thus, in one embodiment an "early apoptotic state" of a cell or "early apoptotic cells", as used herein, refers to a cell population which still have intact cell membranes, but have started to undergo DNA cleavage and have started to undergo translocation of phosphatidylserine. As used herein, early apoptotic cells, or cells at an early apoptotic state, are cells which are stained positively using Annexin V and are stained negatively with propidium iodide (PI). Methods for detection of early apoptosis are known in the art, such as early apoptotic cell detection of annexin V positive and propidium iodide (PI) negative, by flow cytometry. In one embodiment of a method of producing a composition as disclosed herein, a step of irradiation does not change significantly the early apoptotic phenotype (i.e. % PS positive & PI negative) of a cell preparation.

In one embodiment, cells which are in a late apoptotic state may be detected by a positive staining using annexin V and a positive staining using PI as may be evidenced using flow cytometry. It is to be noted that PI is membrane impermeable and thus is only able to enter cells in which the intactness of the cell membrane has been compromised, such as in late apoptotic or necrotic cells. In one embodiment, necrotic cells show strong staining for PI, as may be evidenced using flow cytometry.

In some embodiments, the cell preparation comprises cells in suspension.

A skilled artisan would appreciate that the term "viability" of the cells may encompass cells not undergoing necrosis, early apoptosis, or late apoptosis. Accordingly, the term "viable cells", as used herein, refers to cells not undergoing necrosis or cells which are not in an early or late apoptotic state. In one embodiment, the term "viable cells" refers to cells having an intact plasma membrane. Assays for determining cell viability are known in the art, such as using propidium iodide (PI) staining which may be detected by flow cytometry. Accordingly, in one embodiment, viable cells are cells which do not show propidium iodide intake and do not express phosphatidylserine. Necrosis can be further identified, by using light, fluorescence or electron microscopy techniques, or via uptake of the dye trypan blue.

Apoptosis, which is a distinct cell death process from necrosis, is the programmed and orderly physiological elimination of cells, occurring, for example, during normal cell and tissue development, T-lymphocyte killing of pathogen-infected cells, and self-elimination of mutationally damaged cells. Apoptotic cells are characterized by distinct morphologic alterations in the cytoplasm and nucleus, chromatin cleavage at regularly spaced sites, and endonucleolytic cleavage of genomic DNA at internucleosomal sites. Assays for determining cell apoptosis are known in the art, such as using AnnexinV. Necrosis, on the other hand, is an inherently pathological and pro-inflammatory process of cell death caused, typically but not exclusively, by the uncontrolled, progressive degradative action of enzymes following lethal cellular injury. Necrotic cells are typically characterized by mitochondrial swelling, nuclear flocculation, cell lysis, loss of membrane integrity, and ultimately cell death.

In one embodiment, the cell preparation comprises at least 50%, 60%, 70%, 80%, 85%, 90%, or 95% viable cells, or at least 97% viable cells.

In additional embodiments, the high percentage of viable cells in the cell preparation remains for at least 24 hours following preparation. In one embodiment, necrotic cells and/or cells in a late apoptotic state disintegrate and are thus substantially eliminated from the final cell-preparation during washing steps of the production method.

In one embodiment as disclosed herein, in order to induce therapeutic immune tolerance in autoimmune diseases, such as GVHD, the therapeutic mononuclear enriched cells in the cell preparation are obtained from an allogeneic individual.

In another embodiment, a pooled mononuclear apoptotic cell preparation prepared using methods disclosed herein, comprise allogeneic cells from HLA-matched or HLA-unmatched sources with respected to a recipient subject. In another embodiment, allogeneic cell comprise HLA-matched sources with respect to the recipient subject. In another embodiment, allogeneic cell comprise HLA-unmatched sources with respect to the recipient subject.

In one embodiment, the pharmaceutical composition comprises the pooled cell preparation and further comprises an anti-coagulant.

A skilled artisan would appreciate that the terms "pooled cell preparation", "cell preparation", "pooled mononuclear apoptotic cell preparation", "mononuclear enriched apoptotic cell preparation", and "mononuclear apoptotic cell preparation" in one embodiment, are used interchangeably having all the same meanings and qualities.

In one embodiment, the pharmaceutical composition comprises the cell preparation and further comprises residual methylprednisolone. According to other embodiments, the pharmaceutical composition comprises the cell preparation and further comprises an anti-coagulant and residual methylprednisolone. In one embodiment, residual methylprednisolone refers to methylprednisolone remaining in the composition following use of the production method.

In one embodiment, the composition comprises an anti-coagulant. As known in the art, an anti-coagulant, as used herein, refers to a substance which prevents or decreases blood clotting. In one embodiment, the anti-coagulant is heparin. According to other embodiments, the anti-coagulant is Acid-Citrate-Dextrose (ACD), formula A. In one embodiment, the anti-coagulant is a composition comprising ACD formula A and heparin. In one embodiment, the anti-coagulant is ACD formula A containing heparin at a concentration of about 10 U/ml. In one embodiment, the anti-coagulant is selected from the group consisting of: heparin, ACD Formula A and a combination thereof. In one embodiment, the presence of an anti-coagulant in the composition is due to addition of the anti-coagulant during the freezing and/or incubation and/or washing stages of the composition's production process. In one embodiment, the presence of an anti-coagulant during production of the composition does not adversely affect apoptosis induction as described herein.

In one embodiment, the composition comprises heparin. In one embodiment, heparin is selected from the group consisting of: sulfated heteropolysaccharide heparin, unfractionated heparin (UFH), low molecular weight heparin (LMWH) and a combination thereof. According to other embodiments, heparin is a synthetic heparin, such as, but not limited to, Fondaparinaux.

In one embodiment, the composition comprises heparin at a concentration between 0.001 U/ml and 3 U/ml, alternatively between 0.005 U/ml and 2.5 U/ml, typically between 0.01 U/ml and 1 U/ml. According to other embodiments, the composition comprises heparin at a concentration between 0.001-2.5 U/ml, alternatively between 0.001-1 U/ml, possibly between 0.001-0.5 U/ml.

According to other embodiments, the composition comprises heparin at a concentration between 0.005-1 U/ml, alternatively between 0.005-0.6 U/ml, possibly between 0.005-0.5 U/ml. According to other embodiments, the composition comprises heparin at a concentration between 0.01-3 U/ml, alternatively between 0.01-2 U/ml or between 0.01-0.6 U/ml. In one embodiment, the composition comprises heparin at a concentration between 0.01-0.5 U/ml. In one embodiment, the composition comprises heparin at a concentration between 0.05 U/ml and 0.25 U/ml. According to certain embodiments, the composition comprises heparin at a concentration between 0.01 U/ml and 0.6 U/ml.

In one embodiment, the composition comprises up to 3 U/ml heparin, typically up to 2.5 U/ml heparin, possibly up to 1 U/ml heparin, alternatively up to 0.5 U/ml heparin. In one embodiment, the composition comprises at least 0.001 U/ml heparin, alternatively at least 0.005 U/ml heparin, possibly at least 0.01 heparin. In one embodiment, the composition comprises up to 300 U, alternatively up to 150 U, possibly up to 75 U of Heparin. According to certain embodiments, the composition comprises up to 180 U of heparin.

In one embodiment, heparin comprised in the composition refers to heparin in the composition comprising the cell preparation and the final suspension medium used for administration of the cell preparation to a patient. In one embodiment, ACD Formula A comprised in the composition refers to heparin in the composition comprising the cell preparation and the final suspension medium used for administration of the cell preparation to a patient.

In one embodiment, the composition comprises between 0.5-500 U of heparin, possibly between 0.5-500 U of heparin, alternatively between 7-180 U of heparin.

In one embodiment, the composition comprises ACD Formula A. In one embodiment, ACD Formula A comprises citric acid, dextrose and sodium citrate. In one embodiment, ACD Formula A comprises anhydrous citric acid at a concentration of 0.73 gr/100 ml, dextrose monohydrate at a concentration of 2.45 gr/100 ml and sodium citrate dehydrate at a concentration of 2.20 gr/100 ml.

In one embodiment, the composition comprises ACD formula A at a concentration between 0.01-10 v/v, alternatively between 0.05-6 v/v, possibly between 0.1%-5% v/v. According to other embodiments, the composition comprises ACD formula A at a concentration between 0.05-10 v/v, possibly 0.05-6 v/v, alternatively between 0.05-5 v/v.

According to alternate embodiments, the composition comprises ACD formula A at a concentration between 0.1-10 v/v, alternatively between 0.1%-6%, possibly between 0.1%-5% v/v. In one embodiment, the composition comprises ACD formula A at a concentration between 0.5%-2.5% v/v. According to certain embodiments, the composition comprises ACD formula A at a concentration between 0.05-6 v/v, typically between 0.1%-6% v/v.

In one embodiment, the composition comprises up to 15 ml, alternatively up to 9 ml, possibly up to 7.5 ml of ACD formula A. According to certain embodiments, the composition comprises up to 18 ml of ACD formula A.

In one embodiment, the composition comprises between 0.05-40 ml of ACD formula A, possibly between 0.1-25 ml of ACD formula A, alternatively between 0.7-18 ml of ACD formula A.

In one embodiment, the composition further comprises methylprednisolone. In one embodiment, the presence of residual methylprednisolone in the composition is due to use of methylprednisolone during the incubation stage of the cell preparations production process. In one embodiment, methylprednisolone is used during production of the cell preparation, as part of the procedure in which the cells are induced to enter an early apoptotic state.

In one embodiment, the composition further comprises methylprednisolone at a concentration between 0.5-30 µg/ml, possibly 1-25 µg/ml, typically between 3-22 µg/ml. In one embodiment, the composition comprises methylprednisolone at a concentration between 3.7-21.9 µg/ml.

In one embodiment, the composition further comprises methylprednisolone at a concentration that does not exceed 30 μg/ml. In one embodiment, the composition further comprises methylprednisolone at a concentration that does not exceed 30 μg/ml, possibly does not exceed 25 μg/ml, typically does not exceed 21.9 μg/ml.

In one embodiment, the composition further comprises methylprednisolone at a concentration between 0.5-60 μg/ml, possibly 1.12-60 μg/ml. In one embodiment, the composition further comprises methylprednisolone at a concentration that does not exceed 60 μg/ml.

In one embodiment, the composition comprises at least 0.5 μg/ml, possibly at least 1 μg/ml, alternatively at least 3 μg/ml methylprednisolone. In one embodiment, the composition comprises at least 3.5 μg/ml methylprednisolone. In one embodiment, the composition comprises at least 3.7 μg/ml methylprednisolone.

In one embodiment, the composition further comprises between 0.1-25 mg methylprednisolone, possibly between 0.4-20 mg methylprednisolone, alternatively between 0.67-18 mg methylprednisolone. In one embodiment, the composition further comprises methylprednisolone in an amount that does not exceed 25 mg, typically 20 mg, alternatively 18 mg. According to certain embodiments, the composition further comprises methylprednisolone in an amount that does not exceed 15 mg.

In one embodiment, the heparin in the pharmaceutical composition is present at a concentration between 0.005 U/ml and 2.5 U/ml. According to other embodiments, the ACD Formula A in the pharmaceutical composition is present at a concentration of 0.01%-10% v/v, alternatively 0.05%-5% v/v.

In particular embodiments, the pharmaceutical composition is administered at a dosage of about $30 \times 10^6$-$300 \times 10^6$ cells per kg body weight, $100 \times 10^6$-$300 \times 10^6$ cells per kg body weight, alternatively about $120 \times 10^6$-$250 \times 10^6$ cells per kg body weight. In another embodiment, a dosage as disclosed herein comprises about $30 \times 10^6$, $35 \times 10^6$, $40 \times 10^6$, $45 \times 10^6$, $50 \times 10^6$, $55 \times 10^6$, $60 \times 10^6$, $65 \times 10^6$, $70 \times 10^6$, or $75 \times 10^6$ cells from a pooled mononuclear apoptotic cell preparation per kilogram body weight of a subject.

In particular embodiments, the pharmaceutical composition is administered at a dosage of about $35 \times 10^6$ cells per kg body weight. In one embodiment, the pharmaceutical composition is administered at a dosage of about $140 \times 10^6$-$210 \times 10^6$ cells per kg body weight. According to a particular embodiment, the pharmaceutical composition is administered at a dosage of about $140 \times 10^6$ cells per kg body weight. According to another particular embodiment, the pharmaceutical composition is administered at a dosage of about $210 \times 10^6$ cells per kg body weight. According to another particular embodiment, the pharmaceutical composition is administered at a dosage of about $35 \times 10^6$-$210 \times 10^6$ cells per kg body weight. According to another particular embodiment, the pharmaceutical composition is administered at a dosage of about $250 \times 10^6$ cells per kg body weight. In other embodiments, the pharmaceutical composition is administered at a dosage of about $5 \times 10^6$ cells per kg body weight. It should be appreciated that said low dosage is suitable for local injection of the compositions disclosed herein, such as local injection to a joint for treating arthritis.

In one embodiment, the therapeutic pooled mononuclear-enriched cell preparation is administered to the subject systemically, via the intravenous route. Alternately, the therapeutic mononuclear enriched cell may be administered to the subject according to various other routes, including, but not limited to, the parenteral, intraperitoneal, intra-articular, intramuscular and subcutaneous routes. In another embodiment, the therapeutic mononuclear enriched cells are administered to the subject suspended in a suitable physiological buffer, such as, but not limited to, saline solution, PBS, HBSS, and the like. In addition the suspension medium may further comprise supplements conducive to maintaining the viability of the cells. In another embodiment, the suspension medium comprise supplements conducive to maintaining the early apoptotic state of the cells.

In one embodiment, the mononuclear-enriched cell composition obtained according to the production method undergoes freezing in a freezing medium.

In one embodiment, the freezing is gradual. In one embodiment, following collection the cells are maintained at room temperature until frozen. In one embodiment, the cell-preparation undergoes at least one washing step in washing medium following cell-collection and prior to freezing.

A skilled artisan would appreciate that the terms "obtaining cells" and "cell collection" are used interchangeably. In one embodiment, the cells of the cell preparation are frozen within 3-6 hours of collection. In one embodiment, the cell preparation is frozen within up to 6 hours of cell collection. In one embodiment, the cells of the cell preparation are frozen within 1, 2, 3, 4, 5, 6, 7, 8 hours of collection. According to other embodiments, the cells of the cell preparation are frozen up to 8, 12, 24, 48, 72 hours of collection. According to other embodiments, following collection the cells are maintained at 2-8° C. until frozen.

In one embodiment, freezing according to the production method comprises: freezing the cell preparation at about −18° C. to −25° C. followed by freezing the cell preparation at about −80° C. and finally freezing the cell preparation in liquid nitrogen until thawing. In one embodiment, the freezing according to the production method comprises: freezing the cell preparation at about −18° C. to −25° C. for at least 2 hours, freezing the cell preparation at about −80° C. for at least 2 hours and finally freezing the cell preparation in liquid nitrogen until thawing. In one embodiment, the cells are kept in liquid nitrogen for at least 8, 10 or 12 hours prior to thawing. In one embodiment, the cells of the cell preparation are kept in liquid nitrogen until thawing and incubation with apoptosis-inducing incubation medium. In one embodiment, the cells of the cell preparation are kept in liquid nitrogen until the day of hematopoietic stem cell transplantation. According to non-limiting examples, the time from cell collection and freezing to preparation of the final composition may be between 1-50 days, alternatively between 6-30 days. According to alternative embodiments, the cell preparation may be kept in liquid nitrogen for longer time periods, such as at least several months.

In one embodiment, the freezing according to the production method comprises freezing the cell preparation at about −18° C. to −25° C. for at least 0.5, 1, 2, 4 hours. In one embodiment, the freezing according to the production method comprises freezing the cell preparation at about −18° C. to −25° C. for about 2 hours. In one embodiment, the freezing according to the production method comprises freezing the cell preparation at about −80° C. for at least 0.5, 1, 2, 4, 12 hours.

In one embodiment, the mononuclear-enriched cell composition may remain frozen at least 1, 2, 3, 4, 5, 6, 7, 8, 9, 10, 11, 12, 20 months. In one embodiment, the mononuclear-enriched cell composition may remain frozen at least 0.5, 1, 2, 3, 4, 5 years. According to certain embodiments, the mononuclear-enriched cell composition may remain frozen for at least 20 months.

In one embodiment, the mononuclear-enriched cell composition is frozen for at least 8, 10, 12, 18, 24 hours. According to certain embodiments, freezing the mononuclear-enriched cell composition is for a period of at least 8 hours. In one embodiment, the mononuclear-enriched cell composition is frozen for at least about 10 hours. In one embodiment, the mononuclear-enriched cell composition is frozen for at least about 12 hours. In one embodiment, the mononuclear-enriched cell composition is frozen for about 12 hours. In one embodiment, the total freezing time of the mononuclear-enriched cell composition (at about −18° C. to −25° C., at about −80° C. and in liquid nitrogen) is at least 8, 10, 12, 18, 24 hours.

In one embodiment, the freezing at least partly induces the early-apoptotic state in the cells of the mononuclear-enriched cell composition. In one embodiment, the freezing medium comprises RPMI 1640 medium comprising L-glutamine, Hepes, Hes, dimethyl sulfoxide (DMSO) and plasma. In one embodiment, the freezing medium comprises RPMI 1640 medium comprising 2 mM L-glutamine, 10 mM Hepes, 5% Hes, 10% dimethyl sulfoxide and 20% v/v plasma.

In one embodiment, the freezing medium comprises an anti-coagulant. According to certain embodiments, at least some of the media used during the production method, including the freezing medium, the incubation medium and the washing media comprise an anti-coagulant. According to certain embodiments, all media used during the production method which comprise an anti-coagulant comprise the same concentration of anti-coagulant. In one embodiment, anti-coagulant is not added to the final suspension medium of the cell composition.

In one embodiment, addition of an anti-coagulant at least to the freezing medium improves the yield of the cell-preparation. According to other embodiments, addition of an anti-coagulant to the freezing medium improves the yield of the cell-preparation in the presence of a high triglyceride level. As used herein, improvement in the yield of the cell-preparation relates to improvement in at least one of: the percentage of viable cells out of cells frozen, the percentage of early-state apoptotic cells out of viable cells and a combination thereof.

In one embodiment, addition of an anti-coagulant to the freezing medium contributes to a high and stable yield between different preparations of the pharmaceutical composition. According to preferable embodiments, addition of an anticoagulant at least to the freezing medium and incubation medium results in a high and stable yield between different preparations of the pharmaceutical composition, regardless to the cell collection protocol used.

In one embodiment, the freezing medium comprises an anti-coagulant selected from the group consisting of: heparin, ACD Formula A and a combination thereof. In one embodiment, the anti-coagulant used in the freezing medium is ACD Formula A containing heparin at a concentration of 10 U/ml. In one embodiment, the freezing medium comprises 5% v/v of ACD Formula A solution comprising heparin at a concentration of 10 U/ml.

In one embodiment, the freezing medium comprises heparin. In one embodiment, the heparin in the freezing medium is at a concentration of between 0.1-2.5 U/ml. In one embodiment, the heparin in the freezing medium is at a concentration of between 0.1-2.5 U/ml, possibly between 0.3-0.7 U/ml, typically about 0.5 U/ml. According to certain embodiments, the heparin in the freezing medium is at a concentration of about 0.5 U/ml.

In one embodiment, the freezing medium comprises ACD Formula A. In one embodiment, the ACD Formula A in the freezing medium is at a concentration of between 1%-15% v/v. In one embodiment, the ACD Formula A in the freezing medium is at a concentration of between 1%-15% v/v, possibly between 4%-7% v/v, typically about 5% v/v. In one embodiment, the ACD Formula A in the freezing medium is at a concentration of about 5% v/v.

In one embodiment, the mononuclear-enriched cell composition undergoes at least one washing step following cell collection and prior to being re-suspended in the freezing medium and frozen. In one embodiment, the mononuclear-enriched cell composition undergoes at least one washing step following freezing and thawing. In one embodiment, washing steps comprise centrifugation of the mononuclear-enriched cell composition followed by supernatant extraction and re-suspension in washing medium.

In one embodiment, cell collection refers to obtaining a mononuclear-enriched cell composition. In one embodiment, washing steps performed during the production method are performed in a washing medium. According to certain embodiments, washing steps performed up until the incubation step of the production method are performed in a washing medium. In one embodiment, the washing medium comprises RPMI 1640 medium supplemented with L-glutamine and Hepes. In one embodiment, the washing medium comprises RPMI 1640 medium supplemented with 2 mM L-glutamine and 10 mM Hepes.

In one embodiment, the washing medium comprises an anti-coagulant. In one embodiment, the washing medium comprises an anti-coagulant selected from the group consisting of: heparin, ACD Formula A and a combination thereof. In one embodiment, the concentration of the anti-coagulant in the washing medium is the same concentration as in the freezing medium. In one embodiment, the concentration of the anti-coagulant in the washing medium is the same concentration as in the incubation medium. In one embodiment, the anti-coagulant used in the washing medium is ACD Formula A containing heparin at a concentration of 10 U/ml.

In one embodiment, the washing medium comprises heparin. In one embodiment, the heparin in the washing medium is at a concentration of between 0.1-2.5 U/ml. In one embodiment, the heparin in the washing medium is at a concentration of between 0.1-2.5 U/ml, possibly between 0.3-0.7 U/ml, typically about 0.5 U/ml. According to certain embodiments, the heparin in the washing medium is at a concentration of about 0.5 U/ml.

In one embodiment, the washing medium comprises ACD Formula A. In one embodiment, the ACD Formula A in the washing medium is at a concentration of between 1%-15% v/v. In one embodiment, the ACD Formula A in the washing medium is at a concentration of between 1%-15% v/v, possibly between 4%-7% v/v, typically about 5% v/v. In one embodiment, the ACD Formula A in the washing medium is at a concentration of about 5% v/v.

In one embodiment, the pooled mononuclear-enriched cell composition is thawed several hours prior to the intended administration of the composition to a subject. In one embodiment, the mononuclear-enriched cell composition is thawed at about 33° C.-39° C. In one embodiment, the mononuclear-enriched cell composition is thawed for about 30-240 seconds, preferably 40-180 seconds, most preferably 50-120 seconds.

In one embodiment, the pooled mononuclear-enriched cell composition is thawed at least 10 hours prior to the intended administration of the composition, alternatively at least 20, 30, 40 or 50 hours prior to the intended administration of the composition. In one embodiment, the mononuclear-enriched cell composition is thawed at least 15-24 hours prior to the intended administration of the composition. In one embodiment, the mononuclear-enriched cell composition is thawed at least about 24 hours prior to the intended administration of the composition. In one embodiment, the mononuclear-enriched cell composition is thawed at least 20 hours prior to the intended administration of the composition. In one embodiment, the mononuclear-enriched cell composition is thawed 30 hours prior to the intended administration of the composition. In one embodiment, the mononuclear-enriched cell composition is thawed at least 24 hours prior to the intended administration of the composition. In one embodiment, the mononuclear-enriched cell composition undergoes at least one step of washing in the washing medium before and/or after thawing.

In one embodiment, the pooled mononuclear-enriched cell composition is incubated in incubation medium following freezing and thawing. In one embodiment, there is at least one washing step between thawing and incubation. As used herein, the terms "incubation medium" and "apoptosis inducing incubation medium" are used interchangeably. In one embodiment, the incubation medium comprises RPMI 1640 medium supplemented with L-glutamine, Hepes methylprednisolone and plasma. In one embodiment, the washing medium comprises 2 mM L-glutamine, 10 mM Hepes and 10% v/v blood plasma. In one embodiment, the blood plasma in in the incubation medium is obtained from the same donor from whom the cells of the cell preparation are obtained. In one embodiment, the blood plasma is added to the incubation medium on the day of incubation. In one embodiment, incubation is performed at 37° C.

In one embodiment, the incubation medium comprises methylprednisolone. In one embodiment, the methylprednisolone within the incubation medium further induces the cells in the mononuclear-enriched cell composition to enter an early-apoptotic state. In one embodiment, the cells in the mononuclear-enriched cell composition are induced to enter an early-apoptotic state both by freezing and incubating in the presence of methylprednisolone. In one embodiment, the production method advantageously allows induction of an early-apoptosis state substantially without induction of necrosis, wherein the cells remain stable at said early-apoptotic state for about 24 hours following preparation.

In one embodiment, the incubation medium comprises methylprednisolone at a concentration of about 10-100 µg/ml. In one embodiment, the incubation medium comprises methylprednisolone at a concentration of about 40-60 µg/ml, alternatively about 45-55 µg/ml. In one embodiment, the incubation medium comprises methylprednisolone at a concentration of 50 g/ml.

In one embodiment, the incubation is for about 2-12 hours, possibly 4-8 hours, typically for about 5-7 hours. In one embodiment, the incubation is for about 6 hours. In one embodiment, the incubation is for at least 6 hours. According to a preferred embodiment, the incubation is for 6 hours.

In one embodiment, the incubation medium comprises an anti-coagulant. In one embodiment, addition of an anti-coagulant to the incubation medium improves the yield of the cell-preparation. In one embodiment, the anti-coagulant in the incubation medium is of the same concentration as within the freezing medium. In one embodiment, the incubation medium comprises an anti-coagulant selected from the group consisting of: heparin, ACD Formula A and a combination thereof. In one embodiment, the anti-coagulant used in the incubation medium is ACD Formula A containing heparin at a concentration of 10 U/ml.

In one embodiment, the incubation medium comprises heparin. In one embodiment, the heparin in the incubation medium is at a concentration of between 0.1-2.5 U/ml. In one embodiment, the heparin in the incubation medium is at a concentration of between 0.1-2.5 U/ml, possibly between 0.3-0.7 U/ml, typically about 0.5 U/ml. According to certain embodiments, the heparin in the incubation medium is at a concentration of about 0.5 U/ml.

In one embodiment, the incubation medium comprises ACD Formula A. In one embodiment, the ACD Formula A in the incubation medium is at a concentration of between 1%-15% v/v. In one embodiment, the ACD Formula A in the incubation medium is at a concentration of between 1%-15% v/v, possibly between 4%-7% v/v, typically about 5% v/v. In one embodiment, the ACD Formula A in the incubation medium is at a concentration of about 5% v/v.

In one embodiment, both the freezing medium and the incubation medium comprise an anti-coagulant. In one embodiment, addition of an anticoagulant both to the incubation medium and freezing medium results in a high and stable cell-yield between different preparations of the composition regardless of cell-collection conditions, such as, but not limited to, the timing and/or type of anti-coagulant added during cell collection. In one embodiment, addition of an anti-coagulant both to the incubation medium and freezing medium results in a high and stable yield of the cell-preparation regardless of the timing and/or type of anti-coagulant added during leukapheresis.

In one embodiment, a blood of a donor having a high triglyceride level will be excluded from pooled mononuclear enriched preparations. In one embodiment, the term "high triglyceride level" refers to a triglyceride level which is above the normal level of a healthy subject of the same sex and age. In one embodiment, the term "high triglyceride level" refers to a triglyceride level above about 1.7 milimole/liter.

A skilled artisan would appreciate that a high and stable yield refers to a cell yield in the composition which is high enough to enable preparation of a dose which will demonstrate therapeutic efficiency when administered to a subject. In one embodiment, therapeutic efficiency refers to the ability to treat, prevent or ameliorate an immune disease, an autoimmune disease or an inflammatory disease in a subject. In one embodiment, a high and stable cell yield is a cell yield of at least 30%, possibly at least 40%, typically at least 50% of cells in the composition out of cells initially frozen.

In one embodiment, addition of an anti-coagulant to the incubation medium and/or freezing medium results in a high and stable cell yield within the composition regardless of the triglyceride level in the blood of the donor. In one embodiment, addition of an anti-coagulant to the incubation medium and/or freezing medium results in a high and stable cell yield within the composition when obtained from the blood of a donor having normal or high triglyceride level. In one embodiment, addition of an anti-coagulant at least to the incubation medium, results in a high and stable cell yield within the composition regardless of the triglyceride level in the blood of the donor. In one embodiment, addition of an anti-coagulant to the freezing medium and incubation medium results in a high and stable cell yield within the composition regardless of the triglyceride level in the blood of the donor.

In one embodiment, the freezing medium and/or incubation medium and/or washing medium comprise heparin at a concentration of at least 0.1 U/ml, possibly at least 0.3 U/ml, typically at least 0.5 U/ml. In one embodiment, the freezing medium and/or incubation medium and/or washing medium comprise ACD Formula A at a concentration of at least 1% v/v, possibly at least 3% v/v, typically at least 5% v/v.

In one embodiment, the mononuclear-enriched cell composition undergoes at least one washing step between each stage of the production method. In one embodiment, anti-coagulant is added to washing media during washing steps throughout the production method. In one embodiment, the mononuclear-enriched cell composition undergoes at least one washing step following incubation. In one embodiment, the mononuclear-enriched cell composition undergoes at least one washing step following incubation using PBS. In one embodiment, anti-coagulant is not added to the final washing step prior to re-suspension of the cell-preparation in the administration medium. In one embodiment, anti-coagulant is not added to the PBS used in the final washing step prior to re-suspension of the cell-preparation in the administration medium. According to certain embodiments, anti-coagulant is not added to the administration medium.

In one embodiment, the cell concentration during incubating is about $5 \times 10^6$ cells/ml.

In one embodiment, the pooled mononuclear-enriched cell composition is suspended in an administration medium following freezing, thawing and incubating, thereby resulting in the pharmaceutical composition. In one embodiment, the administration medium comprises a suitable physiological buffer. Non-limiting examples of a suitable physiological buffer are: saline solution, Phoshpate Buffered Saline (PBS), Hank s Balanced Salt Solution (HBSS), and the like. In one embodiment, the administration medium comprises PBS. In one embodiment, the administration medium comprises supplements conducive to maintaining the viability of the cells. In one embodiment, the mononuclear-enriched cell composition is filtered prior to administration. In one embodiment, the mononuclear-enriched cell composition is filtered prior to administration using a filter of at least 200 μπι.

In one embodiment, the pooled mononuclear-enriched cell composition is re-suspended in an administration medium such that the final volume of the resulting cell-preparation is between 100-1000 ml, possibly between 200-800 ml, typically between 300-600 ml.

In one embodiment, the method for producing the pharmaceutical composition further comprises obtaining the pooled mononuclear-enriched cell compositions as described above.

In one embodiment, the present disclosure provides the cell-preparation, wherein the cell-preparation is produced by the production method. In one embodiment, a composition as disclosed herein comprises 100% allogeneic cells. In another embodiment, a composition comprises less than 100% allogeneic cells.

In one embodiment, step (f) of a method for producing a pooled mononuclear apoptotic cell preparation comprising inactivating said mononuclear-enriched populations comprises suppressing or eliminating an immune response in said individual populations, suppressing or eliminating cross-reactivity between said individual populations, or reducing or eliminating T-cell receptor activity in said individual populations, and wherein said produced pharmaceutical composition comprising said pooled mononuclear apoptotic cell preparation comprises a decreased percent of non-quiescent non-apoptotic cells, a suppress cellular activation of any living non-apoptotic cells, or a reduced proliferation of any living non-apoptotic cells, or any combination thereof within said cell preparation.

In one embodiment, a method of preparing a cell preparation comprises an irradiation step. In another embodiment, a method of preparing a pooled apoptotic cell preparation comprises suppressing the activation or proliferation of non-apoptotic cells present in said cell preparation. In some embodiments, said suppressing comprises irradiating the cell preparation.

In one embodiment, step (f) "inactivating" comprising decreasing the percent of non-quiescent non-apoptotic cells, suppressing cellular activation of any living non-apoptotic cells, or reducing the proliferation of any living non-apoptotic cells, or any combination thereof within said resuspended cell population, comprises a step of irradiating the cell preparation. In another embodiment, inactivating said mononuclear enriched populations comprises irradiating said mononuclear-enriched populations. In another embodiment, an irradiation step effectively reduces the percent of cells able to cause, for example, GVHD, upon administration of said preparation. In another embodiment, an irradiation step reduces the actual number of non-quiescent non-apoptotic cells compared with a non-irradiated cell preparation. In another embodiment, an irradiation step reduces the percent of non-quiescent non-apoptotic cells compared with a non-irradiated cell preparation.

In another embodiment, methods for producing a pharmaceutical composition comprising irradiation, comprise comprises gamma irradiation or UV irradiation. In another embodiment, methods for producing a pharmaceutical composition comprising irradiation, comprise about 15 Grey units (Gy) irradiation. In another aspect, the irradiation comprises about 20 Grey units (Gy). In another aspect, the irradiation comprises about 25 Grey units (Gy). In another aspect, the irradiation comprises about 30 Grey units (Gy). In another aspect, the irradiation comprises about 35 Grey units (Gy). In another aspect, the irradiation comprises about 40 Grey units (Gy). In another aspect, the irradiation comprises about 45 Grey units (Gy). In another aspect, the irradiation comprises about 50 Grey units (Gy). In another aspect, the irradiation comprises about 55 Grey units (Gy). In another aspect, the irradiation comprises about 60 Grey units (Gy). In another aspect, the irradiation comprises about 65 Grey units (Gy). In another embodiment, irradiation comprises up to 2500 Gy. In another embodiment, the irradiation comprises about 15-25 Grey units (Gy). In another embodiment, the irradiation comprises about 25-30 Grey units (Gy). In another embodiment, the irradiation comprises about 30-40 Grey units (Gy). In another embodiment, the irradiation comprises about 40-50 Grey units (Gy). In another embodiment, the irradiation comprises about 50-65 Grey units (Gy).

In one embodiment, a composition as disclosed herein may be frozen and then thawed and administered to a subject at a medical center. In another embodiment, a pooled mononuclear cells collected by leukapheresis may be frozen and stored in liquid nitrogen prior to a time of use, wherein the pooled mononuclear cells are thawed and early apoptosis is induced as described above, followed by preparing a cell suspension composition for administration to a subject at a medical center. In another embodiment, a composition as disclosed herein may be in a "ready to use" form, wherein it is refrigerated at between about 2-8° C. and stable for use within 24 hours.

Uses of a Pooled Mononuclear Apoptotic Cell Preparation

In one embodiment, this disclosure provides a method of treating, preventing, ameliorating, inhibiting, or reducing the incidence of an immune disease, an autoimmune disease, a cytokine release syndrome (CRS), a cytokine storm, or an inflammatory disease in a subject in need thereof, comprising administering to the subject a pharmaceutical composition comprising a pooled mononuclear apoptotic cell preparation treating, preventing, ameliorating, inhibiting, or reducing the incidence of as described in detail above. In another embodiment, apoptotic cells are efficiently cleared following administration of a pooled mononuclear apoptotic cell preparation.

A skilled artisan would appreciate that the terms "treatment" or "treating" encompass both therapeutic treatment and prophylactic or preventative measures including amelioration of a disease or condition, wherein the object is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, a subject of methods of use as disclosed herein is an adult human. In another embodiment, a subject of methods of use as disclosed herein is a human child. In another embodiment, a subject of methods of use is a human infant.

In one embodiment, an immune disease treated by the methods disclosed herein, is selected from the group comprising GvHD, arthritic, gout, or inflammatory bowel disease.

In one embodiment, induction of early-apoptosis in an enriched pooled mononuclear cell preparation, according to the methods disclosed herein, provides a clinical grade population of apoptotic non-HLA matched allogeneic donor cells which, when infused with the bone marrow obtained cells, affected important factors associated with transplantation, and effectively reduced the incidence of GVHD in subjects with hematological malignancies.

GvHD

Particularly, at 100 days post transplantation, incidence of Grade II-IV GVHD may be reduced in HSC transplant recipients treated with the apoptotic donor cells prepared and the non-relapsed survival rate was significantly increased. Details of use of an early apoptotic cell preparation are disclosed in WO 2014/087408, which is incorporated herein in full.

Further, in another embodiment, infusion of the apoptotic donor cells prepared according to the methods is effective in reducing the time to engraftment of the HSC and remarkably reducing the incidence of hepatotoxicity in HSC transplant recipients.

In one embodiment, the present disclosure provides a method of treating, preventing, ameliorating, inhibiting, or reducing the incidence of GVHD in a subject undergoing HSCT, comprising administering to the subject the pharmaceutical composition. In another embodiment, the present disclosure provides a method of treating infertility in a subject.

In one embodiment, the present disclosure provides a method of preventing, ameliorating, inhibiting, or reducing the incidence of GVHD in a subject undergoing HSCT, comprising administering to the subject the pharmaceutical composition. In one embodiment, the present disclosure provides a method of treating, preventing, ameliorating, inhibiting, or reducing the incidence of GVHD in a subject undergoing HSCT, comprising administering to the subject the pharmaceutical composition comprising a pooled mononuclear apoptotic cell preparation or pharmaceutical composition thereof, as described in detail herein as described herein in detail above. In one embodiment, the present disclosure provides a method of treating, treating, preventing, ameliorating, inhibiting, or reducing the incidence of, ameliorating, inhibiting, or reducing the incidence of GVHD in a subject undergoing HSCT, comprising administering to the subject the pharmaceutical composition as disclosed herein in detail above.

In one embodiment, the present disclosure provides a method of treating, preventing, ameliorating, inhibiting, or reducing the incidence of GVHD in a subject undergoing HSCT, comprising administering to the subject a pharmaceutical composition comprising a cell preparation comprising pooled mononuclear enriched cells as disclosed in detail above; and wherein the pharmaceutical composition comprises an anti-coagulant selected from the group consisting of: heparin, ACD Formula A and a combination thereof.

In one embodiment, the present disclosure provides a method of treating, preventing, ameliorating, inhibiting, or reducing the incidence of GVHD in a subject undergoing HSCT, comprising administering to the subject a pharmaceutical composition comprising a pooled mononuclear apoptotic cell preparation or pharmaceutical composition thereof, as described in detail herein, as disclosed herein in detail above; and wherein the pharmaceutical composition comprises an anti-coagulant selected from the group consisting of: heparin, ACD Formula A and a combination thereof.

In one embodiment, the present disclosure provides a method of treating, preventing, ameliorating, inhibiting, or reducing the incidence of GVHD in a subject undergoing HSCT, comprising administering to the subject a pharmaceutical composition comprising a cell preparation comprising pooled mononuclear enriched cells, as disclosed herein in detail above, and wherein the preparation comprises methylprednisolone at a concentration that does not exceed 30 µg/ml. In one embodiment treating, preventing, ameliorating, inhibiting, or reducing the incidence of In one embodiment treating, preventing, ameliorating, inhibiting, or reducing the incidence of In one embodiment treating, preventing, ameliorating, inhibiting, or reducing the incidence of a pooled mononuclear apoptotic cell preparation or pharmaceutical composition thereof, as described in detail herein.

In one embodiment treating, preventing, ameliorating, inhibiting, or reducing the incidence of In one embodiment treating, preventing, ameliorating, inhibiting, or reducing the incidence of In one embodiment, the present disclosure provides the pharmaceutical composition for use in treating, preventing, ameliorating, inhibiting, or reducing the incidence of treating, preventing, ameliorating, inhibiting, or reducing the incidence of GVHD in a subject undergoing HSCT. In another embodiment, said HSCT comprises allogeneic HSCT and said pharmaceutical composition comprises cells obtained from multiple allogeneic donors not HLA matched to said recipient subject; nor are cells from said multiple allogeneic donors HLA matched one to another.

In one embodiment, the GVHD is high grade GVHD. According to specific embodiments, high grade GVHD is grade II-IV GVHD. According to another specific embodiment, high grade GVHD is grade III-IV GVHD. According to a particular embodiment, the pharmaceutical composition induces a shift from high grade GVHD to grade I GVHD.

According to another embodiment, the GVHD is acute GVHD. According to yet another embodiment, the GVHD is chronic GVHD. According to another particular embodiment, a subject administered with the pharmaceutical composition retains a graft-versus-tumor (GVTS) or graft-versus-leukemia (GVL) effect.

In one embodiment, the GVHD is GVHD in the liver of the subject. Liver dysfunction in allogeneic HSCT recipients may be due to a variety of factors including toxicity from the preparative regimen and other medications, infection, veno-occlusive disease (VOD), and acute and chronic graft-versus-host disease (GVHD) of the liver.

According to another embodiment, the pharmaceutical composition reduces hepatotoxicity associated with GVHD. In one embodiment, the cell preparation reduces hepatotoxicity associated with GVHD. Common symptoms and complications of Hepatotoxicity include lymphadenitis, fever, red blood cell sedimentation rate increased high bilirubin levels and febrile neutropenia.

Immune Diseases, Autoimmune Diseases, Inflammatory Diseases, a Cytokine Release Syndrome (CRS), & a Cytokine Storm In one embodiment, the present disclosure provides a method of treating, preventing, ameliorating, inhibiting, or reducing the incidence of an immune disease or an autoimmune disease or an inflammatory disease of a cytokine release syndrome (CRS) or a cytokine storm in a subject in need thereof, comprising administering to the subject a pharmaceutical composition comprising the cell preparation disclosed herein in detail above. In one embodiment, the present disclosure provides a method of treating, preventing, ameliorating, inhibiting, or reducing the incidence of an immune disease or an autoimmune disease or an inflammatory disease of a cytokine release syndrome (CRS) or a cytokine storm in a subject in need thereof, comprising administering to the subject the pharmaceutical composition as described in detail herein above.

In one embodiment, the present disclosure provides the pooled cell preparation for use in treating, preventing, ameliorating, inhibiting, or reducing the incidence of an immune disease or an autoimmune disease or an inflammatory disease of a cytokine release syndrome (CRS) or a cytokine storm in a subject in need thereof. In one embodiment, the present disclosure provides the pharmaceutical composition for use in treating, preventing, ameliorating, inhibiting, or reducing the incidence of an immune disease or an autoimmune disease or an inflammatory disease of a cytokine release syndrome (CRS) or a cytokine storm in a subject in need thereof.

In one embodiment, the immune disease is GVHD. In one embodiment, the present disclosure provides the pharmaceutical composition for use in treating, preventing, ameliorating, inhibiting, or reducing the incidence of GVHD in a subject in need thereof.

In one embodiment, the present disclosure provides a method of treating, preventing, ameliorating, inhibiting, or reducing the incidence of a hematopoietic malignancy comprising administering to a subject in need thereof the pharmaceutical composition. According to particular embodiments, the subject is suffering from a hematopoietic malignancy.

The term "hematopoietic malignancy" as used herein refers to any blood cell cancer, characterized by uncontrolled, abnormal growth of blood cells. The term "hematopoietic malignancy" includes but is not limited to leukemia, myelodysplastic syndrome, lymphoma, and multiple myeloma (plasma cell dyscrasia). The term "leukemia" refers to a disease of the blood forming organs characterized by an abnormal increase in the number of leucocytes in the tissues of the body with or without a corresponding increase of those in the circulating blood (e.g., acute lymphoblastic leukemia, ALL; acute myelogenous leukemia, AML; chronic myelogenous leukemia, CML; etc.). The term "myelodysplastic syndrome" refers to a condition in which the bone marrow shows qualitative and quantitative changes suggestive of a preleukemic process, but having a chronic course that does not necessarily terminate as acute leukemia. The term "lymphoma" refers to a malignant tumor of lymphoblasts obtained from B or T lymphocytes (e.g., Hodgkin lymphoma, HL; non-Hodgkin lymphoma, NHL; etc.). The term "plasma cell dyscrasia" refers to plasmacytosis due to plasma cell proliferation (e.g., multiple myeloma, MM; plasma cell leukemia, PCL; etc.)

According to exemplary embodiments, said hematopoietic malignancy is selected from the group consisting of MDS, acute lymphoblastic leukemia (ALL), acute myeloid leukemia (AML) and chronic myelogenous leukemia (CML).

Infusion of certain types of the donor blood cells such as T-lymphocytes can also stimulate a graft-versus-leukemia effect. This effect has been best observed in patients with chronic myeloid leukemia (CML). In CML, 75 percent of patients relapsing after transplant re-enter remission. For other disorders such as acute myeloid leukemia (AML) and myelodysplastic syndrome (MDS), the effect is less pronounced; AML and MDS in approximately 20 percent of patients enter remission. For patients with acute lymphoblastic leukemia (ALL), the presence of graft-vs-leukemia effect is unclear, although small numbers of patients have reportedly benefited, at least transiently, from the effect.

In other ways, the pooled donor immune cells may recognize residual leukemia, lymphoma or cancer cells as being different and destroy them. Retrospective studies have demonstrated that patients in whom acute or chronic GVHD develops have lower disease recurrence rates than patients who do not develop GVHD. This finding is an indirect indication of a graft-versus-tumor effect.

The term "conditioning treatment" refers to preparative treatment of transplant recipient with various conditioning regimens including radiation, immune sera, chemotherapy, and/or immunosuppressive agents, prior to transplantation. Transplantation conditioning is very common before bone marrow transplantation.

A skilled artisan would appreciate that the terms "subject", "patient", "recipient", and "subject in need thereof" may be used interchangeably and may encompass a subject in need of administration of the pharmaceutical composition.

In one embodiment, the pharmaceutical composition is administered to a subject who has undergone or will undergo HSCT. In one embodiment, a subject in need thereof is a subject undergoing HSCT. In one embodiment, the Hematopoietic Stem Cells (HSCs) transplanted into a subject in need thereof and the cells of the pharmaceutical composition are obtained from the same donor.

According to another embodiment, administering of the pharmaceutical composition is carried out up to 24 hours prior to the HSCT. In one embodiment, administering of the pharmaceutical composition is carried out about 24-30 hours prior to the HSCT. According to yet another embodiment, the administering of the pharmaceutical composition is carried out at the same time as the HSCT. In one embodiment, the administering of the pharmaceutical composition is carried out up to 15 days following the HSCT. According to additional embodiments, the HSCs used in the HSCT are allogeneic HSCs. According to non-limiting examples, the HSCs used in the HSCT may be obtained from bone marrow, peripheral blood, or umbilical cord blood. According to another embodiment, the pharmaceutical composition is administered in a single dose.

Inflammatory bowel diseases (IBD) are characterized by chronic intestinal inflammation with dysregulation of the mucosal immune system in the gastrointestinal tract manifested as Crohn's disease and ulcerative colitis. As used herein, the term IBD refers to Crohn's disease, ulcerative colitis or a combination thereof. Genetic factors and environmental factors that include both intestinal microflora and danger signals such as dextran sodium sulfate (DSS) were all shown to induce intestinal inflammation. TNFa and IFNy blockade and anti-IL-Iβ strategies, as well as antibiotic treatment were able to ameliorate colitis induction, suggesting a role for nuclear factor-kappa B (NF-κB) and inflammasome inhibition of macrophages and dendritic cells in the lamina propria.

In one embodiment, the pooled apoptotic cell composition negatively regulates the NLRP3 inflammasome, both in vitro and in vivo, and is able to downregulate the pro-inflammatory response induced via NLRP3 inflammasome in hematopoietic cells.

In one embodiment, the present disclosure provides a method of treating, preventing, ameliorating, inhibiting, or reducing the incidence of IBD in a subject in need thereof, comprising administering to the subject the pharmaceutical composition. In one embodiment, the present disclosure provides the pharmaceutical composition for use in treating, preventing, ameliorating, inhibiting, or reducing the incidence of IBD in a subject in need thereof.

In one embodiment, the present disclosure provides a method of treating, preventing, ameliorating, inhibiting, or reducing the incidence of IBD in a subject in need thereof, comprising administering to the subject a pharmaceutical composition comprising a pooled mononuclear apoptotic cell preparation or pharmaceutical composition thereof, as described in detail herein. prises no more than 15% polymorphonuclear leukocytes; and wherein the pharmaceutical composition comprises an anti-coagulant selected from the group consisting of: heparin, ACD Formula A and a combination thereof.

In one embodiment, the present disclosure provides a method of treating, preventing, ameliorating, inhibiting, or reducing the incidence of IBD in a subject in need thereof, comprising administering to the subject a pharmaceutical composition comprising a pooled mononuclear apoptotic cell preparation or pharmaceutical composition thereof, as described in detail herein.

In one embodiment, a method of treating, preventing, ameliorating, inhibiting, or reducing the incidence of an immune disease comprises administering a composition as disclosed herein to a subject undergoing solid organ transplantation. In one embodiment, the organ is selected from the group consisting of lung, heart, kidney, pancreas, liver, skin and small-bowel. In another embodiment, a solid organ comprises beta cells. In another embodiment, a solid organ is a limb.

In one embodiment, a composition of method as disclosed herein administering of the pharmaceutical composition are carried out up to 24 hours prior to said transplantation. In another embodiment, the administering of the pharmaceutical composition is carried out at the same time as the transplantation. In yet another embodiment, a composition as disclosed herein is administered until 15 days following said transplantation. In another embodiment, administration comprises a single administration. In still another embodiment, administration comprises repeat dosing with a composition as disclosed herein. In another embodiment, repeat dosing shows increased effectiveness.

In one embodiment, immunogenic response to administration of a composition as disclosed herein is monitored. In another embodiment, administration of a composition as disclosed herein is halted in response to a negative immune response for example wherein antibodies are produced that negatively impact administration and treating of said subject. In another embodiment, immune response to administration of a composition as disclosed herein is monitored for neutralizing antibodies.

In one embodiment, an inflammatory disease treated with a composition as disclosed herein is arthritis. In another embodiment, an inflammatory disease treated with a composition as disclosed herein is gout. In yet another embodiment, an inflammatory disease is inflammatory bowel disease.

In one embodiment, an inflammatory bowel disease treated with a composition as disclosed herein is selected from the group consisting of: Crohn's disease, ulcerative colitis and a combination thereof.

Cytokine Storm and Cytokine Release Syndrome

In one embodiment, a method as disclosed herein includes providing a pooled mononuclear apoptotic cell preparation, as described in detail herein, to decrease toxic cytokine release or "cytokine release syndrome" (CRS) or "severe cytokine release syndrome" (sCRS) or "cytokine storm" that may occur in a subject. In another embodiment the CRS, sCRS or cytokine storm occurs as a result of administration of immune cells. In another embodiment, the CRS, sCRS or cytokine storm is the result of a stimulus, condition, or syndrome separate from the immune cells (see below). In another embodiment, a cytokine storm, cytokine cascade, or hypercytokinemia is a more severe form of cytokine release syndrome.

A skilled artisan would appreciate that decreasing toxic cytokine release or toxic cytokine levels comprises decreasing or inhibiting production of toxic cytokine levels in a subject, or inhibiting or reducing the incidence of cytokine release syndrome or a cytokine storm in a subject. In another embodiment toxic cytokine levels are reduced during CRS or a cytokine storm. In another embodiment, decreasing or inhibiting the production of toxic cytokine levels comprises treating CRS or a cytokine storm. In another embodiment, decreasing or inhibiting the production of toxic cytokine levels comprises preventing CRS or a cytokine storm. In another embodiment, decreasing or inhibiting the production of toxic cytokine levels comprises alleviating CRS or a cytokine storm. In another embodiment, decreasing or inhibiting the production of toxic cytokine levels comprises ameliorating CRS or a cytokine storm. In another embodiment, the toxic cytokines comprise pro-inflammatory cytokines. In another embodiment, pro-inflammatory cytokines comprise IL-6. In another embodiment, pro-inflammatory cytokines comprise IL-1β. In another embodiment, pro-inflammatory cytokines comprise TNF-α, In another embodiment, pro-inflammatory cytokines comprise IL-6, IL-1β, or TNF-α, or any combination thereof.

In one embodiment, cytokine release syndrome is characterized by elevated levels of several inflammatory cytokines and adverse physical reactions in a subject such as low blood pressure, high fever and shivering. In another embodiment, inflammatory cytokines comprise IL-6, IL-1β, and TNF-α. In another embodiment, CRS is characterized by elevated levels of IL-6, IL-1β, or TNF-α, or any combination thereof. In another embodiment, CRS is characterized by elevated levels of IL-8, or IL-13, or any combination thereof. In another embodiment, a cytokine storm is characterized by increases in TNF-alpha, IFN-gamma, IL-1beta, IL-2, IL-6, IL-8, IL-10, IL-13, GM-CSF, IL-5, fracktalkine, or a combination thereof or a subset thereof. In yet another embodiment, IL-6 comprises a marker of CRS or cytokine storm. In another embodiment, IFN-γ comprises a marker of CRS or cytokine storm. In another embodiment, patients with larger tumor burdens have higher incidence and severity of cytokine release syndrome.

In another embodiment, cytokines increased in CRS or a cytokine storm in humans and mice may comprise any combination of cytokines listed in Tables 1 and 2 below.

TABLE 1

Panel of Cytokines Increased in CRS or Cytokine Storm in Humans and/or Mice

| Cytokine (Analyte) | Human model (clinical trials) | Mouse model (pre-clinical) | | | Cells secreting this cytokine | Notes/ other |
| --- | --- | --- | --- | --- | --- | --- |
| | | CAR-T (H) origin | Mouse origin | Not specified | | |
| Flt-3L | * | | | | DC (?) | |
| Fractalkine | * | | | | APC, Endothelial cells (?) | = CX3CL1, Neurotactin (Mouse) |
| M-CSF | | | | | | = CSF1 |
| GM-CSF | * | | | * (in vitro) | T cell, MØ | |
| IFN-α | * | | | | T cell, MØ, Monocyte | |
| IFN-β | ? | | | ? | T cell, MØ, Monocyte | |
| IFN-γ | * | * | | * (in vitro) | cytotoxic T cells, helper T cells, NK cells, MØ, Monocyte, DC | |
| IL-1α | * | | | | Monocyte, MØ, Epithel | |
| IL-1β | * | | | * | Macrophages, DCs, fibroblasts, endothelial cells, hepatocytes | |
| IL-1Rα | * | | | | | |
| IL-2 | * | * | | * (in vitro) | T cells | |
| IL-2Rα | * | | | | lymphocytes | |
| IL-4 | * | * | | * (in vitro) | Th2 cells | |
| IL-5 | * | * | | * | T cells | |
| IL-6 | * | | * | * | monocytes/ macrophages, dendritic cells, T cells, fibroblasts, keratinocytes, endothelial cells, adipocytes, myocytes, mesangial cells, and osteoblasts | |
| IL-7 | * | | | * | In vitro by BM stromal cells | |
| IL-8 | * | | | | Macrophages, monocytes | |
| IL-9 | * | * | | | T cells, T helper | |
| IL-10 | * | * | * | * (in vitro) | monocytes/macrophages, mast cells, B cells, regulatory T cells, and helper T cells | |
| IL-12 | * | | | * | MØ, Monocyte, DC, activated lymphocytes, neutrophils | = p70 (p40 + p35) |
| IL-13 | * | * | | | T cells | |

In one embodiment, cytokines Flt-3L, Fractalkine, GM-CSF, IFN-γ, IL-1β, IL-2, IL-2Rα, IL-4, IL-5, IL-6, IL-7, IL-8, IL-9, IL-10, IL-12, and IL-13 of Table 1 are considered to be significant in CRS or cytokine storm. In another embodiment, IFN-α, IFN-β, IL-1, and IL-1Rα of Table 1 appear to be important in CRS or cytokine storm. In another embodiment, M-CSF has unknown importance. In another embodiment, any cytokine listed in Table 1, or combination thereof, may be used as a marker of CRS or cytokine storm.

TABLE 2

Panel of Cytokines Increased in CRS or Cytokine Storm in Humans and/or Mice

| Cytokine (Analyte) | Human model (clinical trials) | Mouse model (pre-clinical) CAR-T (H) origin | Mouse origin | Not specified | Cells secreting this cytokine | Notes/ other |
|---|---|---|---|---|---|---|
| IL-15 | * | | | * | Fibroblasts, monocytes ? | 22 |
| IL-17 | * | | | * | T cells | |
| IL-18 | | | | | Macrophages | |
| IL-21 | * | | | | T helper cells, NK cells | |
| IL-22 | * | | | | activated DC and T cells | |
| IL-23 | | | | | | |
| IL-25 | | | | | | Protective ? |
| IL-27 | * | | | | APC | |
| IP-10 | * | | | | Monocytes (?) | |
| MCP-1 | * | | | | Endothel, fibroblast, epithel, monocytes | = CXCL10 |
| MCP-3 | * | | | | PBMCs, MØ (?) | = CCL2 |
| MIP-1α | * | | | * (in vitro) | T cells | = CXCL9 |
| MIP-1β | * | | | | T cells | = CCL3 |
| PAF | ? | | | | platelets, endothelial cells, neutrophils, monocytes, and macrophages, mesangial cells | = CCL4 |
| PGE2 | * | | | * | Gastrointestinal mucosa and other | |
| RANTES | * | | | | Monocytes | |
| TGF-β | * | | | * | MØ, lymphocytes, endothel, platelets . . . | = CCL5 |
| TNF-α | * | * | * | * (in vitro) | Macrophages, NK cells, T cells | |
| TNF-αR1 | * | | | | | |
| HGF | | | | | | |
| MIG | * | | | | T cell chemoattractant, induced by IFN-γ | |

In one embodiment, IL-15, IL-17, IL-18, IL-21, IL-22, IP-10, MCP-1, MIP-1α, MIP-1β, and TNF-α of Table 2 are considered to be significant in CRS or cytokine storm. In another embodiment, IL-27, MCP-3, PGE2, RANTES, TGF-β, TNF-αR1, and MIG of Table 2 appear to be important in CRS or cytokine storm. In another embodiment, IL-23 and IL-25 have unknown importance. In another embodiment, any cytokine listed in Table 2, or combination thereof, may be used as a marker of CRS or cytokine storm.

A skilled artisan would appreciate that the term "cytokine" may encompass cytokines (e.g., interferon gamma, granulocyte macrophage colony stimulating factor, tumor necrosis factor alpha), chemokines (e.g., MIP 1 alpha, MIP 1 beta, RANTES), and other soluble mediators of inflammation, such as reactive oxygen species and nitric oxide.

In one embodiment, increased release of a particular cytokine, whether significant, important or having unknown importance, does not a priori mean that the particular cytokine is part of a cytokine storm. In one embodiment, an increase of at least one cytokine is not the result of a cytokine storm or CRS. In another embodiment, CAR T-cells may be the source of increased levels of a particular cytokine or group of cytokines.

In another embodiment, cytokine release syndrome is characterized by any or all of the following symptoms: Fever with or without rigors, malaise, fatigue, anorexia, myalgias, arthralgias, nausea, vomiting, headache Skin Rash, Nausea, vomiting, diarrhea, Tachypnea, hypoxemia Cardiovascular Tachycardia, widened pulse pressure, hypotension, increased cardiac output (early), potentially diminished cardiac output (late), Elevated D-dimer, hypofibrinogenemia with or without bleeding, Azotemia Hepatic Transaminitis, hyperbilirubinemia, Headache, mental status changes, confusion, delirium, word finding difficulty or frank aphasia, hallucinations, tremor, dymetria, altered gait, seizures. In another embodiment, a cytokine storm is characterized by IL-2 release and lymphoproliferation. In another embodiment, a cytokine storm is characterized by increases in cytokines released by CAR T-cells. In another embodiment, a cytokine storm is characterized by increases in cytokines released by cells other than CAR T-cells.

In another embodiment, cytokine storm leads to potentially life-threatening complications including cardiac dysfunction, adult respiratory distress syndrome, neurologic toxicity, renal and/or hepatic failure, and disseminated intravascular coagulation.

A skilled artisan would appreciate that the characteristics of a cytokine release syndrome (CRS) or cytokine storm are estimated to occur a few days to several weeks following the trigger for the CRS or cytokine storm. In one embodiment, CAR T-cells are a trigger for CRS or a cytokine storm. In another embodiment, a trigger for CRS or a cytokine storm is not CAR T-cells.

In one embodiment, measurement of cytokine levels or concentration, as an indicator of cytokine storm, may be expressed as –fold increase, percent (%) increase, net increase or rate of change in cytokine levels or concentration. In another embodiment, absolute cytokine levels or concentrations above a certain level or concentration may be an indication of a subject undergoing or about to experience a cytokine storm. In another embodiment, absolute cytokine levels or concentration at a certain level or concentration, for example a level or concentration normally found in a control subject not undergoing CAR-T cell therapy, may be an indication of a method for inhibiting or reducing the incidence of a cytokine storm in a subject undergoing CAR T-cell.

A skilled artisan would appreciate that the term "cytokine level" may encompass a measure of concentration, a measure of fold change, a measure of percent (%) change, or a measure of rate change. Further, the methods for measuring cytokines in blood, saliva, serum, urine, and plasma are well known in the art.

In one embodiment, despite the recognition that cytokine storm is associated with elevation of several inflammatory cytokines, IL-6 levels may be used as a common measure of cytokine storm and/or as a common measure of the effectiveness of a treatment for cytokine storms. A skilled artisan would appreciate that other cytokines may be used as markers of a cytokine storm, for example any of TNF-α, IB-1α, IL-6, IL-8, IL-13, or INF-γ, or any combination above may be used as a marker of CRS or a cytokine storm. Further, that assay methods for measuring cytokines are well known in the art. A skilled artisan would appreciate that methods affecting a cytokine storm may similarly affect cytokine release syndrome (CRS).

In one embodiment, disclosed herein is a method of decreasing or inhibiting cytokine production in a subject experiencing cytokine release syndrome or a cytokine storm. In another embodiment, disclosed herein is a method of decreasing or inhibiting cytokine production in a subject vulnerable to experiencing cytokine release syndrome or a cytokine storm. In another embodiment, methods disclosed herein decrease or inhibit cytokine production in a subject experiencing cytokine release syndrome or a cytokine storm, wherein production of any cytokine or group of cytokines listed in Tables 1 and/or 2 is decreased or inhibited. In another embodiment, cytokine IL-6 production is decreased or inhibited. In another embodiment, cytokine IL-beta1 production is decreased or inhibited. In another embodiment, cytokine IL-8 production is decreased or inhibited. In another embodiment, cytokine IL-13 production is decreased or inhibited. In another embodiment, cytokine TNF-alpha production is decreased or inhibited. In another embodiment, cytokines IL-6 production, IL-1beta production, or TNF-alpha production, or any combination thereof is decreased or inhibited.

In one embodiment, cytokine release syndrome is graded. In another embodiment, Grade 1 describes cytokine release syndrome in which symptoms are not life threatening and require symptomatic treatment only, e.g., fever, nausea, fatigue, headache, myalgias, malaise. In another embodiment, Grade 2 symptoms require and respond to moderate intervention, such as oxygen, fluids or vasopressor for hypotension. In another embodiment, Grade 3 symptoms require and respond to aggressive intervention. In another embodiment, Grade 4 symptoms are life-threatening symptoms and require ventilator and patients display organ toxicity.

In another embodiment, a cytokine storm is characterized by IL-6 and interferon gamma release. In another embodiment, a cytokine storm is characterized by IL-6 release. In another embodiment, a cytokine storm is characterized by interferon gamma release. In another embodiment, a cytokine storm is characterized by release of any cytokine or combination thereof, listed in Tables 1 and 2. In another embodiment, a cytokine storm is characterized by release of any cytokine or combination thereof, known in the art.

In one embodiment, symptoms onset begins minutes to hours after the infusion begins. In another embodiment, symptoms coincide with peak cytokine levels.

In one embodiment, a method of inhibiting or reducing the incidence of a cytokine release syndrome (CRS) or a cytokine storm in a subject undergoing CAR T-cell cancer therapy comprises administering a pooled mononuclear apoptotic cell preparation or pharmaceutical composition thereof, as disclosed herein.

In one embodiment, a method of treating, preventing, ameliorating, inhibiting or reducing the incidence of a cytokine release syndrome (CRS) or a cytokine storm in a subject undergoing CAR T-cell cancer therapy does not affect the efficacy of the CAR T-cell therapy. In another embodiment, a method of treating, preventing, ameliorating, inhibiting or reducing the incidence of CRS or a cytokine storm in a subject undergoing CAR T-cell cancer therapy, does reduce the efficacy of the CAR T-cells therapy by more than about 5%. In another embodiment, a method of treating, preventing, ameliorating, inhibiting or reducing the incidence of CRS or a cytokine storm in a subject undergoing CAR T-cell cancer therapy, does reduce the efficacy of the CAR T-cells therapy by more than about 10%. In another embodiment, a method of treating, preventing, ameliorating, inhibiting or reducing the incidence of CRS or a cytokine storm in a subject undergoing CAR T-cell cancer therapy, does reduce the efficacy of the CAR T-cells therapy by more than about 15%. In another embodiment, a method of treating, preventing, ameliorating, inhibiting or reducing the incidence of CRS or a cytokine storm in a subject undergoing CAR T-cell cancer therapy, does reduce the efficacy of the CAR T-cells therapy by more than about 20%.

Any appropriate method of quantifying cytotoxicity can be used to determine whether activity in an immune cell modified to express a CAR remains substantially unchanged. For example, cytotoxicity can be quantified using a cell culture-based assay such as the cytotoxic assays described in the Examples. Cytotoxicity assays can employ dyes that preferentially stain the DNA of dead cells. In other cases, fluorescent and luminescent assays that measure the relative number of live and dead cells in a cell population can be used. For such assays, protease activities serve as markers for cell viability and cell toxicity, and a labeled cell permeable peptide generates fluorescent signals that are proportional to the number of viable cells in the sample. Kits for various cytotoxicity assays are commercially available from manufacturers such as Promega and Life Technologies. In another embodiment, a measure of cytotoxicity may be qualitative. In another embodiment, a measure of cytotoxicity may be quantitative. In a further embodiment a measure of cytotoxicity may be related to the change in expression of a cytotoxic cytokine.

Cytokine Release Associated with CAR T-Cell Therapy

In one embodiment, cytokine release occurs between a few days to 2 weeks after administration of immune therapy such as CAR T-cell therapy. In one embodiment, hypotension and other symptoms follow the cytokine release, i.e. from few days to few weeks. Therefore, in one embodiment, a pooled mononuclear apoptotic cell preparation or composition thereof, as disclosed herein in detail above, are administered to subjects at the same time as immune therapy as prophylaxis. In another embodiment, apoptotic cells or supernatant are administered to subjects 2-3 days after administration of immune therapy. In another embodiment, apoptotic cells or supernatant are administered to subjects 7 days after administration of immune therapy. In another embodiment, apoptotic cells or supernatant are administered to subjects 10 days after administration of immune therapy. In another embodiment, apoptotic cells or supernatant are administered to subjects 14 days after administration of immune therapy. In another embodiment, apoptotic cells or supernatant are administered to subjects 2-14 days after administration of immune therapy.

In another embodiment, a pooled mononuclear apoptotic cell preparation or composition thereof, as disclosed herein in detail above, are administered to subjects 2-3 hours after administration of immune therapy. In another embodiment, apoptotic cells or supernatant are administered to subjects 7 hours after administration of immune therapy. In another embodiment, apoptotic cells or supernatant are administered to subjects 10 hours after administration of immune therapy. In another embodiment, apoptotic cells or supernatant are administered to subjects 14 hours after administration of immune therapy. In another embodiment, apoptotic cells or supernatant are administered to subjects 2-14 hours after administration of immune therapy.

In an alternative embodiment, a pooled mononuclear apoptotic cell preparation or composition thereof, as disclosed herein in detail above, are administered to subjects prior to immune therapy as prophylaxis. In another embodiment, apoptotic cells or supernatant are administered to subjects 1 day before administration of immune therapy. In another embodiment, apoptotic cells or supernatant are administered to subjects 2-3 days before administration of immune therapy. In another embodiment, apoptotic cells or supernatant are administered to subjects 7 days before administration of immune therapy. In another embodiment, apoptotic cells or supernatant are administered to subjects 10 days before administration of immune therapy. In another embodiment, apoptotic cells or supernatant are administered to subjects 14 days before administration of immune therapy. In another embodiment, apoptotic cells or supernatant are administered to subjects 2-14 days before administration of immune therapy.

In another embodiment, a pooled mononuclear apoptotic cell preparation or composition thereof, as disclosed herein in detail above, are administered to subjects 2-3 hours before administration of immune therapy. In another embodiment, apoptotic cells or supernatant are administered to subjects 7 hours before administration of immune therapy. In another embodiment, apoptotic cells or supernatant are administered to subjects 10 hours before administration of immune therapy. In another embodiment, apoptotic cells or supernatant are administered to subjects 14 hours before administration of immune therapy. In another embodiment, apoptotic cells or supernatant are administered to subjects 2-14 hours before administration of immune therapy.

In another embodiment, a pooled mononuclear apoptotic cell preparation or composition thereof, as disclosed herein in detail above, may be administered therapeutically, once cytokine release syndrome has occurred. In one embodiment, apoptotic cells or supernatant may be administered once cytokine release leading up to or attesting to the beginning of cytokine release syndrome is detected. In one embodiment, apoptotic cells or supernatant can terminate the increased cytokine levels, or the cytokine release syndrome, and avoid its sequelae.

In another embodiment, a pooled mononuclear apoptotic cell preparation or composition thereof, as disclosed herein in detail above, may be administered therapeutically, at multiple time points. In another embodiment, administration of a pooled mononuclear apoptotic cell preparation or composition thereof, as disclosed herein in detail above, is at least at two time points described herein. In another embodiment, administration of a pooled mononuclear apoptotic cell preparation or composition thereof, as disclosed herein in detail above, is at least at three time points described herein.

In another embodiment, administration of a pooled mononuclear apoptotic cell preparation or composition thereof, as disclosed herein in detail above, is prior to CRS or a cytokine storm, and once cytokine release syndrome has occurred, and any combination thereof.

In one embodiment, the chimeric antigen receptor-expressing T-cell (CAR T-cell) therapy and a pooled mononuclear apoptotic cell preparation or composition thereof, as disclosed herein in detail above, are administered together. In another embodiment, the CAR T-cell therapy is administered after the apoptotic cell therapy or supernatant. In another embodiment, the CAR T-cell therapy is administered prior to the apoptotic cell therapy or supernatant. According to this aspect and in one embodiment, apoptotic cell therapy or supernatant is administered approximately 2-3 weeks after the CAR T-cell therapy. In another embodiment, apoptotic cell therapy or supernatant is administered approximately 6-7 weeks after the CAR T-cell therapy. In another embodiment, apoptotic cell therapy or supernatant is administered approximately 9 weeks after the CAR T-cell therapy. In another embodiment, apoptotic cell therapy is administered up to several months after CAR T-cell therapy.

Therefore, in one embodiment, a pooled mononuclear apoptotic cell preparation or composition thereof, as disclosed herein in detail above, are administered to subjects at the same time as immune therapy as prophylaxis. In another embodiment, apoptotic cells or supernatant are administered to subjects 2-3 days after administration of immune therapy. In another embodiment, apoptotic cells or supernatant are administered to subjects 7 days after administration of immune therapy. In another embodiment, apoptotic cells or supernatant are administered to subjects 10 days after administration of immune therapy. In another embodiment, apoptotic cells or supernatant are administered to subjects 14 days after administration of immune therapy. In another embodiment, apoptotic cells or supernatant are administered to subjects 2-14 days after administration of immune therapy.

In another embodiment, a pooled mononuclear apoptotic cell preparation or composition thereof, as disclosed herein in detail above, are administered to subjects 2-3 hours after administration of immune therapy. In another embodiment, apoptotic cells or supernatant are administered to subjects 7 hours after administration of immune therapy. In another embodiment, apoptotic cells or supernatant are administered to subjects 10 hours after administration of immune therapy. In another embodiment, apoptotic cells or supernatant are administered to subjects 14 hours after administration of immune therapy. In another embodiment, apoptotic cells or supernatant are administered to subjects 2-14 hours after administration of immune therapy.

In an alternative embodiment, a pooled mononuclear apoptotic cell preparation or composition thereof, as disclosed herein in detail above, are administered to subjects prior to immune therapy as prophylaxis. In another embodiment, apoptotic cells or supernatant are administered to subjects 1 day before administration of immune therapy. In another embodiment, apoptotic cells or supernatant are administered to subjects 2-3 days before administration of immune therapy. In another embodiment, apoptotic cells or supernatant are administered to subjects 7 days before administration of immune therapy. In another embodiment, apoptotic cells or supernatant are administered to subjects 10 days before administration of immune therapy. In another embodiment, apoptotic cells or supernatant are administered to subjects 14 days before administration of immune therapy. In another embodiment, apoptotic cells or supernatant are administered to subjects 2-14 days before administration of immune therapy.

In another embodiment, a pooled mononuclear apoptotic cell preparation or composition thereof, as disclosed herein in detail above, are administered to subjects 2-3 hours before administration of immune therapy. In another embodiment, apoptotic cells or supernatant are administered to subjects 7 hours before administration of immune therapy. In another embodiment, apoptotic cells or supernatant are administered to subjects 10 hours before administration of immune therapy. In another embodiment, apoptotic cells or supernatant are administered to subjects 14 hours before administration of immune therapy. In another embodiment, apoptotic cells or supernatant are administered to subjects 2-14 hours before administration of immune therapy.

In another embodiment, a pooled mononuclear apoptotic cell preparation or composition thereof, as disclosed herein in detail above, may be administered therapeutically, once cytokine release syndrome has occurred. In one embodiment, a pooled mononuclear apoptotic cell preparation or composition thereof, as disclosed herein in detail above, may be administered once cytokine release leading up to or attesting to the beginning of cytokine release syndrome is detected. In one embodiment, apoptotic cells or supernatant can terminate the increased cytokine levels, or the cytokine release syndrome, and avoid its sequelae.

In another embodiment, a pooled mononuclear apoptotic cell preparation or composition thereof, as disclosed herein in detail above, may be administered therapeutically, at multiple time points. In another embodiment, administration of a pooled mononuclear apoptotic cell preparation or composition thereof, as disclosed herein in detail above, is at least at two time points described herein. In another embodiment, administration of a pooled mononuclear apoptotic cell preparation or composition thereof, as disclosed herein in detail above, is at least at three time points described herein. In another embodiment, administration of a pooled mononuclear apoptotic cell preparation or composition thereof, as disclosed herein in detail above, is prior to CRS or a cytokine storm, and once cytokine release syndrome has occurred, and any combination thereof.

In one embodiment, the chimeric antigen receptor-expressing T-cell (CAR T-cell) therapy and a pooled mononuclear apoptotic cell preparation or composition thereof, as disclosed herein in detail above are administered together. In another embodiment, the CAR T-cell therapy is administered after the pooled mononuclear apoptotic cell preparation or composition thereof, as disclosed herein in detail above. In another embodiment, the CAR T-cell therapy is administered prior to the pooled mononuclear apoptotic cell preparation or composition thereof, as disclosed herein in detail above. According to this aspect and in one embodiment, a pooled mononuclear apoptotic cell preparation or composition thereof, as disclosed herein in detail above, is administered approximately 2-3 weeks after the CAR T-cell therapy. In another embodiment, apoptotic cell therapy or supernatant is administered approximately 6-7 weeks after the CAR T-cell therapy. In another embodiment, apoptotic cell therapy or supernatant is administered approximately 9 weeks after the CAR T-cell therapy. In another embodiment, apoptotic cell therapy is administered up to several months after CAR T-cell therapy.

In one embodiment, CAR T-cells are heterologous to the subject. In one embodiment, CAR T-cells are obtained from one or more donors. In one embodiment, CAR T-cells are obtained from one or more bone marrow donors. In another embodiment, CAR T-cells are obtained from one or more blood bank donations. In one embodiment, the donors are matched donors. In one embodiment, CAR T-cells are universal allogeneic CAR T-cells. In another embodiment, CAR T-cells are syngeneic CAR T-cells. In another embodiment, CAR T-cells are from unmatched third party donors. In another embodiment, CAR T-cells are from pooled third party donor T-cells. In one embodiment, the donor is a bone marrow donor. In another embodiment, the donor is a blood bank donor. In one embodiment, CAR T-cells of the compositions and methods as disclosed herein comprise one or more MHC unrestricted tumor-directed chimeric receptors. In one embodiment, non-autologous T-cells may be engineered or administered according to protocols known in the art to prevent or minimize autoimmune reactions, such as described in U.S. Patent Application Publication No. 20130156794, which is incorporated herein by references in its entirety.

In another embodiment, CAR T-cells are autologous to the subject. In one embodiment, the patient's own cells are used. In this embodiment, if the patient's own cells are used, then the CAR T-cell therapy is administered after the pooled mononuclear apoptotic cell preparation or composition thereof.

In one embodiment, the preparation is administered in a local rather than systemic manner, for example, via injection of the preparation directly into a specific region of a patient's body. In another embodiment, a specific region comprises a tumor or cancer.

In certain embodiments, a CAR T-cell therapy comprises administering a composition disclosed herein comprising CAR T-cells and a pooled mononuclear apoptotic cell preparation or composition thereof.

Cytokine Release Associated with Non CAR T-Cell Applications

In one embodiment, disclosed herein is a method of decreasing or inhibiting cytokine production in a subject experiencing cytokine release syndrome or cytokine storm or vulnerable to cytokine release syndrome or cytokine storm, comprising the step of administering a composition comprising a pooled mononuclear apoptotic cell preparation or composition thereof, as disclosed herein in detail above, to said subject, wherein said administering decreases or inhibits cytokine production in said subject. In another embodiment, decrease or inhibition of cytokine production is compared with a subject experiencing cytokine release syndrome or cytokine storm or vulnerable to cytokine release syndrome or cytokine storm and not administered a pooled mononuclear apoptotic cell preparation or composition thereof, as disclosed herein in detail above. In another embodiment, methods for decreasing or inhibiting cytokine production decrease or inhibit pro-inflammatory cytokine production. In another embodiment, methods for decreasing or inhibiting cytokine production decrease or inhibit production of at least one pro-inflammatory cytokine. In another embodiment, methods for decreasing or inhibiting cytokine production decrease or inhibit production of at least cytokine IL-6. In another embodiment, methods for decreasing or inhibiting cytokine production decrease or inhibit production of at least cytokine IL-1beta. In another embodiment, methods for decreasing or inhibiting cytokine production decrease or inhibit production of at least cytokine TNF-alpha. In another embodiment, methods disclosed herein for decreasing or inhibiting cytokine production, result in reduction or inhibition of production of cytokines IL-6, IL-1β, or TNF-α, or any combination in said subject compared with a subject experiencing cytokine release syndrome or cytokine storm or vulnerable to cytokine release syndrome or cytokine storm and not administered a pooled mononuclear apoptotic cell preparation or composition thereof, as disclosed herein in detail above.

Cancers or tumors may also affect the absolute level of cytokines including pro-inflammatory cytokines. The level of tumor burden in a subject may affect cytokine levels, particularly proinflammatory cytokines. A skilled artisan would appreciate that the phrase "decrease or inhibit" or grammatical variants thereof may encompass fold decrease or inhibition of cytokine production, or a net decrease or inhibition of cytokine production, or percent (%) decrease or inhibition, or may encompass a rate of change of decrease or inhibition of a cytokine production.

In another embodiment, disclosed herein is a method of decreasing or inhibiting cytokine production in a subject experiencing cytokine release syndrome or cytokine storm or vulnerable to cytokine release syndrome or cytokine storm comprising the step of administering a pooled mononuclear apoptotic cell preparation or composition thereof, as disclosed herein in detail above to said subject.

In another embodiment, disclosed herein is a method of decreasing or inhibiting cytokine production in a subject experiencing cytokine release syndrome or cytokine storm or vulnerable to cytokine release syndrome or cytokine storm comprising the step of administering a pooled mononuclear apoptotic cell preparation or composition thereof, as disclosed herein in detail above to said subject.

In one embodiment, an infection causes the cytokine release syndrome or cytokine storm in the subject. In one embodiment, the infection is an influenza infection. In one embodiment, the influenza infection is H1N1. In another embodiment, the influenza infection is an H5N1 bird flu. In another embodiment, the infection is severe acute respiratory syndrome (SARS). In another embodiment, the subject has Epstein-Barr virus-associated hemophagocytic lymphohistiocytosis (HLH). In another embodiment, the infection is sepsis. In one embodiment, the sepsis is gram-negative. In another embodiment, the infection is malaria. In another embodiment, the infection is an Ebola virus infection. In another embodiment, the infection is variola virus. In another embodiment, the infection is a systemic Gram-negative bacterial infection. In another embodiment, the infection is Jarisch-Herxheimer syndrome.

In one embodiment, the cause of the cytokine release syndrome or cytokine storm in a subject is hemophagocytic lymphohistiocytosis (HLH). In another embodiment, HLH is sporadic HLH. In another embodiment, HLH is macrophage activation syndrome (MAS). In another embodiment, the cause of the cytokine release syndrome or cytokine storm in a subject is MAS.

In one embodiment, the cause of the cytokine release syndrome or cytokine storm in a subject is chronic arthritis. In another embodiment, the cause of the cytokine release syndrome or cytokine storm in a subject is systemic Juvenile Idiopathic Arthritis (sJIA), also known as Still's Disease.

In one embodiment, the cause of the cytokine release syndrome or cytokine storm in a subject is Cryopyrin-associated Periodic Syndrome (CAPS). In another embodiment, CAPS comprises Familial Cold Auto-inflammatory Syndrome (FCAS), also known as Familial Cold Urticaria (FCU). In another embodiment, CAPS comprises Muckle-Well Syndrome (MWS). In another embodiment, CAPS comprises Chronic Infantile Neurological Cutaneous and Articular (CINCA) Syndrome. In yet another embodiment, CAPS comprises FCAS, FCU, MWS, or CINCA Syndrome, or any combination thereof. In another embodiment, the cause of the cytokine release syndrome or cytokine storm in a subject is FCAS. In another embodiment, the cause of the cytokine release syndrome or cytokine storm in a subject is FCU. In another embodiment, the cause of the cytokine release syndrome or cytokine storm in a subject is MWS. In another embodiment, the cause of the cytokine release syndrome or cytokine storm in a subject is CINCA Syndrome. In still another embodiment, the cause of the cytokine release syndrome or cytokine storm in a subject is FCAS, FCU, MWS, or CINCA Syndrome, or any combination thereof.

In another embodiment, the cause of the cytokine release syndrome or cytokine storm in a subject is a cryopyrinopathy comprising inherited or de novo gain of function mutations in the NLRP3 gene, also known as the CIAS1 gene.

In one embodiment, the cause of the cytokine release syndrome or cytokine storm in a subject is a hereditary auto-inflammatory disorder.

In one embodiment, the trigger for the release of inflammatory cytokines is a lipopolysaccharide (LPS), Gram-positive toxins, fungal toxins, glycosylphosphatidylinositol (GPI) or modulation of RIG-1 gene expression.

In another embodiment, the subject experiencing cytokine release syndrome or cytokine storm does not have an infectious disease. In one embodiment, the subject has acute pancreatitis. In another embodiment, the subject has tissue injury, which in on embodiment, is severe burns or trauma. In another embodiment, the subject has acute respiratory distress syndrome. In another embodiment, the subject has cytokine release syndrome or cytokine storm secondary to agent use. In another embodiment, the subject has cytokine release syndrome or cytokine storm secondary to toxin inhalation.

In another embodiment, the subject has cytokine release syndrome or cytokine storm secondary to receipt of immunotherapy, which in one embodiment is immunotherapy with superagonistic CD28-specific monoclonal antibodies (CD28SA). In one embodiment, the CD28SA is TGN1412. In another embodiment, the immunotherapy is CAR T-cell therapy. In another embodiment, the immunotherapy is dendritic cell therapy.

In another embodiment, a pooled mononuclear apoptotic cell preparation or composition thereof, as disclosed herein in detail above, may be used to control cytokine release syndrome or cytokine storm that results from administration of a pharmaceutical composition.

In another embodiment, a pooled mononuclear apoptotic cell preparation or composition thereof, as disclosed herein in detail above, may be used to control cytokine release syndrome or cytokine storm that results from administration of an antibody. In one embodiment, the antibody is monoclonal. In another embodiment, the antibody is polyclonal. In one embodiment, the antibody is rituximab. In another embodiment, the antibody is Orthoclone OKT3 (muromonab-CD3). In another embodiment, the antibody is alemtuzumab, tositumomab, CP-870,893, LO-CD2a/BTI-322 or TGN1412.

In another embodiment, examples of diseases for which control of inflammatory cytokine production can be beneficial include cancers, allergies, any type of infection, toxic shock syndrome, sepsis, any type of autoimmune disease, arthritis, Crohn's disease, lupus, psoriasis, or any other disease for which the hallmark feature is toxic cytokine release that causes deleterious effects in a subject.

The following examples are presented in order to more fully illustrate the embodiments. They should in no way be construed, however, as limiting the broad scope.

EXAMPLES

Example 1: Production of Single Source Early Apoptotic Cells

An early apoptotic cell product containing apoptotic cells produced from a mononuclear enriched cell fraction from a sibling HLA-matched donor has been described in detail in WO 2014/087408, see for example the Examples section, wherein the WO 2014/087408 application is incorporated herein in full. Eligibility criteria for donors included the following: adult male or female donors, 18-65 years of age; the donor and recipient must have at least a 7/8 HLA match at the HLA A, B, C, and DR loci; above 40 kg; willingness to donate hematopoietic blood mononuclear cells for the generation of early apoptotic cells in addition to the donation for the HSCT. Eligible donors returned to the clinic approximately at Day −19 for peripheral blood mononuclear harvesting using leukapheresis procedure (Cobe® Spectra™, Gambro BCT, Lakewood, CO, USA) according to the local SOPs.

During the approximate 2.5 hours of leukapheresis, 7 L of blood was processed and mononuclear cells were collected at room temperature into a transfer pack. The estimated yield of the enriched mononuclear cell fraction from a donor was $1.0 \times 10^{10}$ cells in an estimated volume of 100-140 ml. The mean percentage of mononuclear cell fraction in the cell collections resulting from the leukapheresis was 88±8% (ranging between 65-96%). Cell yields varied depending on the donor variability.

The collected mononuclear enriched cell fraction from the HLA-matched donors underwent sequential processes for inducing early apoptosis through a multistep procedure including freezing and thawing the cells followed by incubation with methylprednisolone (Details below). The early apoptotic final cell suspension contained at least 40% of early apoptotic cells. The cell suspension for infusion was prepared under current Good Manufacturing Procedures (cGMP). Infusions were performed 24-30 hours before HSCT and within 8 hours of completion of preparation. Cells were stored at 2-8° C. until administered.

Incubation with Methylprednisolone

During preparation of the early apoptotic cell product, the enriched mononuclear cell fraction was incubated in an apoptosis induction medium comprising 50 µg/mL of methylprednisolone for six hours. At the end of apoptosis induction the cells were washed and re-suspended in PBS. Final volume of the early apoptotic cell product after collection of quality control samples was 300 ml. The residual amount of methylprednisolone in the supernatant of the early apoptotic cell final product was determined on final products prepared from three runs. Methylprednisolone levels were determined using reversed-phase liquid chromatography (HPLC). Assays were qualified and performed by Spectrolab Analytical Laboratory, Rehovot, Israel. The levels of residual methyl prednisolone in the early apoptotic cell final product are presented in Table 3 below.

TABLE 3

Residual Methylprednisolone in Early Apoptotic Final Cell Product

| Total amount of Methyl prednisolone in final dose | Residual concentration of Methyl prednisolone | Cohort No. (Dose: cells/kg) | Total number of cells in Early Apoptotic Final Product dose | Run No. (Batch ID No.) |
|---|---|---|---|---|
| 1.11 mg | 3.7 mg/L | 1 ($3.5 \times 10^7$ cells/kg) | $2.45 \times 10^9$ | Run 1 (Batch ID: 0021) |
| 3.3 mg | 11.2 mg/L | 3 ($1.4 \times 10^8$ cells/kg) | $7 \times 10^9$ | Run 2 (Batch ID: 0024) |
| 6.57 mg | 21.9 mg/L | 4 ($2.1 \times 10^8$ cells/kg) | $11.34 \times 10^9$ | Run 3 (Batch ID: 0022) |

The range of residual methylprednisolone concentration in the final product was 3.7 mg/L in the lowest cell dose of the early apoptotic cell product and 21.9 mg/L in the highest cell dose. The range of total methylprednisolone in the final dose was 1.11-6.57 mg in correlation to the early apoptotic dose. The results demonstrated that the amount of methylprednisolone present in the early apoptotic cell product, including in the highest cohort, is negligible relative to the dose of methylprednisolone received by a patient as part of the general treatment protocol during a bone marrow transplantation.

Manufacturing Process Description

Collection of enriched mononuclear cell fractions and plasma from healthy, eligible donors was performed at apheresis centers via apheresis machine and sterile, disposable kit. Cells were collected into a cell collection bag and autologous plasma into a plasma collection bag. The estimated yield of the enriched mononuclear cell fraction from a donor was expected to be approximately $1.5 \times 10^{10}$ cells in 250-350 mL. During apheresis approximately 400-600 mL of donor autologous plasma was collected as well. The collected cells and plasma were stored at room temperature until further processing and are prepared for cryopreservation on average within 3-6 hours from collection completion.

Freezing Procedure:

Cells:

Freezing media was prepared in bags and the freezing procedure performed in a closed system under cGMP condition.

Media for cell freezing was prepared fresh on the day of apheresis, which was pre-cooled in advance and composed of the following formula:

Mix1: PlasmaLyte A for injection pH 7.4, 5% Human Serum Albumin and 5% Anticoagulant Citrate Dextrose (ACD) formula A solution inoculated with 10 U\ml heparin.

Mix 2: PlasmaLyte A for injection pH 7.4, 10% DMSO and 5% ACD formula A solution inoculated with 10 U\ml heparin.

Following completion of the leukapheresis procedure, cells were washed with pre-cooled PlasmaLyte A for injection pH 7.4, supplemented with 5% ACD formula A solution inoculated with 10 U\ml heparin. Following washing, the supernatant was removed and the cell pellet resuspended with Mix1. Cells were then counted and analyzed for viability

TABLE 4

Specifications for the collected cells during collection and prior to freezing processes

| Test | Method | Specification |
|---|---|---|
| Cell count | Hematology Analyzer | At least $10^9$ total cells |
| Cell viability | Trypan blue positive cells counting via light microscope | At least 85% trypan blue negative cells |
| Identity/ purity | Hematology Analyzer | At least 50% mononuclear cells |

According to cell count, the total number of cells collected was calculated. The number of cell freezing bags was determined according to a concentration of $50$-$65 \times 10^6$ cells\ml. Mix1 is then further added to cells to a volume of 50% of final freezing volume. Cells were then transferred to freezing bag, and Mix2 was added to each bag to a volume of 50% of final freezing volume.

Each freezing bag was placed in a pre-cooled freezing cassette and transferred to $-18$-$(-25)°$ C. freezer for 2 hours. After two hours at $-18$-$(-25)°$ C., the cassettes transferred to $-80°$ C. freezer for additional two hours. Following two hours at $-80°$ C., the cassettes were transferred to a liquid nitrogen freezer for long term storage until needed for manufacturing.

Plasma:

Plasma was divided to 50 ml aliquots stored at 150 ml transfer pack containers (designated as "plasma freezing bags").

Following completion of aliquoting, all plasma freezing bags were transferred to $-80°$ C. freezer for 2 hours. Following 2 hours at $-80°$ C., plasma freezing bags were transferred to long term storage at $-18$-$(-25)°$ C. freezer.

Apoptotic Cell (Early Apoptosis) Manufacturing

The process was carried out in a closed system under cGMP conditions.

Manufacturing Process

Preparation of Media:

The manufacturing process includes three media types, all made in bags:

(1) Thawing wash media (2) Induction solution (3) Lactated ringer's solution

The Thawing Wash Media was used for cell washing following thawing. The final formulation of the Thawing Wash Media was RPMI 1640 supplemented with 2 mM L-glutamine, 10 mM Hepes and 5% ACD formula A solution inoculated with 10 U\ml heparin. Induction solution was used for apoptosis induction and its formulation is RPMI 1640 supplemented with 2 mM L-glutamine and 10 mM Hepes, 10% autologous plasma, 50 µg\ml Methylpredniso lone and 5% ACD formula A solution inoculated with 10 U\ml heparin.

Media was pre-warmed before use.

Thawing and Apoptosis Induction:

Freezing bags containing frozen cell concentrates were transferred from the liquid nitrogen storage freezer and immersed in a 35-380 C circulating water bath. The cell concentrates were thawed to completion with gentle mixing for approximately 120 seconds. Cell freezing bags were then removed from the water bath and disinfected by rinsing in 70% isopropanol and wiped dry.

The thawed freezing bag was connected to pre-warmed thawing wash media bag and the thawed cells transferred to the transfer pack by gravity flow. This process was repeated for each additional freezing bag.

The suspended thawed cells were centrifuged at 290×g for 10 min at 25° C. At the end of washed cells were carefully removed from the centrifuge and supernatant removed.

Washed cells were resuspended with pre-warmed Induction solution and mixed gently until a homogeneous suspension was formed.

Cells were then counted and analyzed for viability.

TABLE 5

In Process Control tests for thawed collected cells pre-induction

| Test | Test method | Specification |
|---|---|---|
| Cell count | Hematology Analyzer | Number of cells per sampled bag needs to be $-30\% \leq$ or $\leq +10\%$ from frozen. |
| Cell viability | Trypan blue or equivalent | At least 85% viable cells |

Based on cell counts and dose of cells needed for eligible subjects, the appropriate number of Cell Culture Bags were prepared such that the volume of each bag would be maintained within volume range as determined by manufacturer. Cells were brought to a final concentration of approximately $5 \times 10^6$ cells\ml with induction solution, and cells were then distributed evenly to as many needed Cell Culture Bags.

Cell Culture Bags containing cells with induction solution were incubated for 6 hours at 37° C., 5% $CO_2$.

Volume Reduction and Final Product Final Formulation:

Volume reduction and media exchange to administration buffer (Lactated Ringer's solution) was performed automatically using LOVO cell processing system.

LOVO instrument was loaded with sterile, disposable kit. Administration buffer and cell culture bags were connected sterilely to the kit. Cell culture bag containing apoptotic cells were processed via LOVO using 5:1 reduction rate, while final formulation was performed directly into delivery bag with cold Lactated Ringer's solution to a final volume of 450-500 ml.

Collection of Samples for Release and Post-Release Testing

The content of the final product delivery bag was adequately mixed to ensure a homogeneous mixture. Approximately 10% was removed for release testing as detailed in table 6 below:

TABLE 6

Early apoptotic Cellsl Drug Product Release and post release Test Methods and specifications

| Test | Method | Specification |
|---|---|---|
| Appearance | Visual inspection | White to pale red homogenous cell suspension minor amount and small white cell clusters may be visible |

TABLE 6-continued

Early apoptotic Cellsl Drug Product Release and post release
Test Methods and specifications

| Test | Method | Specification |
|---|---|---|
| Cell count | Hematology Analyzer | 140 × $10^6$ ± 20% patient weight |
| Cell viability | Flow cytometric analysis of propiclium iodide negative cells | At least 85% viable |
| Identity: Apoptosis | Flow cytometric analysis of annexin V positive, propidium iodide negative cells | At least 40% apoptotic cells (An+PI−) |
| Gram Stain | | Negative |
| Sterility | Direct sterility test | Negative growth at 14 days |
| Endotoxin | | Less than 1 EU/mL |
| Potency | Monocytes assay (pre-release testing) | Inhibition of LPS upregulation of HLA-DR >20% in at least one ratio of Early apoptotic Cellsl: CD14+ |
| Identity/ Purity | Flow cytometric analysis of CD3, CD19, CD14, CD56, CD15high | FSC/SSC WBCs 100%<br>CD3 report results<br>CD19 report results<br>CD14 report results<br>CD56 report results<br>CD15high < 5% |

The final product data is presented in Table 7.

TABLE 7

Results from Lots manufactured by Enlivex: Cell count, viability, identity/purity and apoptosis

| Test | Specification | | At apheresis of mononuclear enriched fraction | At Thaw | Early Apoptotic Cells Time 0 h | Early Apoptotic Cells Time 24 h Storage | Early Apoptotic Cells Time 48 h Storage |
|---|---|---|---|---|---|---|---|
| Change in Total Cell Count Percent change (min-max) | >35.0% | | 100 | 90.0 (85.1-95.6) | 70.1 (66.5-74.8) | 68.0 (64.7-69.8) | 67.0 (64.8-68.8) |
| Changes in Apoptotic Cell Percent change Range (min-max) | 90.0 ± 10.0% | | | | 100 | 97.2 (92.4-99.6) | 95.8 (92.5-98.3) |
| Cell viability PI exclusion Percent viable Range (min-max) | >85.0% | | 99.8 (99.5-99.9) | 97.2 (95.5-98.4) | 94.0 (93.4-94.5) | 93.1 (91.7-94.9) | 93.3 (92.0-94.9) |
| Identity/ Purity Analysis of cell phenotype Average (%) Range (min-max) | CD3 (T cells): | | 69.3 (63.0-74.0) | 66.5 (60.1-70.1) | 62.3 (60.0-65.4) | 62.8 (60.0-65.5) | 62.9 (59.8-66.0) |
| | CD19 (B cells): | | 10.8 (7.7-13) | 9.8 (8.6-12.0) | 10.9 (9.0-12.8) | 12.4 (11.5-13.2) | 12.7 (11.9-13.5) |
| | CD14 (monocytes): | | 8.9 (3.4-11.0) | 14.0 (8.8-22.1) | 14.3 (9.2-18.5) | 12.1 (8.5-15.6) | 12.5 (8.5-16.4) |
| | CD15 high (granulocytes): | | 1.2 (0.8-2.3) | 0.46 (0.18-0.69) | 0.18 (0.09-0.3) | 0.06 (0.01-0.11) | 0.04 (0.0-0.08) |
| | CD 56 (NK): | | 13.2 (5.6-19.7) | 10.1 (6.6-14.2) | 7.6 (5.1-10.4) | 8.5 (7.1-9.9) | 8.9 (6.9-10.8) |
| Apoptosis (Annexin + PI−) Average (%) Range (min-max) | Total | CD3 | 10.1 (6.6-14.2) | ND | 55.3 44.8 (52.4-60.7) (38.0-62.2) | 50.9 38.7 (47.4-56.5) (37.9-39.5) | 56.7 53.8 (54.1-60.4) (50.9-56.7) | 59.7 57.2 (57.1-63.3) (56.9-57.6) |
| | | CD19 | | | 53.8 (27.8-83.8) | 47.2 (40.7-54.0) | 51.4 (45.0-57.7) | 49.5 (45.0-57.7) |
| | | CD14 | | | 98.9 (97.5-100) | 98.5 (97.9-99.0) | 99.1 (99.0-99.2) | 98.1 (97.5-98.7) |
| | | CD56 | | | 67.5 (51.7-93.2) | 65.8 (49.5-82.0) | 65.2 (61.2-69.2) | 58.5 (50.5-66.4) |

Release Product for Infusion:

Once the final product passed the release tests, the final early apoptotic cell product was stored at 2-8° C. and transported to the clinical center for patient administration. The product will be administered using an infusion set with not less than 200 micron filter. Based on preliminary stability data, the expiration time for the final early apoptotic cell product was 48 hours from the time of preparation.

Example 2: Use of Pooled Apoptotic Cell Preparation in GvHD Leukemia/Lymphoma Models In the following preliminary work, the effect of the same infusion in GvHD leukemia/lymphoma models was examined. The safety and efficacy of an irradiated multiple donor single apoptotic cell infusion (a pooled mononuclear irradiated apoptotic cell preparation) for the prevention of acute GvHD in mice undergoing bone marrow transplantation (BMT) was examined. In this model, BMT rescued irradiated mice (80-100%).

The question regarding the possible loss of graft versus leukemia (GvL) effect arises in every successful treatment that potentially avoids high grade aGVHD, since this effect was found to correlate with the severity of GVHD.

Methods

Apoptotic cells were prepared as per Example 1 above, except that in the current experiments, preparation was done simultaneously from 4 donors. Following preparation from 4 donors, the cell preparations were combined at the last step (prior to irradiation), irradiated immediately after, and injected immediately after irradiation. Irradiation was at 25 Gy.

Results

Figure 2:
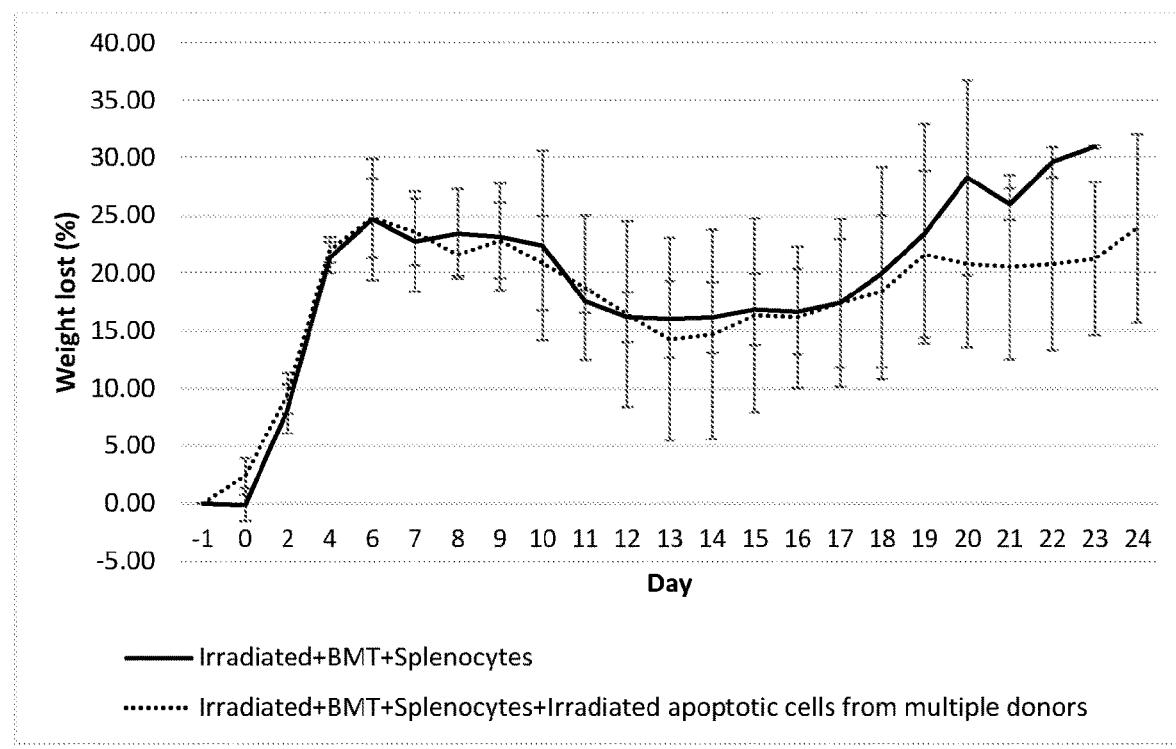
FIG. 2 presents a graph showing the clear effect ($p<0.01$) of a single apoptotic cell preparation injection from multiple individual donors (blue) on percentage of weight loss of the 2 compared groups.

The two graphs presented in FIGS. 1 and 2, show the clear effect ($p<0.01$) of a single injection of apoptotic cell from multiple individual donors (triangles), both on survival and weight loss. FIG. 1 is a Kaplan-Meier survival curve in a GvHD mouse model that was treated with a single dose irradiated apoptotic cells from multiple individual donors where survival was significantly ameliorated. FIG. 2 is percentage of weight loss of the 2 compared groups that follows and correlate to the findings of FIG. 1.

In summary, the single infusion of multiple-donor irradiated apoptotic cells successfully and significantly improved life expectancy in a mouse model of GvHD.

Example 3: Stability Criteria for Apoptotic Cells from Multiple Individual Donors The objective of this study is to develop stability criteria for apoptotic cells from multiple individual donors with comparability studies to non-irradiated HLA-matched apoptotic cells (Mevorach et al. (2014) Biology of Blood and Marrow Transplantation 20(1): 58-65; Mevorach et al. (2015) Biology of Blood and Marrow Transplantation 21(2): S339-S340).

Apoptotic cell final product preparations will be evaluated for cell number, viability, apoptotic phenotype and potency after storage at 2 to 8° C. for 8, 24, 48, and 60 hours with sampling at each time point. Apoptotic cell final product lots will be prepared following standard operating procedures (SOPs) (Example 1; Example 5) and batch records (BRs; i.e., specific manufacturing procedures). For potency evaluation, samples of early apoptotic cell preparation final product lots will be tested for inhibition of lipopolysaccharide (LPS) induced upregulation of MHC-II expression on immature dendritic cells (time points 0-24 h) or monocytes (time points 0-6) and will be performed according to SOPs and recorded on BR. These series of test will be performed on pooled and non-pooled products that are in preparations originating from multiple individual donors and from single donors, respectively.

In addition, flow cytometric analysis of CD3 (T cells), CD19 (B cells), CD14 (monocytes), $CD15^{high}$ (granulocytes) and CD56 (NK cells) will be documented. The aims of these studies are to demonstrate consistency with a narrow range of results. Preliminary results are consistent with these goals and no deviations from the SOP are noted and no technical problems are reported. However, further studies are needed in order to conclude the range and stability of effective treatment. Preliminary results show equivalence in all these parameters (Example 6 Table 3). Further, single donor stability studies showed stability at least through a 48 hour period (Example 5; cell preparation).

Example 4: Safety & Efficacy of Multiple Donor Irradiated Apoptotic Cells as Prophylaxis for Acute Graft-Versus-Host Disease Objective: A phase ½a, multicenter, open-label study evaluating the safety, tolerability and preliminary efficacy of a single dose administration of irradiated apoptotic cells, from multi-, unmatched-donors, for the prevention of graft versus host disease in hematopoietic malignancies in human leukocyte antigen-matched, related and unrelated patients undergoing allogeneic hla-matched hematopoietic stem cell transplantation Primary Objective: To determine safety and tolerability of multiple donor irradiated apoptotic cell treatment.

Secondary Objective: To determine efficacy of irradiated apoptotic cells from multiple individual donors as prophylaxis measure for acute GVHD (aGVHD) in patients with hematopoietic malignancies scheduled to undergo hematopoietic stem cell transplantation (HSCT). For the purposes of this study, HSCT can be either bone marrow transplant (BMT) or peripheral blood stem cell transplantation (PBSCT).

Therapeutic Indication: Graft vs. Host Disease (GVHD) post-transplantation in hematopoietic malignancies in human leukocyte antigen (HLA)-matched, related and unrelated patients Study Design: This is an open labeled study, multi-center, phase-½a study in patients diagnosed with hematopoietic malignancies scheduled to undergo HSCT (either bone marrow transplantation or peripheral blood stem cell transplantation) from an HLA-matched related or unrelated donor, following either full myeloablative or reduced intensity myeloablative conditioning regimens.

After a signing of informed consent by recipient patient, donors screening period and cell collection before initiating conditioning regimen, eligible recipient patients will be assigned (stratified by prophylactic treatment and related versus non-related transplant donors in 1:1 ratio to receive intravenous (IV) injection 12-36 hours prior to HSCT transplantation to either:

Investigational Arm: single dose of $140 \times 10^6 \pm 20\%$ cell/kg from multiple individual donors of irradiated early apoptotic cells/kg body weight in phosphate buffer solution (PBS).

All patients will also be treated with the institutional standard of care (SOC) immunosuppressive regimen: cyclosporine/methotrexate or tacrolimus/methotrexate for full myeloablation and mycofenolate/cyclosporine or mycophenolate/tacrolinus for reduced intensity. Patients will be hospitalized as medically indicated.

Patients will be followed up for 180 days for the secondary efficacy endpoint and for 1 year for the primary safety and tertiary efficacy endpoints. Number of visits for patients participating in this study will be comparable to those customary for patients in their condition. For donor, study specific visit will be for apheresis procedure during the screening period.

As these patients have many underlying medical conditions and may experience symptoms compatible with aGVHD, it may be difficult to absolutely determine if toxicity is related to apoptotic cells or not although basic data exist from a former phase 1-2a study using apoptotic cells for GvHD prophylaxis (Mevorach et al. (2014) Biology of Blood and Marrow Transplantation 20(1): 58-65) Single Infusion of Donor Mononuclear Early Apoptotic Cells as Prophylaxis for Graft-versus-Host Disease in Myeloablative HLA-Matched Allogeneic Bone Marrow Transplantation: A Phase I/IIa Clinical Trial. BBMT 20(1)58-65).

Data Safety Monitoring Board (DSMB) will meet as specified in the DSMB charter, including at the time of the scheduled interim analysis (180 days) assuming no safety concerns were raised beforehand.

Study Procedures:

The study will comprise of screening, treatment and follow-up periods.

1. Screening Period (Day −60 to Day −2)

Potential recipient patients will sign informed consent prior to conduct of any study related procedures. The standard assessments before approval, will be performed by the transplantation center for the donor during the screening period and usually include: demographic data, medical history, HLA match status verification (no matching is needed), physical examination, height and weight, vital signs, pregnancy test (all women), hematology, blood chemistry, infectious disease screen, ECG and urinalysis.

The recipients (study patients) will undergo the following assessments during the screening period: demographic data, medical history, Karnofsky performance status, HLA match verification, physical exam, height and weight, vital signs, pregnancy test (all women), ECG, pulmonary function test, hematology, blood chemistry, coagulation markers, infectious disease screen, and urinalysis.

After the initial screening evaluations, if recipient is eligible to participate in the study, the recipient patient will be assigned on the first day of the conditioning regimen to receive single IV infusion of $140 \times 10^6 \pm 20\%$ cell/kg of multiple donor apoptotic cells. The conditioning regimen to be completed on the day before or day of Apoptotic Cell infusion scheduled for Study Day −1.

Apoptotic cell dosage will be calculated for each recipient patient and presumed apheresis collection number and number of donors will be decided accordingly.

For peripheral stem cell transplant donors: Between Days −6 to −1, the donor will receive one or more once daily injections of G-CSF to mobilize progenitor cells and on Day 0 will undergo apheresis to produce donor hematopoietic blood stem cells for transplantation. Preparation of the hematopoietic blood stem cells for bone marrow transplantation will be performed in accordance with the center's standard practice by trained hospital staff. The hematopoietic blood stem cells for HSCT will not be manipulated or T cell-depleted prior to administration.

For bone marrow transplant donors: Bone marrow will harvested and prepared per center standard practice and will not be otherwise manipulated.

2. Treatment Day (Day −1)

On Day −1(12-36 hours prior to HSCT), eligible patients will receive single IV infusion of either $140 \times 10^6 \pm 20\%$ cell/kg of multiple individual donors irradiated Early apoptotic Cellsl. Vital signs will be monitored every hour during infusion and every 4 hours for the first 24 hours afterwards. Treatment-related AEs will be assessed immediately following infusion.

On Day 0, patients will undergo hematopoietic stem cell transplantation according to local institution guidelines.

3. Short-Term Follow-Up Period (Day 0 to Day 180)

Patients will be followed-up to Study Day 180 for assessment of the primary endpoint safety and tolerability and secondary and tertiary endpoints: cumulative incidence of aGVHD grade II-IV ("modified Glucksberg" consensus based on Przepiorka et al cumulative incidence of any grade and high grade aGVHD, i.e., time to development of aGVHD, grades II-IV; any systemic treatment of GVHD, and the development of cGVHD.

The short term follow up visits will be daily while hospitalized for the transplantation (usually at least Days −1 to +14 or more) and weekly visits during the first 7 weeks after discharge; days +7, +14, +21. +28, +35, +42, and then on Days 60, 100, 140, and 180. The visit window will be ±5 days for each weekly visit (first 7 weeks) and ±5 days for biweekly or more visits during the subsequent follow up period up to 180 days.

Blood samples will be obtained on days 1, 3, 7, +7, +28, +42, 60, 100, 140 and 180 and examined for documentation of engraftment, immunological recovery, plasma and serum biomarkers ("Michigan") and cell subpopulations.

4. Long-Term Follow Up Period (Day 181 to Day 365/1 Year)

Patients will be followed for one year post-HSCT for the longer term secondary endpoints: non-relapse mortality and overall survival (OS), relapse incidence, leukemia free survival (LFS) and chronic GVHD. There will be at least two long-term follow-up visits, the last one being, 12±1 months following the HSCT.

Study Duration: For each participating patient, the duration in the study will be up to 14 months as follows:
A. Screening Up to 60 days (2 months
B. Treatment 1 day
C. Follow-up 365 days (12 months) consisting of
D. Short-term: 180 days
E. Long-term +180 days Study Population: A total of 25 patients diagnosed with hematologic malignancies scheduled to undergo HSCT (either bone marrow transplantation or peripheral blood stem cell transplantation), with at least 15 unrelated donors, following either myeloablative or reduced intensity conditioning regimens, per center standard practice will be included in this study and will be compared to historical controls.

Inclusion/Exclusion Criteria:

Recipient Patient Exclusion Criteria

1. Patients, Age>18, who are eligible for allogeneic HSCT for the following malignancies:
    A. Acute myeloid or undifferentiated or biphenotypic, leukemia, in complete remission (any remission) or beyond but with <5% blasts by morphology in bone marrow.
    B. Acute myeloid leukemia (AML) in complete remission if it has evolved from myelodysplastic syndrome (MDS) (there should be documented diagnosis of MDS at least 3 months prior to diagnosis of acute myeloid leukemia). Or evolved from polycythemia vera or essential thrombocytosis.
C. Acute lymphoblastic leukemia (ALL) in complete remission (any remission) with <5% blasts by morphology in bone marrow.
D. Chronic myeloid leukemia (CML) in chronic or accelerated phase
E. Myelodysplastic syndromes—refractory cytopenia with multilineage dysplasia (RCMD), RA (refractory anemia), RA with ringed sideroblast (RARS; all <5% blasts), RA with excess blasts (RAEB; 5 to 20% blasts).

The transplant donor and recipient patient must have at least an 8/8 HLA match at the HLA A, B, C, DQ, and DR loci and no antigen or allele mismatch. However the donor(s) of leukocytes for apoptotic cell formation is not restricted to HLA matching.

Performance status score of at least 70% at time of the screening visit (Karnofsky for adults and Lansky for recipient <16 years old.

Cardiac left ventricular ejection fraction ≥40% in adults within 4 weeks of initiation of conditioning; MUGA scan or cardiac ECHO required if prior anthracycline exposure or history of cardiac disease.

Pulmonary function test with DLCO[1], FEV1 (forced expiratory volume) and FVC (forced vital capacity) of ≥60% predicted.

[1] Diffusing capacity of the lung for carbon monoxide

Oxygen saturation of at least 90% on room air.

Patients must have adequate organ function as defined below:
A. AST (SGOT)/ALT (SGPT)<3× upper limit of normal (ULN).
B. Serum creatinine<2.0 mg/dL (adults, >16 y) or <0.8 (1-2 y), <1 (3-4 y), <1.2 (5-9 y), <1.6 (10-13 y), and 1.8 (14-15 y).
C. Serum bilirubin <3 mg/dL unless due to Gilbert's disease or hemolysis.

Signed written informed consent to participate in the study independently by patient, or guardian in the case of minors.

Ability to comply with the requirements of the study.

For duration of 4 weeks (from day −1), both female and male must agree to:
A. Use an acceptable method of birth control or be surgically sterile for the first month or more if there are BMT related restrictions.
B. To have a negative pregnancy test regardless of childbearing potential.

Recipient Patient Exclusion Criteria

All diseases eligible for HSCT not specified in the Inclusion Criteria.

Participation in an interventional investigational trial within 30 days of the screening visit.

Have progressive or poorly controlled malignancies.

If BMT plan include T-cell depleted allograft

If BMT plan include anti-thymocyte globulin (ATG) or alemtuzumab as part of immunosuppressive regimen or high dose Cyclophosphamide therapy for the prevention of GVHD after transplantation Uncontrolled infections including sepsis, pneumonia with hypoxemia, persistent bacteremia, or meningitis within two weeks of the screening visit.

Current known active acute or chronic infection with HBV or HCV.

Known human immunodeficiency virus (HIV) infection.

Patients with severe or symptomatic restrictive or obstructive lung disease or respiratory failure requiring ventilator support.

Patients with other concurrent severe and/or uncontrolled medical condition which could compromise participation in the study (i.e. active infection, uncontrolled diabetes, uncontrolled hypertension, congestive cardiac failure, unstable angina, ventricular arrhythmias, active ischemic heart disease, myocardial infarction within six months, chronic liver or renal disease, active upper gastrointestinal tract ulceration).

Any chronic or acute condition susceptible of interfering with the evaluation of investigational product effect.

Any form of substance abuse (including drug or alcohol abuse), psychiatric disorder or any chronic condition susceptible, in the opinion of the investigator, of interfering with the conduct of the study.

Organ allograft or previous history of stem cell transplantation (allogeneic only).

Breast feeding in women of childbearing potential.

Patients who are likely to be non-compliant or uncooperative during the study.

Investigational Product Route and Dosage Form

Apoptotic cells will be administered as an IV infusion of $140 \times 10^6 \pm 20\%$ cell/kg of irradiated multiple donor apoptotic cell product 12-36 hours prior to HSCT.

Apoptotic cells are a cell-based therapeutic composed of multiple individual donors apoptotic cells. The product contains allogeneic donor mononuclear enriched cells in the form of liquid suspension with at least 40% early apoptotic cells. The suspension is prepared from multiple individual donors with PBS solution in accordance with GMP regulations and should be stored at 2-8° C. until infusion. The final product will be in a total volume of 300-600 mL in an opaque transfer pack and will be irradiated with 25 Gy following preparation. Investigational product should be administered to the patient within 48 hours of completing the manufacturing process.

Safety Outcomes/Efficacy Endpoints/Outcome Measures

Primary:

Safety and tolerability endpoints include time to engraftment and a physical examination to determine adverse events, concomitant medications and safety laboratories on Day 180 and Day 360 (1 year). Further, it is expected that irradiated pooled apoptotic cell preparations will show a lack of in vitro and in vivo cell proliferation and lack of in vivo activation. Such a showing identifies the pooled apoptotic cell preparation as safe for use.

Secondary:
A. Cumulative incidence of aGVHD grade II-IV using "modified Glucksberg" consensus based on (Przepiorka et al., 1995) on Day 180
B. 1-year non-relapse mortality and overall survival (OS)
C. 1-year relapse incidence
D. 1-year leukemia free survival (LFS)
E. Maximum grade of aGVHD within the first 180 days
F. Cumulative incidence of grade III-IV aGVHD
G. Incidence of chronic GVHD according to (Jagasia et al., 2015) on Days 180 and 360 (1 year).
H. Any "systemic treatment" including corticosteroids (both used or not and cumulative dosage) for the treatment of aGvHD on Day 20 through Day 180

I. Immune reconstitution and function on Days +28, 100, 180 and 360 (1 year) in relation to T, B, NK, and Monocytes J. Major infection rate (including lung infiltrates, CMV reactivation and any other infections that require hospitalization) through Day 180 and 1 year.

Tertiary/Exploratory:

A. Percent of hospitalization days to total days at risk, or total days alive and out of the hospital. Or total hospitalization days till first discharge post transplantation.

B. Organ specific GVHD

C. T regs, CD4 Tcon, CD8, NK and B cells levels on Day 180

Statistical Analysis:

Study outcome will be compared to historical control with individuals with comparable baseline characteristics.

Descriptive statistics will be used to summarize outcome measures and baseline characteristics. In this analysis all available data will be presented with no imputation for any missing data. Subjects will contribute the data available up to the point of withdrawal or study completion or death. The descriptive statistics such as means, median, standard deviation, minimum and maximum will be used to summarize continuous variables. All subjects who receive the apoptotic cells infusion will be included in the safety analysis. Subjects who also receive the HSCT will be included in the efficacy analysis. As this study is exploratory in nature, ad hoc analyses are planned.

Sample Size Consideration

A total of 25 patients will be included at least 15 matched unrelated patients will be enrolled. Apoptotic cells (active will be given to all, stratifying on GVHD prophylaxis regimen, and related versus unrelated transplant donor.

Population Analysis Definition

All efficacy analyses will be conducted on the Intent-to-Treat (ITT) population and compared to adequate historical control. The safety population will be defined as all patients who receive a dose of study medication.

Statistical Methods

Patient, disease, and transplant characteristics will be described using frequencies and percentages or median (range) as appropriate.

Safety Analysis

Descriptive statistics will be used to summarize safety outcomes with focus on the AEs reported between study treatment infusion and HSCT procedure (24-30 hour window). No alterations in the conduct of the study will be initiated as a consequence of the DSMB review, including sample size adjustment. As such, no penalty adjustment in the overall Type I error as a consequence of the interim analysis will be required.

Secondary Endpoint Analysis

Grade II-IV aGVHD will be described using the cumulative incidence estimator with death prior to aGVHD as a competing event.

Neutrophil and platelet recovery, Grade III-IV aGVHD, chronic GVHD, infection, relapse, and transplant related mortality will be described using cumulative incidence with relapse as competing event for TRM and death as the competing event for all others. Overall survival and leukemia free survival will be described using the Kaplan-Meier estimator, and. The maximum grade of aGVHD within the first 180 days and the need for steroids at 180 days will be described using frequencies and percentages using the Mann-Whitney U-test and chi-square test respectively. Immune recovery of each cell subset and TREGs will be described at each time point using median and range Mann-Whitney tests.

Example 5: Comparison of Pooled Apoptotic Cell Preparation Vs. Single Donor Apoptotic Cell Preparation in GvHD Leukemia/Lymphoma Models Objective: Compare the beneficial clinical effect of human early apoptotic cells obtained from a single donor on the severity of GvHD in a murine model of GvHD, to the clinical effect, if any, of human early apoptotic cells obtained from multiple individual donors on the severity of GvHD in the murine model of GvHD, wherein the multiple individual donors represented HLA-unmatched heterologous donors.

Example 2 above shows the beneficial effect of irradiated apoptotic cells pooled from multiple individual donors. The results shown in FIG. 1 and FIG. 2 were surprising as a skilled artisan may recognize that the multiple sources of unmatched cells may have increased the diversity of antigenicity of the cells, and thus would have expected a dramatic reduction in the clinical effect. Unexpectedly, the known, beneficial effect of early apoptotic cells on the reduction of GvHD severity, and therefore a prolongation of the number of days till mortality, was also alleviated by pooled unmatched early apoptotic cells (FIG. 1), which would purportedly have increased antigenicity due to the pooled multiple unmatched source cells.

An additional objective was to understand if there is a difference between the use of irradiated early apoptotic cells and non-irradiated apoptotic cells.

A skilled artisan would appreciate that unmatched, irradiated cells keep their antigenic profile as recognized by the APC mechanism and so by T-Cells of the host into which they have been infused. Accordingly, concerns when pooling heterologous unmatched populations of cells included cross-reactivity between the individual populations being pooled, mixed-cell lymphatic reactions of pooled populations, or T-cell immune reactions between pooled populations that could reduce or eliminate cells, or any combination thereof.

Methods

Mouse model: Female 7-9 week-old BALB/c mice ($H-2^d$) were used as recipients and female 8-9 week-old C57BL/6 mice ($H-2^b$) were used as donors in mismatched GVHD model. Recipients were total body irradiated at 850 cGy 24 hours before bone marrow and splenocyte transplantation. Donor bone-marrow cells were used for bone-marrow reconstitution. Bone marrow cells were extracted from the femoral and tibial bones with RPMI 1640. Red blood cells were lysed, then cells were washed and resuspended with PBS. Viability was assessed using trypan blue dye exclusion (>90% viability). Donor splenocytes were used for the induction of GVHD. Spleens were removed and homogenized and single cell suspension was obtained. Red blood cells were lysed and splenocytes were resuspended with PBS. At least 90% viable cells were assessed using trypan blue dye.

Early apoptotic cells: Apoptotic cells were produced from mononuclear enriched cell fraction apheresis from healthy donors similar to Example 1. In brief:

Enriched fractions of mononuclear cells (MNCs) were obtained from healthy, eligible donors via leukapheresis procedure. Cells were collected via Spectra OPTIA® apheresis system from 12 liters of blood, in addition to 400-600 ml of autologous plasma. The estimated yield of the enriched mononuclear cell fraction from a donor was expected to be approximately $1.2-1.5\times10^{10}$ cells. Prior to leukapheresis procedure, donors are tested and confirmed negative to the below viral vectors:
1. Human Immunodeficiency virus (HIV), types 1 and 2;
2. Hepatitis B virus (HBV);
3. Hepatitis C virus (HCV);
4. Cytomegalovirus (CMV);
5. *Treponema pallidum* (syphilis);
6. Human T-lymphotropic virus (HTLV), types I and II Following cell collection, the cells were washed with RPMI and frozen as follows. The freezing formulation was composed of PlasmaLyte A for injection pH 7.4, 10% DMSO, 5% Human Serum Albumin and 5% Anticoagulant Citrate Dextrose solution inoculated with 10 U\ml heparin.

Freezing media was prepared in bags and the freezing procedure performed in a closed system under cGMP conditions.

Following leukapheresis procedure completion, enriched MNC fraction was washed with PlasmaLyte A and resuspended with ice-cold freezing media to a concentration of $50$-$65 \times 10^6$ cells\ml. Cells were then transferred to freezing bags, bags were transferred to pre-cooled aluminum cassettes and cassettes were transferred immediately to $-18$-$(-25)°$ C. for two hours.

Following the two hours, cassettes were transferred to $-80°$ C. for an additional 2 hours and then to long-term storage in liquid nitrogen ($>-135°$ C.).

Autologous plasma was divided to 50 gr aliquots. Plasma aliquots were transferred to $-80°$ C. for 2 hours and then to a long-term storage in $-18$-$(-25)°$ C.

For apoptosis induction cells were thawed and washed with pre-warmed RPMI1640 containing 10 mM Hepes buffer, 2 mM L-Glutamine and 5% Anticoagulant Citrate Dextrose solution inoculated with 10 U\ml heparin. After supernatant extraction cells were resuspended at final concentration of $5 \times 10^6$/ml in RPMI 1640 supplemented with 10 mM Hepes, 2 mM L-glutamine, with addition of 10% autologous plasma and. 50 μg\ml Methylprednisolone and 5% Anticoagulant Citrate Dextrose solution inoculated with 10 U\ml heparin. Cells are then transferred to cell culture bags, and incubated at humidified incubator 37° C., 5% $CO_2$ for 6 hours to stabilize apoptosis.

Following incubation cells were harvested, washed with PBS and resuspended in PBS.

Early apoptotic cell product was produced from one single donor or combined 10 different individual donors, in which case cells were combined just prior to irradiation. Since interference may occur between components in the multiple donor product, for example between living non-apoptotic cells, the early apoptotic cell product was subdivided and a sample of early apoptotic cells to be tested in vivo was irradiated with 2500 cGy prior to administration (sample F below), and stored at 2-8° C. until administration. Table 3 of Example 6 below presents details of the Annexin V positive/Propidium iodide negative ratio and cell surface markers of the early apoptotic cell product, establishing that consistency of apoptotic cells administered to mice is maintained. The final product was stable for 48 hours at 2-8° C.

On the day of transplantation, mice received $5 \times 10^6$ bone-marrow cells, $3 \times 10^6$ splenocytes and $30 \times 10^6$ single- or multiple-donor early apoptotic cell product, according to the following experimental design:
A. Irradiation control
B. Reconstitution control—irradiation+Bone-Marrow transplantation (BM)
C. GVHD control—irradiation+Bone-Marrow and splenocyte transplantation
D. Single donor, irradiated—irradiation+Bone-Marrow and splenocyte transplantation+irradiated early apoptotic cell product from single donor
E. Single donor, non-irradiated—irradiation+Bone-Marrow and splenocyte transplantation+non-irradiated early apoptotic cell product from single donor
F. Multiple donor, irradiated—irradiation+Bone-Marrow and splenocyte transplantation+irradiated early apoptotic cell product from multiple donor
G. Multiple donor, non-irradiated—irradiation+Bone-Marrow and splenocyte transplantation+non-irradiated early apoptotic cell product from multiple individual donors.

Monitoring—Transplanted mice were tagged and survival was monitored. Body weight was assessed every two days for the first two weeks of the experiment and then every day. Loss of 35% from initial body weight was determined as primary end point and mice were sacrificed and survival curve was updated accordingly. Body weight results were comparable to those observed in Example 3 FIG. 2.

The severity of GVHD was assessed using a known scoring system (Cooke K R, et al. An experimental model of idiopathic pneumonia syndrome after bone marrow transplantation. I. The roles of minor H antigens and endotoxin. Blood. 1996; 8:3230-3239) that incorporates five clinical parameters: weight loss, posture (hunching), activity, fur texture and skin integrity. Mice were evaluated and graded from 0 to 2 for each criterion. By summation of the five clinical scores a clinical index value was generated (index number increases with the severity of GVHD).

Results

Figure 3:
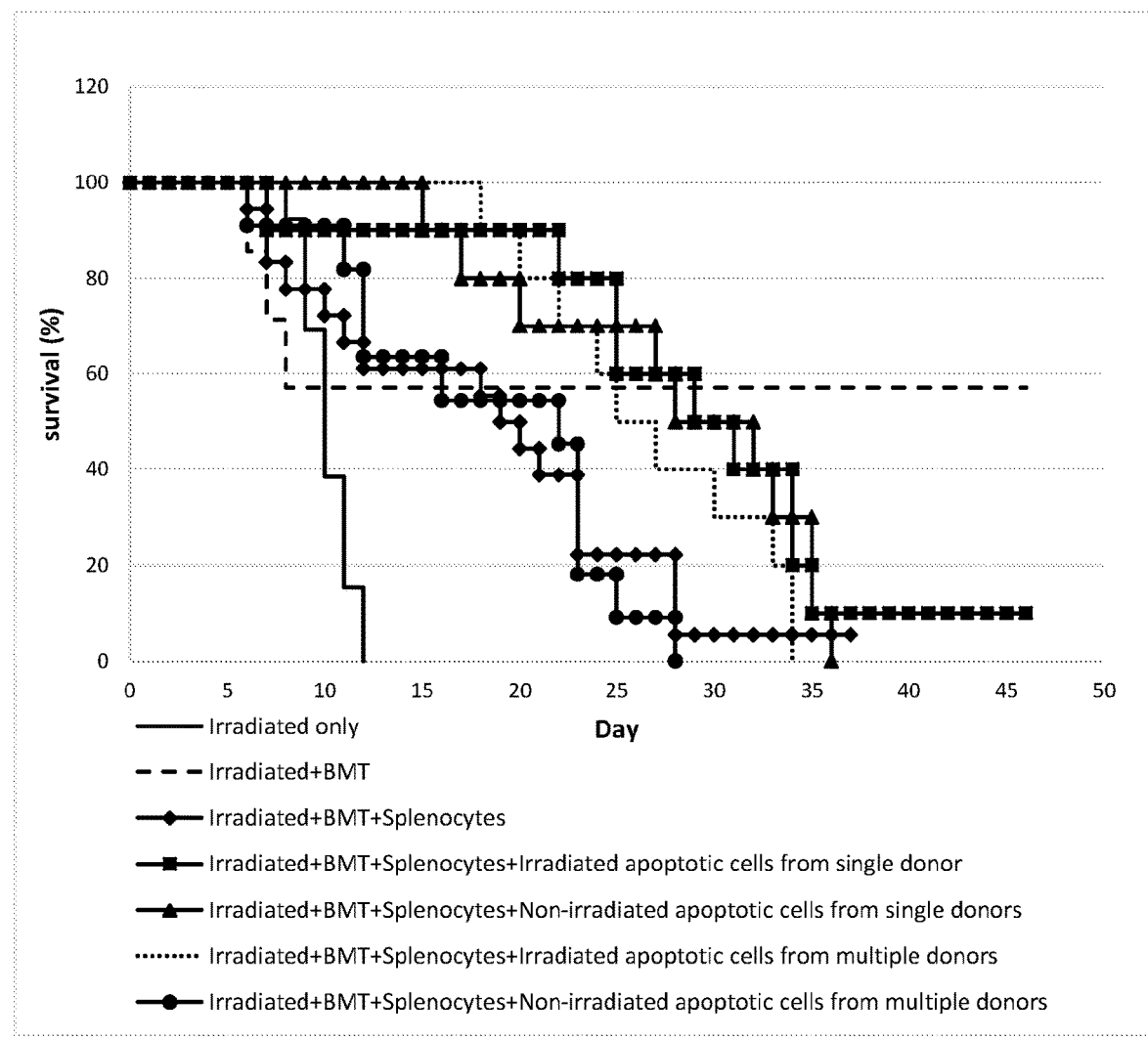
FIG. 3 presents a graph showing comparison between the administration of a single dose of single-donor and multiple-donor apoptotic cell preparations+/−irradiation on % survival using a mouse model of induced GvHD.

Percent survival of the different population of mice is presented graphically in FIG. 3. The irradiation only control mice died between day 8 and 12 (n=13), as expected from mice that did not receive bone marrow reconstitution. The majority of GVHD control mice (received bone-marrow and spleen) died between day 6 and 27. One mouse did not die (n=18). In bone-marrow reconstitution control group (BM) 3 out of 7 mice died between day 6 and 8. In the remaining mice, bone marrow was reconstituted by donor bone-marrow and mice remained alive (>50 days).

Single donor, non-irradiated mice died between day 15 and 36. Thus, as previously shown, single donor non-irradiated early apoptotic cells had a beneficial effect and survival was prolonged (p<0.01).

Single donor, irradiated mice died between day 7 and 35, one mouse remained disease free survival (>50 days). This demonstrated that single donor irradiated apoptotic cells also provided the beneficial effect with respect to GVHD. Thus, irradiation did not harm the immunomodulatory effect of early apoptotic cells. All had beneficial effect on survival in the GVHD murine model compared to GVHD control (p<0.01).

Non-irradiated multiple donor treatment did not provide a beneficial effect compared to GVHD control (n=11). Survival pattern was similar to GVHD control and mice died between day 6 and 28 (p=NS—not significant). Surprisingly and in contrast to the non-irradiated apoptotic cells, irradiated-multiple individual donor apoptotic cells (treatment F) (n=10) had a beneficial effect similar to single donor treatment, as compared with GVHD control. GVHD symptoms appeared significantly later and mice died between day 18 and 34 (p<0.01).

Irradiated-multiple individual donor (n=10), irradiated single donor (n=10) and non-irradiated single donor treatment (n=10) had similar survival patterns and no significant difference in effect on survival was observed between these three treatment groups.

The experiments indicated a clear effect of apoptotic cells infusion in GVHD induced mice. There was a significant prolonged survival effect for the treatments of irradiated multiple individual donors and irradiated- and non-irradiated single donor apoptotic cells.

Multiple donor treatment did not prolonged survival of mice when not irradiated but the irradiation of the apoptotic cell product prior to administration to mice improved results and treatment had close survival pattern as single-donor treatments.

As stated above, FIG. 3 shows, non-irradiated apoptotic cells obtained from multiple unmatched donors have significantly lower positive clinical effect on reduction in GvHD and mortality (% survival), as compared to (1) non-irradiated apoptotic cells obtained from single unmatched donors; (2) irradiated apoptotic cells obtained from single unmatched donors; and (3) irradiated apoptotic cells obtained from multiple unmatched donors. In addition, all three (non-irradiated early apoptotic cells, single donor; irradiated early apoptotic cells, single donor; and irradiated early apoptotic cells, multiple individual donors) have similar effects.

This data was surprising since the antigenicity of the non-irradiated apoptotic cells obtained from multiple individual donors was expected to be similar to that of irradiated apoptotic cells obtained from multiple individual donors, why would not both have similar hostile antigenic reaction with the implanted bone marrow, and why would both not be able to reduce GvHD and mortality rate?

If antigenicity is the main issue here, it was expected to see differences between the clinical effects of non-irradiated apoptotic cells obtained from single donor and irradiated apoptotic cells obtained from single donor. However the data does not show this difference.

One possibility is that the lack of efficacy of non-irradiated pooled apoptotic cell preparations prepared from multiple individual donors, resulted from cross-interaction between the individual mononuclear populations present in the pooled preparation. These interactions do not appear to be directly attributable to antigenicity towards the host, as irradiated cells maintain their antigenicity but the efficacy differed significantly from non-irradiated cells. Therefore, it appears that the cross-interaction in the pooled early apoptotic cell preparations receiving irradiation was unexpectedly eliminated and the host responded well to administration of the cells.

As shown, irradiated pooled donors had essentially the same effect as a single non irradiated donor.

Example 6: Effect of Irradiation on Final Apoptotic Cell Product

Apoptotic cells are increasingly used in novel therapeutic strategies because of their intrinsic immunomodulatory and anti-inflammatory properties. Early apoptotic cell preparations may contain as much as 20-40% viable cells (as measured by lack of PS exposure and no PI admission; Annexin V negative and Propidium iodide negative) of which some may be rendered apoptotic after use in a transfusion but some will remain viable. In the case of bone marrow transplantation from a matched donor, the viable cells do not represent a clinical issue as the recipient is already receiving many more viable cells in the actual transplant. However, in the case of a third party transfusion, (or fourth party or more as may be represented in a pooled mononuclear apoptotic cell preparation) use of an apoptotic cell population that includes viable cells may introduce a second GvHD inducer. Furthermore, the implication of irradiation on the immunomodulatory potential of early apoptotic cells has so far been not assessed. A skilled artisan may consider that additional irradiation of an early apoptotic cell population may lead cells to progress into later stages of apoptosis or necrosis. As this appears a particularly relevant question with regard to clinical applications, the experiments presented below were designed to address this issue, with at least one goal being to improve the biosafety of functional apoptotic cells.

Thus, the aim was to facilitate the clinical utilization of apoptotic cells for many indications wherein the potency of apoptotic cells may rely on a bystander effect rather than engraftment of the transplanted cells.

Objective: Examine the effect of irradiation on early apoptotic cells, wherein irradiation occurs following induction of apoptosis.

Methods (in brief): The cells were collected according and early apoptotic cells were prepared essentially as described in Example 5.

Three separate early apoptotic cell batches were prepared on different dates (collections 404-1, 0044-1 and 0043-1).

Each final product was divided into three groups:
Untreated
2500 rad
4000 rad.

Following irradiation, early apoptotic cells were tested immediately (to) for cell count, AnnexinV positive-PI negative staining, cell surface markers (% population of different cell types) and potency (dendritic cells (DCs)). Following examination at to, early apoptotic cells were stored at 2-8° C. for 24 hours, and examined the next day using the same test panel ($t_{24h}$) (cell count, Annexin V positive-PI negative staining, and cell surface markers and potency).

Previously, a post-release potency assay was developed, which assesses the ability of donor mononuclear early apoptotic cells (Early apoptotic CellsI) to induce tolerance (Mevorach et al, BBMT 2014 ibid). The assay is based on using flow cytometric evaluation of MHC-class II molecules (HLA-DR) and costimulatory molecule (CD86) expression on iDC membranes after exposure to LPS. As previously and repeatedly shown, tolerogenic DCs can be generated upon interaction with apoptotic cells (Verbovetsky et al., J Exp Med 2002, Krispin et al., Blood 2006), and inhibition of maturation of LPS-treated DCs (inhibition of DR and CD86 expression), occurs in a dose dependent manner During phase ½a of the early apoptotic cell clinical study, the post-release potency assay was conducted for each early apoptotic cell batch (overall results n=13) in order to evaluate the ability of each batch to induce tolerance (Results are shown in FIG. 1, Mevorach et al. (2014) Biology of Blood and Marrow Transplantation 20(1): 58-65).

DCs were generated for each early apoptotic cell batch from fresh buffy coat, collected from an unknown and unrelated healthy donor, and were combined with early apoptotic cells at different ratios (1:2, 1:4 and 1:8 DC:Early apoptotic Cells, respectively). After incubation with early apoptotic cells and exposure to LPS, potency was determined based on downregulation of DC membrane expression of either HLA DR or CD86 at one or more ratios of DC: early apoptotic cells. In all 13 assays, early apoptotic cells demonstrated a tolerogenic effect, which was seen with preparations at most DC: early apoptotic cells ratios, and for both markers, in a dose dependent manner.

Monocyte obtained immature DCs (iDCs) were generated from peripheral blood PBMCs of healthy donors and cultured in the presence of 1% autologous plasma, G-CSF and IL-4. iDCs were then pre-incubated for 2 hours at 1; 2, 1; 4 and 1; 8 ratios with apoptotic cells either freshly prepared final product or final product stored at 2-8° C. for 24 hours. The two final products were examined simultaneously in order to determine whether storage affects potency ability of apoptotic cells. Following incubation, LPS was added to designated wells were left for additional 24 hours. At the end of incubation, iDCS were collected, washed and stained with both DC-sign and HLA-DR or CD86 in order to determine changes in expression. Cells were analyzed using flow cytometer and analysis performed using FCS-express software from DC-sign positive cells gate to assure analysis on DCs only.

FIGS. 4A-B and FIGS. 5A-B show potency test of irradiated pooled apoptotic cells compared to non-irradiated single donor cell.

Results:

Single Donor Preparations

Table 8 presents the comparative results of non-radiated and irradiated apoptotic cells; Average cell loss (%) at 24 hours; Annexin positive($^+$) Propidium Iodide (PI) negative ($^-$) % at 0 hours and 24 hrs (% of early apoptotic cells; Annexin positive ($^+$) Propidium Iodide (PI) positive ($^+$) % at 0 hours and 24 hrs (% of late apoptotic cells); presence of cell surface antigens CD3 (T cells), CD19 (B cells), CD56 (NK cells), CD14 (monocytes), and CD15$^{high}$ (granulocyte), at 0 hours and 24 hours.

TABLE 8

| Final product description | Apoptotic Cell | Apoptotic Cell 2500 rad | Apoptotic Cell 4000 rad |
|---|---|---|---|
| An$^+$PI$^-$ t$_0$ (%) | 59.2 | 59.6 | 58.4 |
| Range (min-max) | (52.6-66.1) | (51.6-68.7) | (50.4-65.1) |
| An$^+$PI$^-$ t$_{24\,h}$ (%) | 62.6 | 68.1 | 66.7 |
| Range (min-max) | (53.6-76.3) | (52.0-81.3) | (52.9-77.1) |
| An$^+$PI$^+$ t$_0$ (%) | 4.9 | 6.0 | 6.1 |
| Range (min-max) | (3.2-7.0) | (5.2-7.4) | (4.0-9.1) |
| An$^+$PI$^+$ t$_{24\,h}$ (%) | 7.3 | 8.6 | 9.0 |
| Range (min-max) | (5.0-11.8) | (6.4-11.8) | (6.0-14.9) |
| CD3+ t$_0$ (%) | 56.9 | 58.3 | 57.5 |
| Range (min-max) | (47.4-66.3) | (48.8-67.7) | (48.6-66.4) |
| CD3+ t$_{24\,h}$ (%) | 56.8 | 57.1 | 56.6 |
| Range (min-max) | (49.6-64.0) | (48.0-66.1) | (49.7-63.4) |
| CD19+ t$_0$ (%) | 10.6 | 9.5 | 9.6 |
| Range (min-max) | (10.1-11.0) | (7.7-11.3) | (8.5-10.7) |
| CD19+ t$_{24\,h}$ (%) | 11.8 | 9.2 | 8.8 |
| Range (min-max) | (10.2-13.4) | (6.9-11.5) | (7.5-10.1) |
| CD56+ t$_0$ (%) | 12.2 | 13.0 | 14.4 |
| Range (min-max) | (7.0-17.3) | (7.6-18.4) | (21.2-7.6) |
| CD56+ t$_{24\,h}$ (%) | 12.9 | 14.1 | 17.1 |
| Range (min-max) | (8.8-13.4) | (10.4-17.8) | (10.0-24.1) |
| CD14+ t$_0$ (%) | 23.1 | 25.2 | 24.6 |
| Range (min-max) | (13.1-33.1) | (13.8-36.5) | (14.0-35.2) |
| CD14+ t$_{24\,h}$ (%) | 21.9 | 23.7 | 24.4 |
| Range (min-max) | (13.8-30.0) | (13.8-33.6) | (15.4-33.4) |
| CD15$^{high}$ t$_0$ (%) | 0.0 | 0.0 | 0.01 |
| Range (min-max) | | | (0.0-0.02) |
| CD15$^{high}$ t$_{24\,h}$ (%) | 0.0 | 0.0 | 0.01 |
| Range (min-max) | | | (0.0-0.02) |

The results in Table 8 show that both non-irradiated apoptotic cells and irradiated apoptotic cells had comparable percentages of early (rows 2 and 3) and late (rows 4 and 5) apoptotic cells. Thus, 25 or 40 Gy irradiation did not accelerate the apoptotic or necrotic process induced prior to this high level of gamma-irradiation. Further, there was consistency between irradiated cell populations vs. control non-irradiated population with regard to cell type.

Figures 5A, 5B:
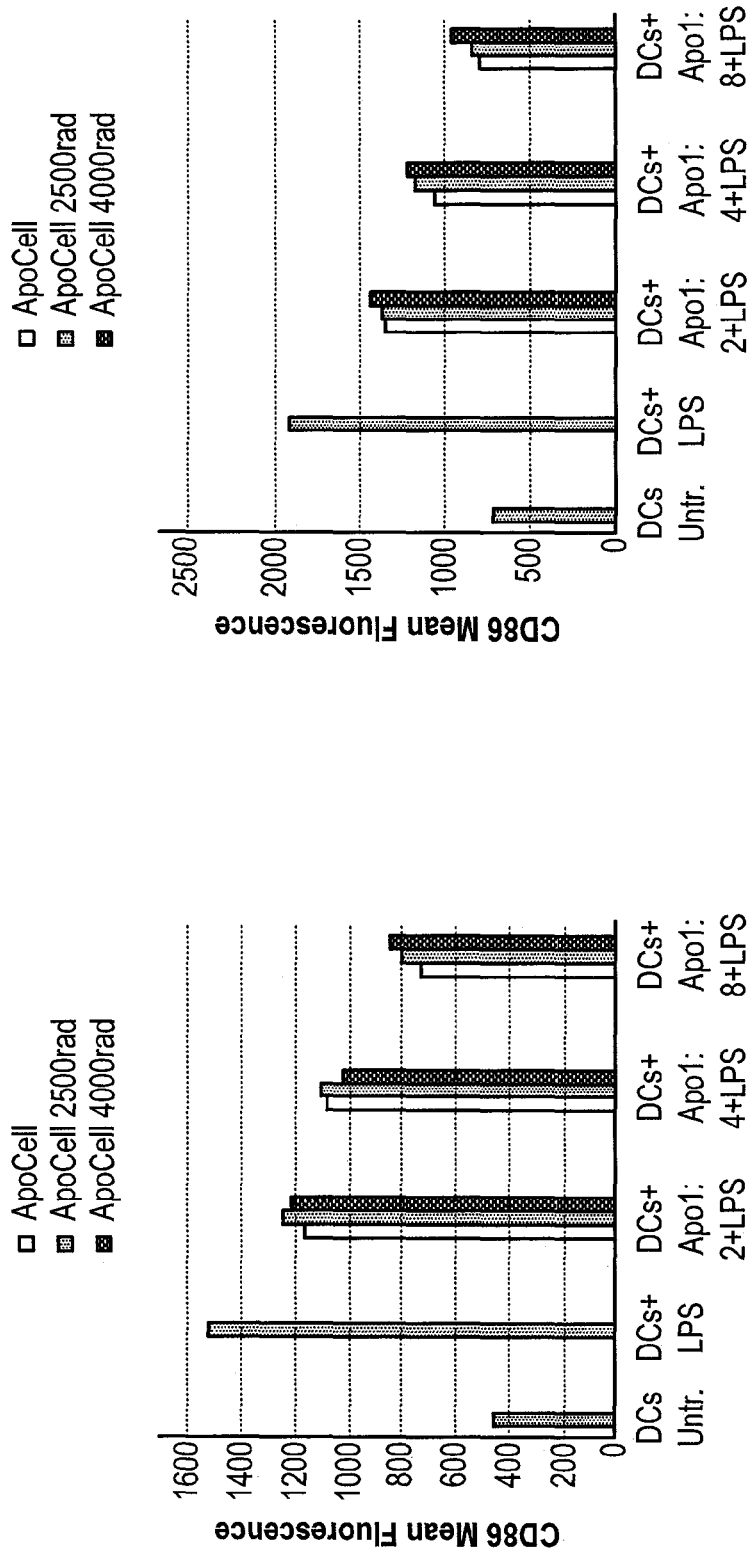
FIGS. 5A-B presents the results of a potency test that shows the inhibition of maturation of dendritic cells (DCs) following interaction with apoptotic cells, measured by expression of CD86.

The results of potency assays, presented in FIGS. 4A-4B (HLA-DR expression) and FIGS. 5A-5B (CD86 expression) show that there was no change in the immune modulatory capacity of fresh (FIG. 4A, FIG. 5A) and 24 hour-stored (FIG. 4B, FIG. 5B) irradiate apoptotic cells when compared with non-irradiated apoptotic cells.

In both FIGS. 4A-B and FIGS. 5A-B there is a clear upregulation in both HLA-DR and CD86 expression, following exposure to maturation agent LPS. Significant ($p<0.01$), dose-dependent down regulation of both co-stimulatory markers was observed in the presence of freshly prepared apoptotic cells both from a single donor or irradiated pooled donors. In addition, dose dependent down regulation was maintained in both markers in the presence of apoptotic cells stored at 2-8° C. for 24 hours, indicating final product stability and potency following 24 hours of storage.

Effect on dendritic cells, In order to test the immunomodulatory capacity of apoptotic cells a post release potency assay was used (Mevorach et al., (2014) BBMT, ibid). No change in immune modulatory assay in dendritic cells was observed. (Data not shown)

Effect on Mixed Lymphocyte Reaction (MLR). In order to further test the immunomodulatory effect a standardized MLR assay was established. Here, co-cultivation of stimulator and responder cells, i.e. a MLR, yielded strong and reliable proliferation. Upon addition of non-irradiated apoptotic cells to the MLR, the lymphocyte proliferation was significantly reduced by >5-fold, clearly demonstrating cell inhibition of proliferation. Inhibition of lymphocyte proliferation in MLRs mediated by irradiated apoptotic cells was completely comparable. (Data not shown)

The next step was to evaluate in vivo, irradiated and non-irradiated apoptotic cells in a completely mismatched mouse model. As shown in FIGS. 1-2, irradiated and non-irradiated early apoptotic cell preparations had comparable in vivo beneficial effect.

Single Donor Preparations Conclusion:

In conclusion, irradiation of 25 Gy or 40 Gy did not significantly accelerate apoptosis or induced necrosis in populations of apoptotic cells. Significantly, these populations maintained the immunomodulatory effect of apoptotic cells both in vitro and in vivo.

Multiple Donor Preparations

Next, experiments were performed to verify that the phenomenon observed with single donor, third party preparation was also true for multiple third party donors. Unexpectedly, when using pooled individual donor apoptotic cell preparations, the beneficial effect of a single unmatched donor was lost (FIG. 3). This was not due to GvHD, as the beneficial effect of each donor separately was maintained (test results no shown). One possibility is that the beneficial effect of the early apoptotic cell preparation was lost due to the interaction of the individual donor cells among themselves. It was further examined whether this possible interaction of different donors could be avoided by gamma irradiation.

As shown in FIG. 3, the beneficial effect of a single donor was completely restored following gamma irradiation, wherein the irradiated multiple donor preparation and the single donor preparation (irradiated or non-irradiated) had similar survival patterns.

Conclusion:

It is shown here for the first time that surprisingly irradiation (and possibly any method leading to T-cell Receptor inhibition) not only avoided unwanted proliferation and activation of T-cells but also allowed for the beneficial effects of immune modulation when using a preparation of multiple donor third party apoptotic cells.

While certain features have been illustrated and described herein, many modifications, substitutions, changes, and equivalents will now occur to those of ordinary skill in the art. It is, therefore, to be understood that the appended claims are intended to cover all such modifications and changes as fall within the true spirit of the disclosure herein.

What is claimed is:

1. A method of prolonging survival of a subject suffering from an immune disease, an autoimmune disease, a cytokine release syndrome (CRS), a cytokine storm, a cancer, or an inflammatory disease, comprising administering to the subject a pharmaceutical composition comprising an irradiated mononuclear-enriched, early apoptotic cell preparation, wherein said early apoptotic cells are irradiated post induction of apoptosis, and wherein said irradiated mononuclear-enriched, early apoptotic cell preparation comprises
   a decreased number of non-quiescent non-apoptotic cells;
   a suppressed cellular activation of any living non-apoptotic cells; or
   a reduced proliferation of any living non-apoptotic cells;
   or any combination thereof compared with a preparation comprising a non-irradiated cell population.

2. The method of claim 1, wherein said irradiated mononuclear-enriched, early apoptotic cell preparation comprises irradiated and pooled, mononuclear, early apoptotic cell preparations.

3. The method of claim 2, wherein individual mononuclear-enriched populations are pooled prior to induction of apoptosis or post induction of apoptosis and are obtained from a single donor or from multiple donors.

4. The method of claim 2, wherein said pooled, individual, mononuclear cell populations comprises populations pooled independent of HLA matching of said individual mononuclear cell populations' HLA markers; or at least one cell type selected from the group consisting of: lymphocytes, monocytes, dendritic cells, and natural killer cells; or cells comprising inactive T cell receptors or reduced immune activity; or any combination thereof.

5. The method of claim 2, said mononuclear cell populations comprise cells obtained from between about 2 and 25 units of blood.

6. The method of claim 5, wherein said blood comprises white blood cell (WBC) fractions from blood donations.

7. The method of claim 2, wherein said mononuclear cell populations comprise allogeneic cells from HLA matched or HLA unmatched sources, with respect to a recipient subject.

8. The method of claim 1, wherein said irradiation comprises gamma irradiation or UV irradiation.

9. The method of claim 1, wherein the immune disease is selected from the group comprising GVHD, arthritis, gout, or inflammatory bowel disease.

10. The method of claim 1, wherein said CRS or cytokine storm is the result of an infection.

11. The method of claim 1, wherein said subject is suffering from:
   a hematopoietic malignancy or sepsis,
   retains a graft-versus-tumor or graft-versus-leukemia (GVL) effect,
   is undergoing hematopoietic stem-cell transplantation (HSCT), or
   is undergoing solid organ transplantation.

12. The method of claim 11, wherein the HSCT is allogeneic HSCT.

13. The method of claim 11, wherein the administering of the pharmaceutical composition is carried out up to 24 hours prior to said transplantation, at the same time as the transplantation, or is administered until 15 days following said transplantation.

14. The method of claim 1, wherein following administration of said irradiated mononuclear-enriched, early apoptotic cell preparation, the subject remains disease free.

15. The method of claim 1, wherein said pharmaceutical composition is administered by intravenous injection.

16. A therapeutic, irradiated, mononuclear, early apoptotic cell preparation comprising a mononuclear-enriched cell population in an early apoptotic state that is irradiated post induction of apoptosis, and wherein said irradiated mononuclear-enriched, early apoptotic cell preparation comprises
   a decreased number of non-quiescent non-apoptotic cells;
   a suppressed cellular activation of any living non-apoptotic cells; or
   a reduced proliferation of any living non-apoptotic cells;
   or any combination thereof compared with a preparation comprising non-irradiated cell populations.

17. The cell preparation of claim 16, wherein said mononuclear-enriched cell population is derived from a white blood cell (WBC) fraction from a blood donation.

18. The cell preparation of claim 16, wherein said mononuclear cell population comprises allogeneic cells from an HLA matched or HLA unmatched source, with respect to a recipient subject.

19. The cell preparation of claim 16, wherein said irradiation comprises gamma irradiation or UV irradiation.

20. A pharmaceutical composition, comprising the therapeutic irradiated early apoptotic cell preparation of claim 16.

21. A method for producing a pharmaceutical composition comprising an irradiated mononuclear apoptotic cell preparation comprising a mononuclear cell population in an early apoptotic state, said method comprising the following steps,
   (a) obtaining a mononuclear-enriched cell population of peripheral blood;
   (b) freezing said mononuclear-enriched cell population in a freezing medium comprising an anticoagulant;
   (c) thawing said mononuclear-enriched cell population;
   (d) incubating said mononuclear-enriched cell population in an apoptosis inducing incubation medium comprising methylprednisolone at a final concentration of about 10-100 µg/mL and an anticoagulant, wherein induction produces an early apoptotic cell population;
   (e) resuspending said induced early apoptotic cell populations obtained in step (d) in an administration medium; and
   (f) inactivating said early apoptotic cell populations from step (e), wherein said inactivation comprises irradiating said apoptotic cell populations from step (e), and wherein said irradiation comprises gamma irradiation or UV irradiation at about 20-60 Grey units (Gy);
wherein said method produces a pharmaceutical composition comprising an irradiated mononuclear apoptotic cell preparation, wherein said irradiated mononuclear-enriched, early apoptotic cell preparation comprises
   a decreased number of non-quiescent non-apoptotic cells;
   a suppressed cellular activation of any living non-apoptotic cells; or
   a reduced proliferation of any living non-apoptotic cells;
   or any combination thereof compared with a preparation comprising non-irradiated cell populations.

22. The method of claim 21, wherein said obtaining said individual, mononuclear-enriched cell population comprises obtaining a white blood cell (WBC) fraction by leukapheresis.

23. The method of claim 22, wherein said white blood cell (WBC) fraction comprises
- (a) WBC fraction obtained from a blood bank; or
- (b) at least one cell type selected from the group consisting of lymphocytes, monocytes, dendritic cells, and natural killer cells;
- (c) or any combination thereof.

24. The method of claim 21, wherein said obtaining of said individual, mononuclear-enriched cell population is not restricted by HLA matching said individual, mononuclear-enriched cell population.

25. The method of claim 21, wherein said incubating is for about 2-12 hours.

26. The method of claim 21, wherein said mononuclear-enriched cell population comprises allogeneic cells from HLA-matched or HLA-unmatched sources with respect to a recipient subject.

* * * * *